(12) United States Patent
Cheng et al.

(10) Patent No.: US 10,494,538 B2
(45) Date of Patent: Dec. 3, 2019

(54) SWITCHABLE ANTIMICROBIAL AND ANTIFOULING CARBOXYBETAINE-BASED HYDROGELS AND ELASTOMERS WITH ENHANCED MECHANICAL PROPERTIES

(71) Applicants: Gang Cheng, Fairlawn, OH (US); Bin Cao, Akron, OH (US)

(72) Inventors: Gang Cheng, Fairlawn, OH (US); Bin Cao, Akron, OH (US)

(73) Assignee: THE UNIVERSITY OF AKRON, Akron, OH (US)

(*) Notice: Subject to any disclaimer, the term of this patent is extended or adjusted under 35 U.S.C. 154(b) by 671 days.

(21) Appl. No.: 14/893,561

(22) PCT Filed: May 30, 2014

(86) PCT No.: PCT/US2014/040353
§ 371 (c)(1),
(2) Date: Nov. 24, 2015

(87) PCT Pub. No.: WO2014/194268
PCT Pub. Date: Dec. 4, 2014

(65) Prior Publication Data
US 2017/0362458 A1    Dec. 21, 2017

Related U.S. Application Data

(60) Provisional application No. 61/828,782, filed on May 30, 2013, provisional application No. 61/866,222, filed on Aug. 15, 2013.

(51) Int. Cl.
| C09D 133/14 | (2006.01) |
| C08F 220/36 | (2006.01) |
| C08F 20/36 | (2006.01) |
| C07C 229/12 | (2006.01) |
| C07C 233/38 | (2006.01) |
| C09D 133/26 | (2006.01) |
| C09D 139/00 | (2006.01) |
| C08F 20/34 | (2006.01) |
| C08F 22/38 | (2006.01) |
| C08F 222/38 | (2006.01) |
| A01N 37/12 | (2006.01) |
| C07C 227/02 | (2006.01) |
| C07C 227/16 | (2006.01) |
| C07C 227/18 | (2006.01) |
| C08F 120/36 | (2006.01) |
| C09D 5/14 | (2006.01) |

(52) U.S. Cl.
CPC ........... *C09D 133/14* (2013.01); *A01N 37/12* (2013.01); *C07C 227/02* (2013.01); *C07C 227/16* (2013.01); *C07C 227/18* (2013.01); *C07C 229/12* (2013.01); *C07C 233/38* (2013.01); *C08F 20/34* (2013.01); *C08F 20/36* (2013.01); *C08F 22/385* (2013.01); *C08F 120/36* (2013.01); *C08F 220/36* (2013.01); *C08F 222/385* (2013.01); *C09D 5/14* (2013.01); *C09D 133/26* (2013.01); *C09D 139/00* (2013.01)

(58) Field of Classification Search
CPC ..... C09D 133/14; C09D 133/26; C08F 20/34; C08F 20/36; C08F 20/58; C08F 20/60; C08F 120/34; C08F 120/36; C08F 120/58; C08F 120/60; C08F 220/34; C08F 220/36; C08F 220/58; C08F 220/60
See application file for complete search history.

(56) References Cited

U.S. PATENT DOCUMENTS

2011/0305872 A1* 12/2011 Li ..................... A61L 29/06
                                            428/141
2015/0133566 A1*  5/2015 Gong ................ C09D 135/02
                                            514/772.6

* cited by examiner

*Primary Examiner* — Roberto Rabago
(74) *Attorney, Agent, or Firm* — Renner Kenner Greive Bobak Taylor & Weber

(57) ABSTRACT

Various embodiments of the present invention are directed to switchable carboxybetaine-based polymers, hydrogels, and/or elastomers, along with novel related monomers, cross-linkers, and methods. Under acidic conditions, the materials undergo self-cyclization and can catch and kill bacteria. Under neutral/basic conditions, these materials undergo ring-opening and can release killed bacterial cells and resist protein adsorption and bacterial attachment. These smart polymers, hydrogels and elastomers also show excellent mechanical properties making them highly desirable for many biomedical applications.

23 Claims, 29 Drawing Sheets

A

B

C

D

E

F

A

B

C

D

SWITCHABLE ANTIMICROBIAL AND ANTIFOULING CARBOXYBETAINE-BASED HYDROGELS AND ELASTOMERS WITH ENHANCED MECHANICAL PROPERTIES

CROSS REFERENCE TO RELATED APPLICATIONS

This application claims the benefit of U.S. provisional patent application Ser. No. 61/828,782 entitled "Switchable Antimicrobial and Antifouling Hydrogels with Enhanced Mechanical Property," filed May 30, 2013, and U.S. provisional patent application Ser. No. 61/866,222 entitled "All-In-One Carboxybetaine Elastomer," filed August, 2013, which are incorporated herein by reference in their entirety.

REFERENCE TO GOVERNMENT SUPPORT

This invention was made with government support under grant numbers NSF CMMI-1129727 and NSF ECCS-1200032 awarded by the National Science Foundation. The government has certain rights in the invention.

FIELD OF THE INVENTION

One or more embodiments of the present invention relates to switchable antimicrobial and antifouling materials and coatings for use in various biomedical applications. In certain embodiments, one or more embodiments of the present invention relate to switchable antimicrobial and antifouling carboxybetaine-based hydrogels and elastomers with enhanced mechanical properties.

BACKGROUND OF THE INVENTION

Recently, there has been increasing interests in antifouling materials for use in various biomedical applications. Fouling is an undesired process in which molecules and/or living organisms from environment attach and accumulate onto a surface. The undesired surface adsorption of biomacromolecules for example, can cause the failure of biomedical devices. Thus, materials with superior antifouling properties have been urgently sought.

In recent years, zwitterionic materials, especially carboxybetaine (CB)-based materials, have attracted great attention due to their outstanding antifouling properties, as well as the capability of further functionalization for biosensing and drug delivery. These materials have been proven to effectively reduce bacterial attachment, biofilm formation, and highly resist nonspecific protein adsorption even from undiluted blood plasma.

These zwitterionic coatings can reduce initial attachment and delay biofilm formation on surfaces, but they are not able to kill attached microorganisms. Pathogenic microbes are sometimes introduced into the patient during implantation operations and catheter insertions, causing the failure of implanted devices are necessary to antimicrobial agents to eliminate these microbes. Surface-responsive materials with antimicrobial properties have been developed for a broad spectrum of applications, but there has been a need for materials and coatings having both antimicrobial and antifouling/biocompatibility capabilities.

To address this issue, a cationic derivative of pCBMA was developed. A surface coated with the cationic derivative of pCBMA is able to catch and kill bacterial cells, switch to a zwitterionic antifouling surface, and release killed bacterial cells upon its hydrolysis. However, it was found that this material can only switch once from antimicrobial state to antifouling state and the process is not reversible. Moreover, the alcohol leaving groups also may not be suitable for applications which require that no small molecules to be leaked out. Therefore, a material that can reversibly switch between an antifouling surface and an antimicrobial surface is highly desired.

Hydrogels, which can trap water molecules inside their three-dimensional network, have been widely used as wound dressings, drug delivery carriers, tissue engineering scaffolds, and coatings for implantable biosensor. Zwitterionic material-based hydrogels have attracted notable attention due to their ultralow fouling properties described above, good biocompatibility and high water content. However, the potential biomedical applications of zwitterionic hydrogels have been limited by their low mechanical strength, among other things. Although the mechanical strength can be improved through the blending or co-polymerization of the zwitterionic monomers with other materials, such as 2-hydroxyethyl methacrylate) (HEMA) and N-isopropylacrylamide (NIPAm), the antifouling properties of these zwitterionic monomers are very often compromised.

Another problem with existing zwitterionic materials is that they are relatively fragile and not stretchable. This significantly limits their utility for flexible medical devices (such as heart valve, implantable biosensors, and tissue scaffolds) which require implanted materials to be elastic and fouling-resistant. The current hydrophobic elastic materials cannot resist bacterial attachment.

Accordingly, what is needed in the art is zwitterionic material integrating all desired and tunable properties including excellent antifouling property to prolong the lifetime of implanted materials, antimicrobial property to eliminate surgical infection and chronic inflammation, and good mechanical properties/stability to avoid the structure failure of the implanted material.

SUMMARY OF THE INVENTION

In a general outline, the present invention is directed to a novel switchable zwitterionic polymer hydrogels and elastomers, along with novel related monomers, crosslinkers, and methods. Under acidic conditions, the materials undergo self-cyclization and can catch and kill bacteria. Under neutral/basic conditions, these materials undergo ring-opening and can release killed bacterial cells and resist protein adsorption and bacterial attachment. Smart hydrogels also show a dramatically improved mechanical properties which are highly desired for biomedical applications.

In a first aspect, the present invention provides a zwitterionic composition having excellent antifouling and antimicrobial properties and improved mechanical properties comprising: a polymer backbone formed from monomers selected from the group consisting of acrylates, methacrylates, acrylamides, methacrylamides, vinyl alcohols, serines and combinations thereof; one or more zwitterionic moieties chemically bonded to said polymer backbone, said zwitterionic moieties further comprising a carboxybetaine group having at least one ethanol, propanol, butanol or pentanol group bonded to the nitrogen atom of said carboxybetaine group; and a crosslinking compound.

In one or more embodiments, the zwitterionic composition is a hydrogel. In one or more embodiments, the zwitterionic composition includes any one or more of the above referenced embodiments of the first aspect of the present invention wherein said composition is an elastomer.

In one or more embodiments, the zwitterionic composition includes any one or more of the above referenced embodiments of the first aspect of the present invention wherein said polymer backbone is selected from the group consisting of polymethacrylate, polyethylacrylate, polymethacrylamide, polyethylacrylamide poly(2-hydroxyethyl methacrylate), polyserine, polyvinyl alcohol, polyols and combinations thereof In one or more embodiments, the zwitterionic composition includes any one or more of the above referenced embodiments of the first aspect of the present invention wherein said one or more zwitterionic moieties have a formula selected from the group consisting of:

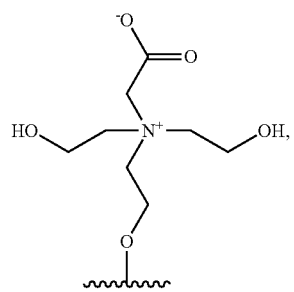

(I)

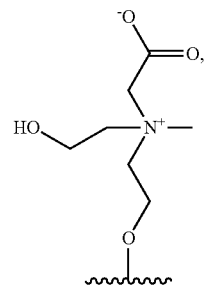

(II)

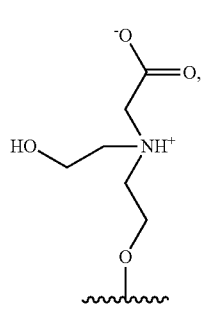

(III)

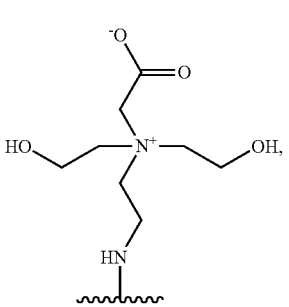

(IV)

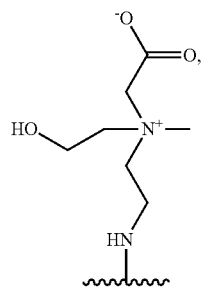

(V)

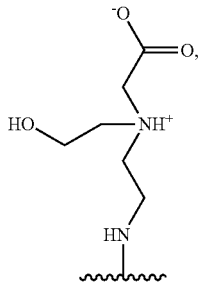

(VI)

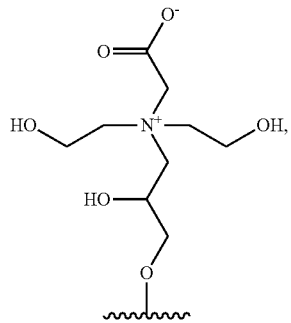

(VII)

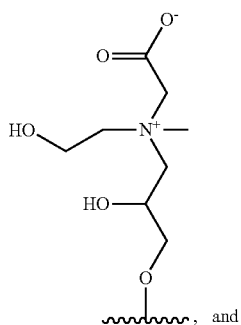, and (VIII)

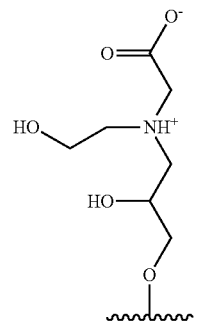

(IX)

wherein 〰 is the polymer backbone.

In one or more embodiments, the zwitterionic composition includes any one or more of the above referenced embodiments of the first aspect of the present invention having the formula:

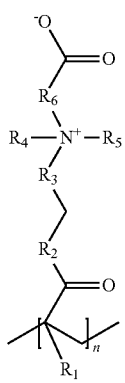

(X)

wherein $R_1$ is H, —$CH_3$ or —$CH_2CH_3$; $R_2$ are O or NH; $R_3$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$ or $CH_2CH_2CH_2CH_2CH_2OH$; $R_1$ is H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$ or $CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$— and n is an integer from 2 to 10,000.

In one or more embodiments, the zwitterionic composition includes any one or more of the above referenced embodiments of the first aspect of the present invention wherein said one or more zwitterionic moieties have a formula:

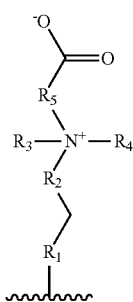

(XI)

wherein $R_1$ is O or NH; $R_2$ is-$CH_2$—, —$CH_2CH_2$—, —$CH_2CH_2CH_2$—, —$CH_2CH_2CH_2CH_2$—, or —$CH_2CH_2CH_2CH_2CH_2$—; $R_3$ is —$CH_2CH_2OH$, —$CH_2CH_2CH_2OH$, —$CH_2CH_2CH_2CH_2OH$ or $CH_2CH_2CH_2CH_2CH_2OH$; $R_4$ is H, —$CH_3$, —$CH_2CH_3$, —$CH_2CH_2CH_3$, —$CH_2CH_2$ $CH_3$, —$CH_2CH_2OH$, —$CH_2CH_2CH_2OH$, —$CH_2CH_2$ $CH_2OH$ or $CH_2CH_2CH_2CH_2CH_2OH$; $R_1$ is —$CH_2$—, —$CH_2CH_2$—, —$CH_2CH_2CH_2$—, —$CH_2CH_2CH_2CH_2$—, or —$CH_2CH_2CH_2CH_2CH^2$— and ⌇ is the polymer backbone.

In one or more embodiments, the zwitterionic composition includes any one or more of the above referenced embodiments of the first aspect of the present invention wherein said one or more zwitterionic moieties have a formula:

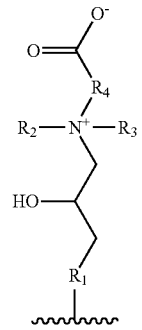

(XII)

wherein $R_1$ is O or NH; $R_2$ is —$CH_2CH_2OH$, —$CH_2CH_2CH_2OH$, —$CH_2CH_2CH_2CH_2OH$ or $CH_2CH_2CH_2CH_2CH_2OH$; $R_3$ is H, —$CH_3$, —$CH_2CH_3$, —$CH_2CH_2CH_3$, —$CH_2CH_2CH_2CH_3$, —$CH_2CH_2OH$, —$CH_2CH_2$ $CH_2OH$, —$CH_2CH_2CH_2CH_2OH$ or $CH_2CH_2CH_2$ $CH_2CH_2OH$; $R_4$ is —$CH_2$—, —$CH_2CH_2$—, —$CH_2$ $CH_2CH_2$—, —$CH_2CH_2CH_2CH_2$—, or —$CH_2CH_2$ $CH_2CH_2$—; and ⌇ is the polymer backbone.

In one or more embodiments, the zwitterionic composition includes any one or more of the above referenced embodiments of the first aspect of the present invention wherein said one or more zwitterionic moieties have the formula:

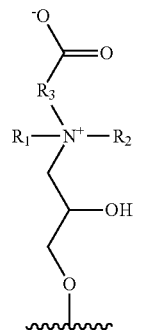

(XIII)

wherein $R_1$ is —$CH_2CH_2OH$, —$CH_2CH_2CH_2OH$, —$CH_2CH_2CH_2CH_2OH$ or $CH_2CH_2CH_2CH_2CH_2OH$; $R_2$ is H, —$CH_3$, —$CH_2CH_3$, —$CH_2CH_2CH_3$, —$CH_2CH_2$ $CH_2CH_3$, —$CH_2CH_2OH$, —$CH_2CH_2CH_2OH$, —$CH_2CH_2$ $CH_2CH_2OH$ or $CH_2CH_2CH_2CH_2CH_2OH$; R3 is —$CH_2$—, —$CH_2CH_2$—, —$CH_2CH_2CH_2$—, —$CH_2CH_2CH_2CH_2$—, or —$CH_2CH_2CH_2CH_2CH_2$—; and ⌇ is the polymer backbone.

In one or more embodiments, the zwitterionic composition includes any one or more of the above referenced embodiments of the first aspect of the present invention wherein said one or more zwitterionic moieties are selected from the group consisting of 2-(bis(2-hydroxyethyl)(methylene)ammonio)acetate, 2-((2-hydroxyethyl)(methylene) (methyl)ammonio)acetate, 2-((2-hydroxyethyl)(methylene) ammonio)acetate, 3-(bis(2-hydroxyethyl)(methylene) (methyl)ammonio) propanoate, 3-((2-hydroxyethyl)

(methylene)(methyl)ammonio)propanoate, 3-((2-hydroxyethyl)(methylene)ammonio)propanoate and combinations and analogs/derivatives thereof.

In one or more embodiments, the zwitterionic composition includes any one or more of the above referenced embodiments of the first aspect of the present invention wherein said each of said one or more zwitterionic moieties has a corresponding cationic ring form. In one or more embodiments, the zwitterionic composition includes any one or more of the above referenced embodiments of the first aspect of the present invention wherein the corresponding cationic ring form has the formula:

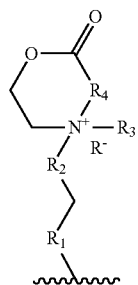

(XIV)

wherein $R_1$ is O or NH; $R_2$ is —$CH_2$—, —$CH_2CH_2$—, —$CH_2CH_2CH_2$—, —$CH_2CH_2CH_2CH_2$—, or —$CH_2CH_2CH_2CH_2$—; $R_3$ is —H, $CH_3$, $CH_2CH_3$, —$CH_2CH_2CH_3$, —$CH_2CH_2CH_2CH_3$, $CH_2CH_2OH$, —$CH_2CH_2CH_2OH$, —$CH_2CH_2CH_2CH_2OH$, —$CH_2CH_2CH_2CH_2CH_2OH$; $R_4$ is —$CH_2$—, —$CH_2CH_2$—, —$CH_2CH_2CH_2$—, —$CH_2CH_2CH_2CH_2$—, —$CH_2CH_2CH_2CH_2CH_2$—; $R^-$ is any organic or inorganic anion; and ~~~ is the polymer backbone.

In one or more embodiments, the zwitterionic composition includes any one or more of the above referenced embodiments of the first aspect of the present invention wherein the corresponding cationic ring form of said one or more zwitterionic moieties has the formula:

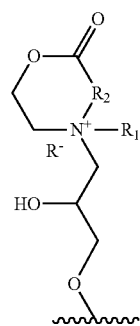

(XV)

wherein $R_1$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; $R_2$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R^-$ is any organic or inorganic anion; and ~~~ is the polymer backbone.

In one or more embodiments, the zwitterionic composition includes any one or more of the above referenced embodiments of the first aspect of the present invention wherein the corresponding cationic ring form of said one or more zwitterionic moieties has a formula selected from the group consisting of:

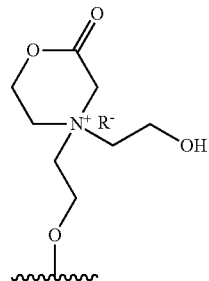

(XVI)

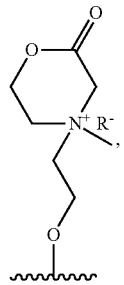

(XVII)

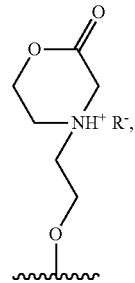

(XVIII)

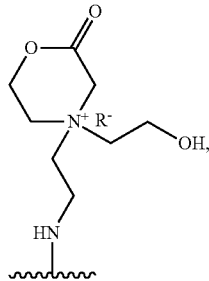

(XIX)

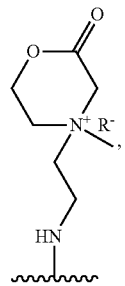

(XX)

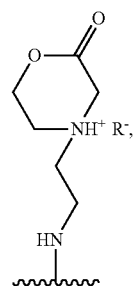
(XXI)
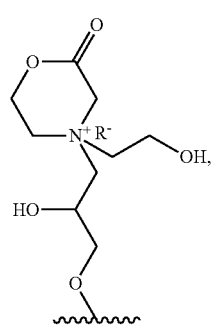
(XXII)
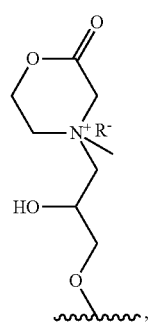
(XXIII)
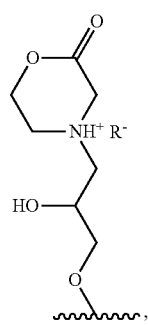
(XXIV)
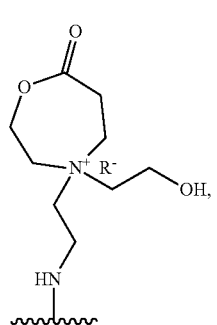
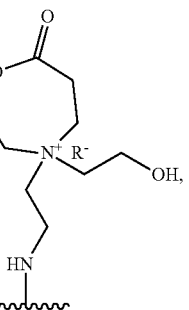
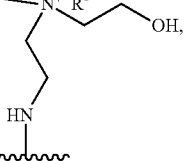
(XXV)
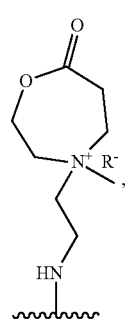
(XXVI)
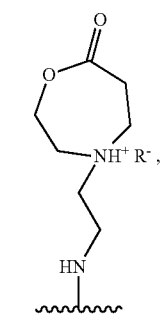
(XXVII)
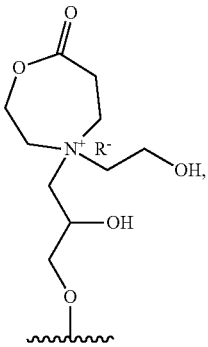
(XXVIII)
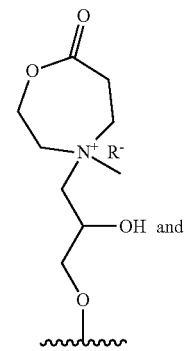
(XXIX)

(XXX)

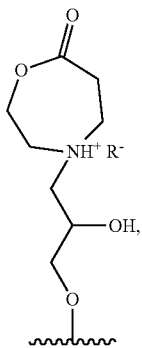

wherein R is any organic or inorganic anion and ~~~ is the polymer backbone.

In one or more embodiments, the zwitterionic composition includes any one or more of the above referenced embodiments of the first aspect of the present invention wherein said one or more crosslinking compound comprises a compound selected from the group consisting of di(methyl)acrylate, multi-(methyl)acrylate, di(methyl)acrylamide, multi-(methyl)acrylamide, diepoxide multi-epoxide, dithiol and multi-thiol, and combinations thereof.

In one or more embodiments, the zwitterionic composition includes any one or more of the above referenced embodiments of the first aspect of the present invention wherein said one or more crosslinking compound has the formula:

(XXXI)

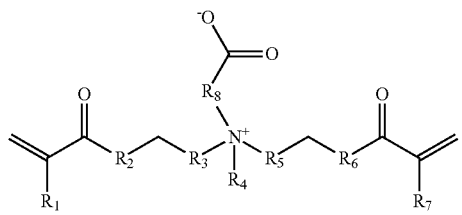

wherein $R_1$ and $R_7$ are —H, —$CH_3$, or —$CH_2CH_3$; $R_2$ and $R_6$ are O or NH; $R_3$ and $R_5$ are —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —H, $CH_3$, $CH_2CH_3$, $CH_2CH_2OH$, —$CH_2CH_2CH_2OH$, —$CH_2CH_2CH_2CH_2OH$, or —$CH_2CH_2CH_2CH_2CH_2OH$; and $R_8$ is —$CH_2$—, —$CH_2CH_2$—, —$CH_2CH_2CH_2$—, —$CH_2CH_2CH_2CH_2$—, or $CH_2CH_2CH_2CH_2CH_2$—.

In one or more embodiments, the zwitterionic composition includes any one or more of the above referenced embodiments of the first aspect of the present invention wherein said one or more crosslinking compound is selected from the group consisting of carboxybetaine di(methyl)acrylate, carboxybetaine di(methyl)acrylamide, poly(ethylene glycol) di(methyl)acrylate, 1,3-Propanedithiol, 1,4-Butanedithiol, 1,3-Butadiene diepoxide, and combinations and/or analogs thereof.

In one or more embodiments, the zwitterionic composition includes any one or more of the above referenced embodiments of the first aspect of the present invention wherein said one or more crosslinking compound has the formula:

(XXXII)

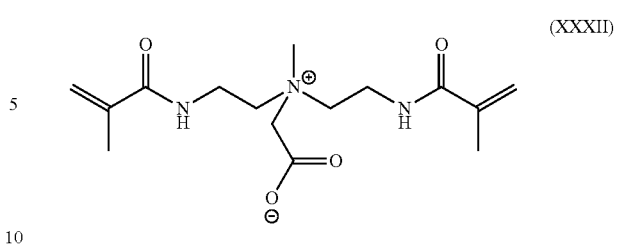

In a second aspect, the present invention provides a carboxybetaine-based composition having excellent antifouling and antimicrobial properties and improved mechanical properties comprising: a zwitterionic polymer selected from the group consisting of poly(2-((2-hydroxyethyl)(2-methacrylamidoethyl)(methyl)ammonio)acetate), poly(3-((2-hydroxyethyl)(2-methacrylamidoethyl)(methyl)ammonio)propanoate), poly(2-((2-hydroxyethyl)(2-(methacryloyloxy)ethyl)(methyl) ammonio)acetate) and poly(2-(bis (2-hydroxyethyl)(2-(methacryloyloxy)ethyl) ammonio)acetate) and combinations and/or analogs thereof; and a crosslinker.

In one or more embodiments, the crosslinker selected from the group consisting of carboxybetaine di(methyl)acrylate, carboxybetaine di(methyl)acrylamide, poly(ethylene glycol) di(methyl)acrylate, 1,3-Propanedithiol, 1,4-Butanedithiol, 1,3-Butadiene diepoxide, and combinations and/or analogs thereof.

In one or more embodiments, the zwitterionic composition includes any one or more of the above referenced embodiments of the second aspect of the present invention wherein said crosslinker has the formula:

(XXXII)

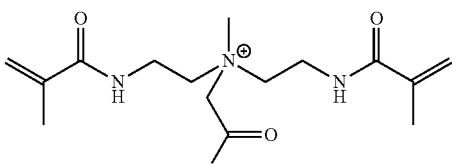

In one or more embodiments, the zwitterionic composition includes any one or more of the above referenced embodiments of the second aspect of the present invention wherein the crosslinker has the formula:

(XXXIII)

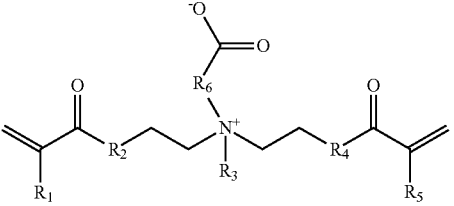

wherein $R_1$ and $R_5$ are H, —$CH_3$, or —$CH_2CH_3$; $R_2$ and $R_4$ are O or NH; $R_3$ is H, —$CH_3$, —$CH_2CH_2OH$, —$CH_2CH_2O$—$COCH$=$CH_2$, —$CH_2CH_2O$—$COC(CH_3)$=$CH_2$, —$CH_2CH_2NH$—$COCH$=$CH_2$, or —$CH_2CH_2NH$—$COC(CH_3)$=$CH_2$ and $R_6$ is —$CH_2$—, —$CH_2CH_2$—, —$CH_2CH_2CH_2$—, —$CH_2CH_2CH_2CH_2$—, —$CH_2CH_2CH_2CH_2CH_2$—

In one or more embodiments, the zwitterionic composition includes any one or more of the above referenced embodiments of the second aspect of the present invention wherein the crosslinker has the formula:

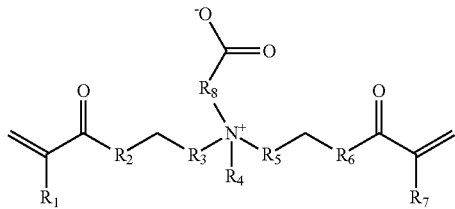
(XXXI)

wherein $R_1$ and $R_7$ are —H, —$CH_3$, or —$CH_2CH_3$; $R_2$ and $R_6$ are O or NH; $R_3$ and $R_5$ are —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$—H, $CH_3$, $CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_8$ is —$CH_2CH_2$—, —$CH_2CH_2CH_2$—, —$CH_2CH_2CH_2CH_2$—, or —$CH_2CH_2CH_2CH_2CH_2$—.

In a third aspect, the present invention provides a zwitterionic monomer having the formula:

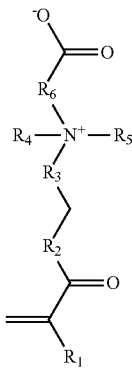
(XXXVI)

wherein $R_1$ is —H, —$CH_3$, or —$CH_2CH_3$; $R_2$ is O or NH; $R_3$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$, or —$CH_2CH_2CH_2CH_2CH_2OH$; $R_1$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

In some embodiments the zwitterionic monomer may be 2-((2-hydroxyethyl)(2-(methacryloyloxy)ethyl)ammonio) acetate, 2-((2-hydroxyethyl)(2-(methacryloyloxy)ethyl) (methyl)ammonio)acetate, 2-(bis(2-hydroxyethyl)(2-(methacryloyloxy)ethyl)ammonio)acetate, 2-((2-hydroxyethyl)(2-methacrylamidoethyl)ammonio)acetate, 2-(bis(2-hydroxyethyl)(2-methacrylamidoethyl)ammonio)acetate, 2-((2-hydroxyethyl)(2-methacrylamidoethyl)(methyl)ammonio)acetate, 3-((2-hydroxyethyl)(2-methacrylamidoethyl)(methyl) ammonio)propanoate, or combinations and analogs/ derivatives thereof.

In one or more embodiments, the zwitterionic composition includes any one or more of the above referenced embodiments of the third aspect of the present invention having a formula selected from the group consisting of:

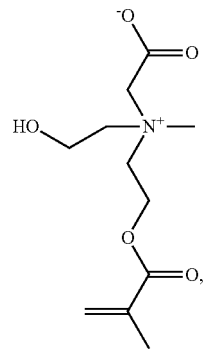
(XXXVIII)

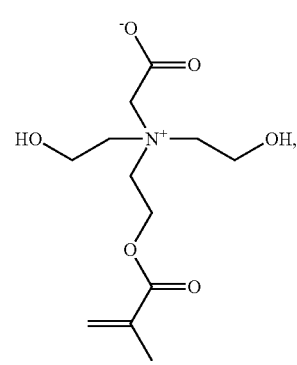
(XXXIX)

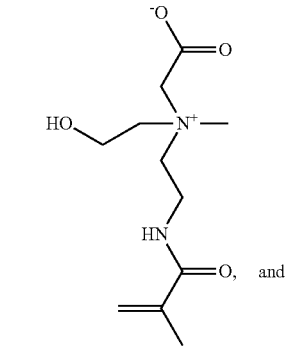
(XL)

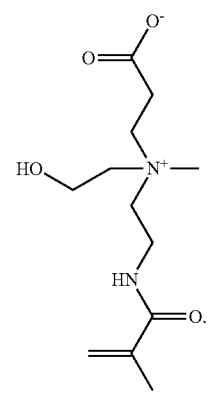
(XLI)

In a fourth aspect, the present invention provides a zwitterionic monomer having the formula:

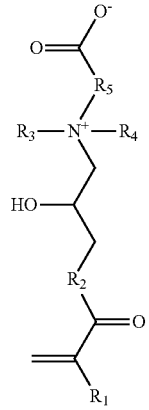
(XLII)

wherein $R_1$ is —H, —$CH_3$, —$CH_2CH_3$; $R_2$ is O or NH; $R_3$ is —$CH_2CH_2OH$, —$CH_2CH_2CH_2OH$, —$CH_2CH_2CH_2CH_2OH$, or —$CH_2CH_2CH_2CH_2CH_2OH$; $R_4$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_1$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

The zwitterionic monomer of claim 27 selected from the group consisting of 2-((2-hydroxyethyl)(2-(methacryloyloxy)ethyl)(methyl)ammonio)acetate, 2-(bis(2-hydroxyethyl)(2-(methacryloyloxy)ethyl)ammonio)acetate, 2-((2-hydroxyethyl)(2-methacrylamidoethyl)(methyl)ammonio)acetate, 3-((2-hydroxyethyl)(2-methacrylamidoethyl)(methyl)ammonio)propanoate and combinations and analogs/derivatives thereof. In one or more embodiments, the zwitterionic composition includes any one or more of the above referenced embodiments of the fourth aspect of the present invention having a formula of:

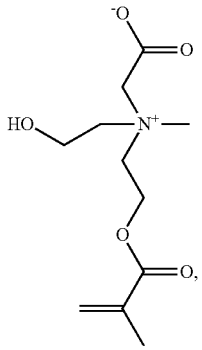
(XXXVIII)

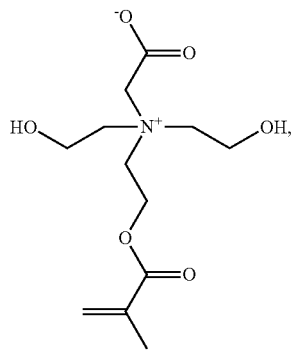
(XXXIX)

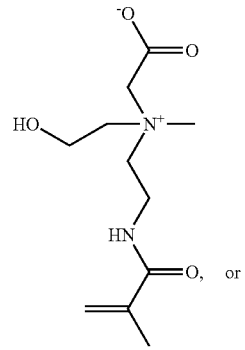
(XL)

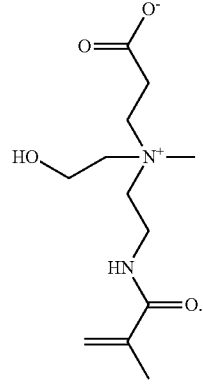
(XLI)

In another aspect, the present invention provides a zwitterionic composition having the formula:

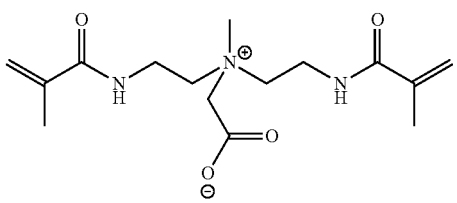
(XXXII)

In another aspect, the present invention provides a method for forming a novel zwitterionic monomer comprising: dissolving N-methyl diethanol amine in an anhydrous organic solvent and an anhydrous base; reacting the solution of step A with a stoichiometric quantity of methacryloyl chloride to produce 2-((2-hydroxyethyl)(methyl)amino) ethyl methacrylate; dissolving the 2-((2-hydroxyethyl) (methyl)amino)ethyl methacrylate of step B in a suitable organic solvent and reacting it with tert-butyl bromoacetate to produce 2-(tert-butoxy)-N-(2-hydroxyethyl)-N-(2-methacryloyloxy)ethyl)-N-methyl-2-oxoethanaminium bromide; dissolving the 2-(tert-butoxy)-N,N-bis(2-hydroxyethyl)-N-(2-(methacryloyloxy)ethyl)-2-oxoethanaminium bromide of step C in a suitable organic solvent and reacting it with trifloroacetic acid and recovering the reaction product; and dissolving the reaction product of step D in an suitable solvent and neutralizing it over a basic ionic exchange resin to produce 2-((2-hydroxyethyl)(2-(methacryloyloxy)ethyl)(methyl)ammonio)acetate (CBOH1).

In another aspect, the present invention provides a method for forming the novel zwitterionic monomer comprising: dissolving tri-(2-hydroxyethyl)amine in an anhydrous organic solvent and an anhydrous base; reacting the solution of step A with a stoichiometric quantity of methacryloyl chloride to produce 2-(bis(2-hydroxyethyl)amino)ethyl methacrylate; dissolving the 2-(bis(2-hydroxyethyl)amino)ethyl methacrylate of step B in a suitable organic solvent and reacting it with tert-butyl bromoacetate to produce 2-(tert-butoxy)-N,N-bis(2-hydroxyethyl)-N-(2-(methacryloyloxy)ethyl)-2-oxoethanaminium bromide; dissolving the 2-(tert-butoxy)-N,N-bis(2-hydroxyethyl)-N-(2-(methacryloyloxy)ethyl)-2-oxoethanaminium bromide of step C in a suitable organic solvent and reacting it with trifluoroacetic acid and recovering the reaction product; and dissolving the reaction product of step D in a suitable solvent and neutralizing it over a basic ionic exchange resin to produce 2-(bis(2-hydroxyethyl)(2-(methacryloyloxy)ethyl)ammonio)acetate (CBOH2).

In still another aspect, the present invention provides a method for forming the novel zwitterionic monomer comprising: dissolving a base in a suitable solvent and adding 2-((2-aminoethyl)amino)ethanol; cooling the product of step A and reacting it with a stoichiometric quantity of methacrylic anhydride under a dry gas atmosphere to produce N-(2-((2-hydroxyethyl)amino)ethyl)methacrylamide; dissolving the N-(2-((2-hydroxyethyl)amino)ethyl)methacrylamide in a suitable solvent and reacting it with tert-butyl bromoacetate or tert-butyl acrylate to produce tert-butyl N-(2-hydroxyethyl)-N-(2-methacrylamidoethyl)glycinate or tert-butyl 3-((2-hydroxyethyl)(2-methacrylamidoethyl)amino)propanoate; dissolving the reaction product in a suitable solvent and reacting it with methyl iodide under a dry gas atmosphere; the reaction product is then reacted with trifluoroacetic acid (TFA) in a suitable solvent and the reaction product collected; and re-dissolving that reaction product in a suitable solvent and neutralizing it over a basic ionic exchange resin to produce form 2-((2-hydroxyethyl)(2-methacrylamidoethyl)(methyl)ammonio)acetate (CBMAA-1) or 3-((2-hydroxyethyl)(2-methacrylamidoethyl)(methyl)ammonio)propanoate (CBMAA-2). In some embodiments of this aspect of the present invention, steps D is omitted and the reaction products on step F comprises 2-((2-hydroxyethyl)(2-methacrylamidoethyl)ammonio)acetate or 3-((2-hydroxyethyl)(2-methacrylamidoethyl)ammonio)propanoate.

In yet another aspect, the present invention provides a method for forming the novel zwitterionic monomer comprising: dissolving a base in a suitable solvent and adding diethylenetriamine; cooling the product of step A and reacting the solution of step A with a stoichiometric quantity of methacrylic anhydride under a nitrogen atmosphere to produce N,N'-(azanediylbis(ethane-2,1-diyl))bis(2-methylacrylamide); dissolving the N,N'-(azanediylbis(ethane-2,1-diyl)) bis(2-methylacrylamide) in a suitable organic solvent and reacting it with tert-butyl bromoacetate to produce tert-butyl bis(2-methacrylamidoethyl)glycinate (3); dissolving the reaction product of step C in a suitable solvent and reacting it with methyl iodide under a dry gas atmosphere; reacting the product of step D with trifloroacetic acid (TFA) in a suitable solvent and collecting the reaction product; and re-dissolving the reaction product of step E in suitable solvent and neutralizing it over a baic ionic exchange resin to produce form 2-(bis(2-methacrylamidoethyl)(methyl)ammonio)acetate.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1A:
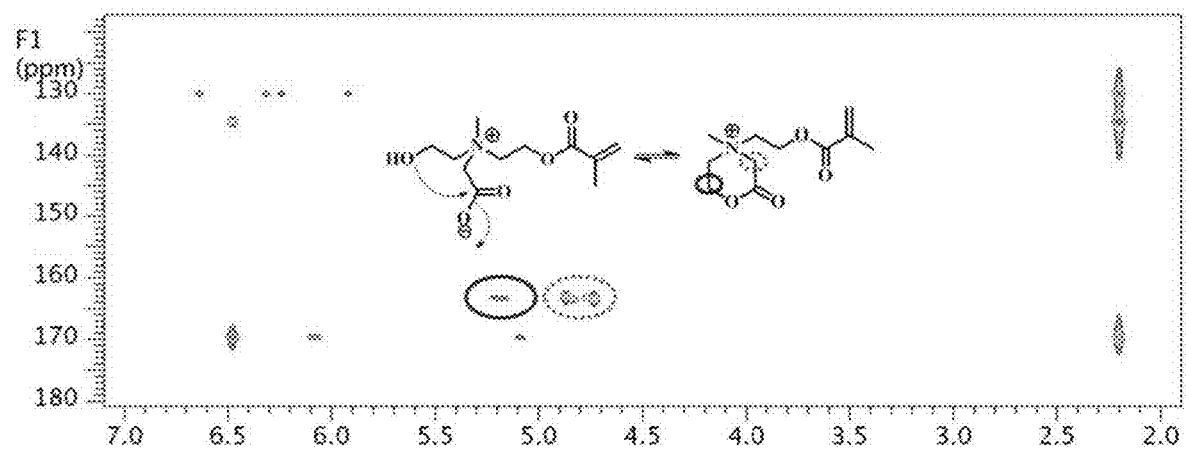
FIG. 1A-B is a 500 MHz $^1$H-$^{13}$C gHMBC NMR spectrum of CBOH1 (1A) and CBOH2 (1B) which switch between zwitterionic form and cationic ring form.

In general outline, various embodiments of the present invention are directed to switchable carboxybetaine-based polymers, hydrogels, and/or elastomers, along with novel related monomers, crosslinkers, and methods. Under acidic conditions, the materials undergo self-cyclization and can catch and kill bacteria. Under neutral/basic conditions, these materials undergo ring-opening and can release killed bacterial cells and resist protein adsorption and bacterial attachment. These smart polymers, hydrogels and elastomers show excellent mechanical properties making them highly desirable for many biomedical applications.

As used herein, the term "carboxybetaine" refers to any neutral chemical compound with a positively charged cationic functional group and with a negatively charged carboxylate group. The term "carboxybetaine-based" therefore refers to the compound containing carboxybetaine moieties.

As used herein, the term "zwitterionic" refers to neutral in electrical charge, which is balanced by a positive and a negative electrical charge.

As used herein, the term "lactone ring form" "cationic ring form" are used interchangeably to refers to a cyclic structure that has an ester bond and one group is positively charged.

As used herein, the term "hydrogel" refers to a material is a network of polymer chains that are hydrophilic and contain water as the dispersion medium.

As used herein, the term "elastomer" refers to is a material with viscoelasticity and very weak inter-molecular forces, generally having low Young's modulus and high failure strain compared with other materials.

It has been discovered that zwitterionic carboxybetaine with hydroxyl group(s) can switch between the cationic lactone (ring) form (antimicrobial) and the zwitterionic form (antifouling) and the intramolecular hydrogen bonds will enhance the mechanical property of the zwitterionic hydrogel. Under neutral or basic condition, these materials are in zwitterionic forms with ultralow-fouling property; under acidic conditions, they will automatically convert into cationic charged forms, which have antimicrobial ability. Bacteria can be trapped and killed through contact, then released under neutral or basic environment. This process is reversible (switchable) by simply changing the acidic/basic environment of the medium. Their ultra-antifouling property was tested by a surface plasmon resonance (SPR) sensor and the switchable ability was tested on the hydrogel surface. To the best of our knowledge, these switchable antimicrobial/antifouling and mechanically enhanced hydrogels are novel.

In one aspect, the present invention is directed to a zwitterionic polymer having excellent antifouling and antimicrobial properties and improved mechanical properties that comprises a polymer backbone and one or more zwitterionic carboxybetaine-based groups/moieties having at least one ethanol, propanol, butanol or pentanol group chemically bonded to the polymer backbone. In some embodiments, the polymers may be made from monomers having a switchable zwitterionic carboxybetaine-based group on one end of the molecule and a group such as an acrylate group capable of forming a polymer at another place in molecule. When these monomers are polymerized they form polymers having a polymer backbone and carboxybetaine-based side chains. The types of polymers formed by these materials are not particularly limited but must be capable of polymerizing in such a manner as to form a polymer backbone with one or more switchable zwitterionic carboxybetaine-based side chains. Four such polymers, by way of example, are poly(2-((2-hydroxyethyl)(2-(methacryloyloxy)ethyl)(methyl)ammonio)acetate)(pCBOH1) and poly(2-(bis(2-hydroxyethyl)(2-(methacryloyloxy)ethyl) ammonio)acetate)(pCBOH2), 2-((2-hydroxyethyl)(2-methacrylamidoethyl)(methyl)ammonio)acetate (CBMAA-1) and 3-((2-hydroxyethyl)(2-methacrylamidoethyl)(methyl) ammonio)propanoate (CBMAA-2).

The polymer backbone is preferably biocompatible, but need not be depending upon the particular use. Suitable polymer backbones include, without limitations polyacrylates. polymethacrylates, polyethylacrylates, polyacrylamides, polymethacrylamides, polyethylacrylamides, poly(2-hydroxyethyl methacrylate), polyserines, polyvinyl alcohols, polyols or any combinations thereof.

In at least some embodiments, the polymer backbone formed from the polymerization of zwitterionic carboxybetaine-based monomers backbone may be a polyacrylate, polymethacrylate, polyethylacrylate, polyacrylamide, polymethacrylamide or polyethylacrylamide, and is formed from a zwitterionic carboxybetaine-based monomers having the formula:

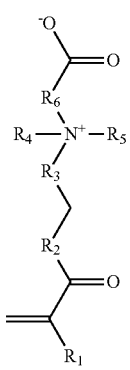

(XXXVI)

wherein $R_1$ is —H, —$CH_3$, or —$CH_2CH_3$, $R_2$ is O or NH; $R_3$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$, or —$CH_2CH_2CH_2CH_2CH_2OH$; $R_5$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

In some embodiments, the polymer backbone formed may be a polyacrylate, polymethacrylate, polyethylacrylate, polyacrylamide, polymethacrylamide or polyethylacrylamide and is formed from a zwitterionic carboxybetaine-based monomer having the formula:

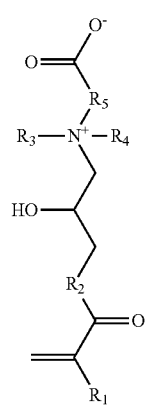

(XLII)

wherein $R_1$ is —H, —$CH_3$, —$CH_2CH_3$; $R_2$ is O or NH; $R_3$ is —$CH_2CH_2OH$, —$CH_2CH_2CH_2OH$, —$CH_2CH_2CH_2CH_2OH$, or —$CH_2CH_2CH_2CH_2CH_2OH$; $R_4$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2$ $CH_2OH$, or —$CH_2CH_2CH_2CH_2CH_2OH$; and $R_5$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

Suitable zwitterionic carboxybetaine-based monomers may include 2-((2-hydroxyethyl)(2-(methacryloyloxy)ethyl)ammonio)acetate, 2-((2-hydroxyethyl)(2-(methacryloyloxy)ethyl)(methyl)ammonio)acetate, 2-(bis(2-hydroxyethyl)(2-(methacryloyloxy)ethyl)ammonio)acetate, 2-((2-hydroxyethyl)(2-methacrylamidoethyl)ammonio)acetate, 2-(bis(2-hydroxyethyl)(2-methacrylamidoethyl)ammonio)acetate, 2-((2-hydroxyethyl)(2-methacrylamidoethyl)(methyl)ammonio)acetate, 3-((2-hydroxyethyl)(2-methacrylamidoethyl)(methyl)ammonio)propanoate, and combinations and analogs/derivatives thereof.

In some embodiments, the zwitterionic monomer may have one of the following formulas:

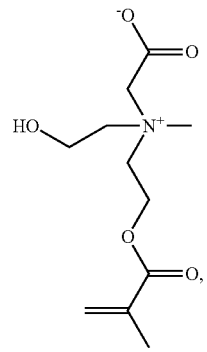

(XXXVIII)

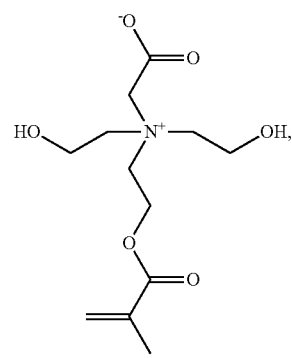

(XXXIX)

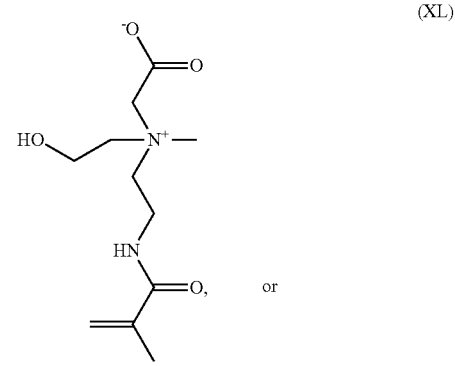

(XL)

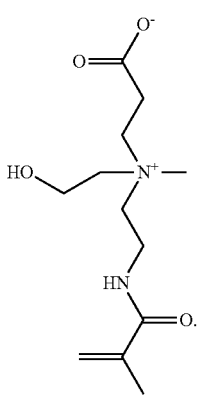

(XLI)

In some embodiments, the polymer backbone formed may be a polyacrylate, polymethacrylate, polyethylacrylate, polyacrylamide, polymethacrylamide or polyethylacrylamide and the polymer formed from zwitterionic carboxybetaine-based monomers has the formula:

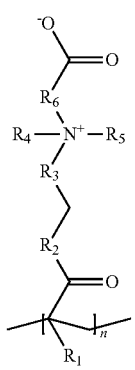

(X)

wherein $R_1$ is H, —$CH_3$ or —$CH_2CH_3$; $R_2$ are O or NH; $R_3$ is —$CH_2$—, —$CH_2CH_2$—, —$CH_2CH_2CH_2$—, —$CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$, or —$CH_2CH_2CH_2CH_2CH_2OH$; $R_1$ is H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$— and n is an integer from 2 to 10,000.

As set forth above, the carboxybetaine-based groups forming the zwitterionic side chains of the present invention will have a negatively charged deprotonated carboxyl group connected to a positively charged nitrogen atom. In some embodiments, the negatively charged deprotonated carboxyl group of the carboxybetaine-based groups forming the zwitterionic side chains of the of the present invention are connected by a chain of from about 1 to about 5 carbon atoms to the positively charged nitrogen atom. In some embodiments, the negatively charged deprotonated carboxyl group is connected by a chain of from about 2 to about 4 carbon atoms to the positively charged nitrogen atom. In some embodiments, the negatively charged deprotonated carboxyl group is connected by a single carbon atom to the positively charged nitrogen atom. It is found that one-carbon spacer between the negatively charged deprotonated carboxyl group and the positively charged nitrogen atom provides good switchability and stability in carboxybetaine-based materials.

These carboxybetaine-based groups also include at least one ethanol, propanol, butanol or pentanol group connected to the positively charged nitrogen atom. In some embodiments, there are two ethanol, propanol, butanol or pentanol groups connected to the positively charged nitrogen atom. In some embodiments, there is one ethanol, propanol, butanol or pentanol group and one methyl group connected to the positively charged nitrogen atom.

In some embodiments, the carboxybetaine-based groups may be connected to the polymer backbone through an ether or amide linkage. In some embodiments, the positively charged nitrogen atom is separated from the ether or amide linkage by a chain of from 1 to 5 carbon atoms. In some embodiments, the positively charged nitrogen atom is separated from the ether or amide linkage by a chain of from 2 to 3 carbon atoms. In some embodiments, the positively charged nitrogen atom is separated from the ether or amide linkage by a chain of 3 carbon atoms. In some of these embodiments, the second carbon atom from the positively charged nitrogen atom has a hydroxyl group bonded to it. In some embodiments, the positively charged nitrogen atom is separated from the ether or amide linkage by a chain of 2 carbon atoms.

While the carboxybetaine-based groups are linear and zwitterionic under neutral or basic conditions, it should be appreciated that under acidic conditions, these carboxybetaine-based groups undergo self-cyclization to form a corresponding cationic (lactone) ring form. Upon a return to neutral/basic conditions, the cationic ring form of these carboxybetaine-based groups undergo ring-opening and will return to its corresponding zwitterionic form. In some embodiments, the carboxybetaine groups are switchable in that they will repeatedly change back and forth between their linear zwitterionic and cationic ring forms with changes in the pH. See Scheme 1 below.

Scheme 1

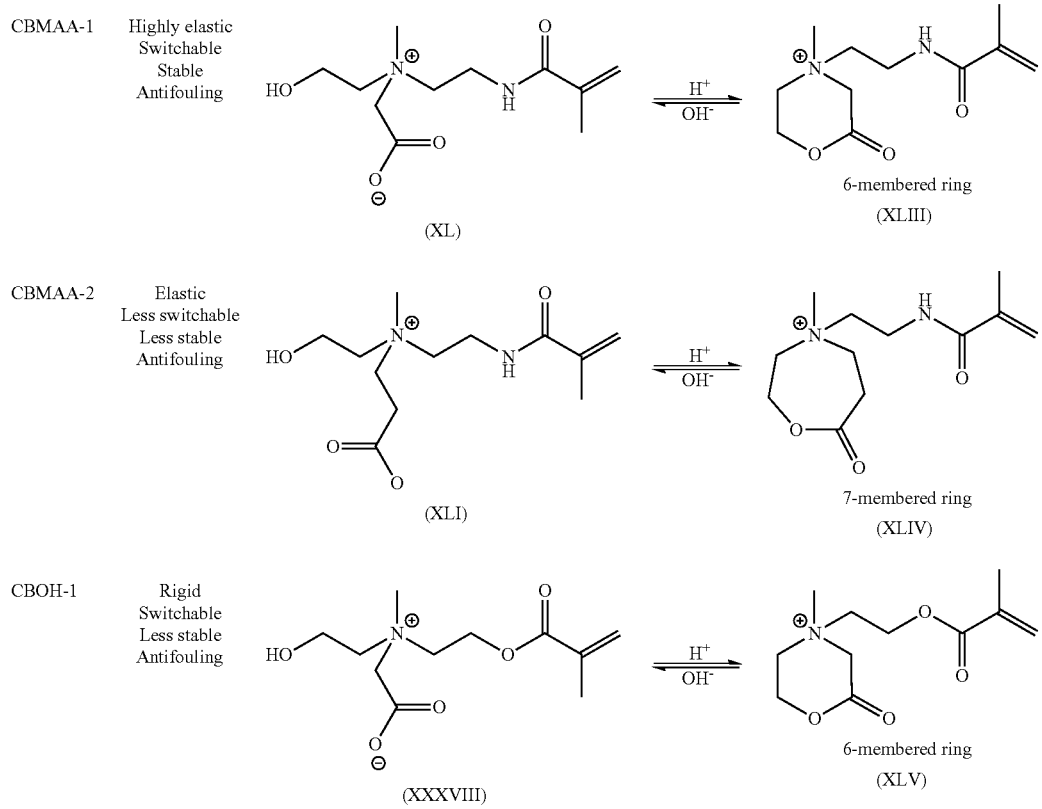

Cationic compounds, unlike antibiotics, kill bacterial cells via a nonspecific mechanism, so they are less likely to generate antibiotic-resistance and are particular useful for long-term antimicrobial applications such as chronic infection and burn wound treatments. The problem with conventional cationic materials, however, is that they are toxic due to their permanent positive charge. It is believed that these problems may be solved using the switchable antimicrobial and antifouling materials of embodiments of the present invention.

In some embodiments, the switchable zwitterionic carboxybetaine-based polymers of the present invention may be attached to a surface by any means known in the art for that purpose. In some of these embodiments, for example, the polymers may react with hydroxyl or amide groups to form ester or amide linkages. In some embodiments, the switchable zwitterionic carboxybetaine-based polymers of the present invention may be permanently attached to a surface by one or more covalent bonds. In some embodiments, the polymers may be functionalized to react with an appropriate substrate to form polymer-substrate linkage and then grafted from it. In some embodiments, polymerization is started from a surface immobilized self-assembled monolayer (SAM) as initiating sites. This approach has been found to produce polymer brushes with higher grafting density. See Example 7. In some embodiments, the polymerization process can be controlled through many well-defined initiation mechanisms, such as Atom-transfer Radical-polymerization (ATRP) and Reversible Addition Fragmentation Chain Transfer (RAFT) etc.

In some embodiments, the switchable zwitterionic carboxybetaine-based polymers of the present invention may be reversibly attached to a surface physical adsorption by first forming a co-polymer with a material known to have a strong interaction with the substrate surface. For example, the hydrophobic moiety in the carboxybetaine copolymer can attach to hydrophobic surfaces. In some embodiments, the carboxybetaine-based polymers of the present invention can form a co-polymer with a hydrophobic polymer. These hydrophobic polymers may include, but are not limited to, polyurethane, poly(methyl methacrylate), poly(tertbutyl methacrylate), polycaprolactone, polylactic acid, polylactic acid, poly(Lactide-co-Glycolide).

In another aspect, the present invention may be directed to a zwitterionic polymer having excellent antifouling and antimicrobial properties and improved mechanical properties that comprises a polymer backbone and one or more zwitterionic carboxybetaine-based groups/moieties having at least one ethanol, propanol, butanol or pentanol group chemically bonded to the polymer backbone as described above; and a linking compound.

In at least some embodiments, the carboxybetaine-based groups attached to the polymer chain may have the formula:

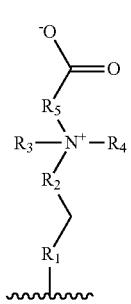

(XI)

wherein $R_1$ is O or NH; $R_2$ is —$CH_2$—, —$CH_2CH_2$—, —$CH_2CH_2CH_2$—, —$CH_2CH_2CH_2CH_2$—, or —$CH_2$ $CH_2CH_2CH_2$—; $R_3$ is —$CH_2CH_2OH$, —$CH_2CH_2CH_2OH$, —$CH_2CH_2CH_2CH_2OH$, or —$CH_2CH_2CH_2CH_2CH_2OH$; $R_4$ is H, —$CH_3$, $CH_2CH_3$, —$CH_2CH_2CH_3$, —$CH_2CH_2$ $CH_2CH_3$, —$CH_2CH_2OH$, —$CH_2CH_2CH_2OH$, —$CH_2CH_2$ $CH_2CH_2OH$, —$CH_2CH_2CH_2CH_2CH_2OH$; $R_5$ is —$CH_2$—, —$CH_2CH_2$—, —$CH_2CH_2CH_2$—, —$CH_2CH_2CH_2CH_2$—, or —$CH_2CH_2CH_2CH_2CH_2$— and ⁓ is the polymer backbone.

In some embodiments, the carboxybetaine-based groups attached to the polymer chain may have the formula:

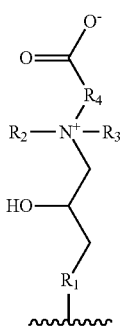

(XII)

wherein $R_1$ is O or NH; $R_2$ is —$CH_2CH_2OH$, —$CH_2CH_2CH_2OH$, —$CH_2CH_2CH_2CH_2OH$, or —$CH_2$ $CH_2CH_2CH_2CH_2OH$; $R_3$ is H, —$CH_3$, $CH_2CH_3$, —$CH_2$ $CH_2CH_3$, —$CH_2CH_2CH_2CH_3$, —$CH_2CH_2OH$, —$CH_2CH_2$ $CH_2OH$, —$CH_2CH_2CH_2CH_2OH$, or —$CH_2CH_2CH_2$ $CH_2CH_2OH$, $R_4$ is —$CH_2$-, —$CH_2CH_2$—, —$CH_2CH_2$ $CH_2$—, —$CH_2CH_2CH_2CH_2$—, or —$CH_2CH_2CH_2$ $CH_2CH_2$—; and ⁓ is the polymer backbone.

In at least some embodiments, the carboxybetaine-based groups attached to the polymer chain may have the formula:

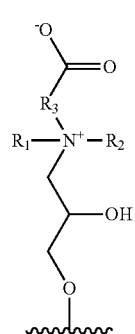

(XIII)

wherein $R_1$ is —$CH_2CH_2OH$, —$CH_2CH_2CH_2OH$, —$CH_2$ $CH_2CH_2CH_2OH$, or —$CH_2CH_2CH_2CH_2CH_2OH$; $R_2$ is —H, —$CH_3$, —$CH_2CH_3$, —$CH_2CH_2CH_3$, —$CH_2CH_2CH_2$ $CH_3$, —$CH_2CH_2OH$, —$CH_2CH_2CH_2OH$, —$CH_2CH_2CH_2$ $CH_2OH$, or —$CH_2CH_2CH_2CH_2CH_2OH$; R3 is —$CH_2$—, —$CH_2CH_2$—, —$CH_2CH_2CH_2$—, —$CH_2CH_2CH_2CH_2$—, or —$CH_2CH_2CH_2CH_2CH_2$—; and ⁓ is the polymer backbone.

In some embodiments, the carboxybetaine-based groups attached to the polymer chain may have the formula of:

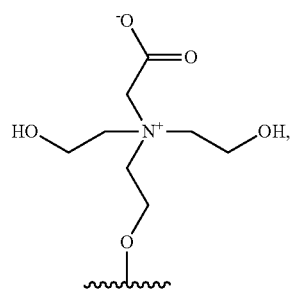

(II)

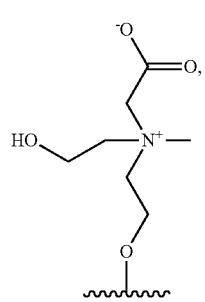

(II)

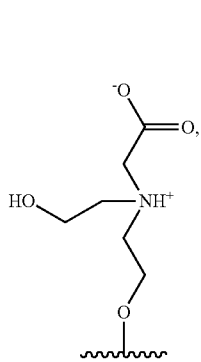

(III)

(IV)
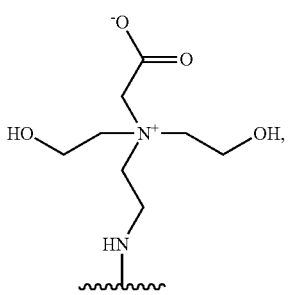

(V)
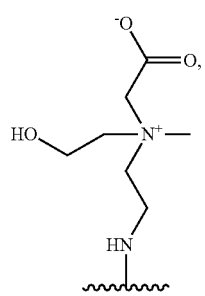

(VI)
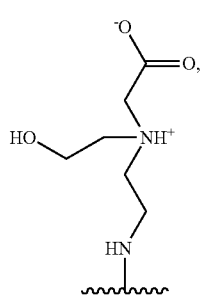

(VII)
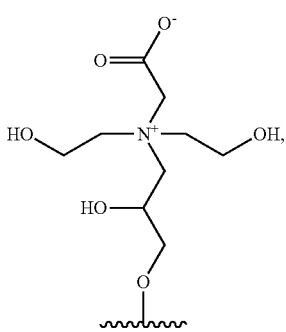

(VIII)
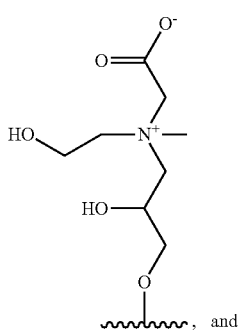, and (IX)
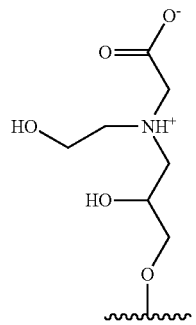

wherein ∿∿ is the polymer backbone.

Figure 1B:
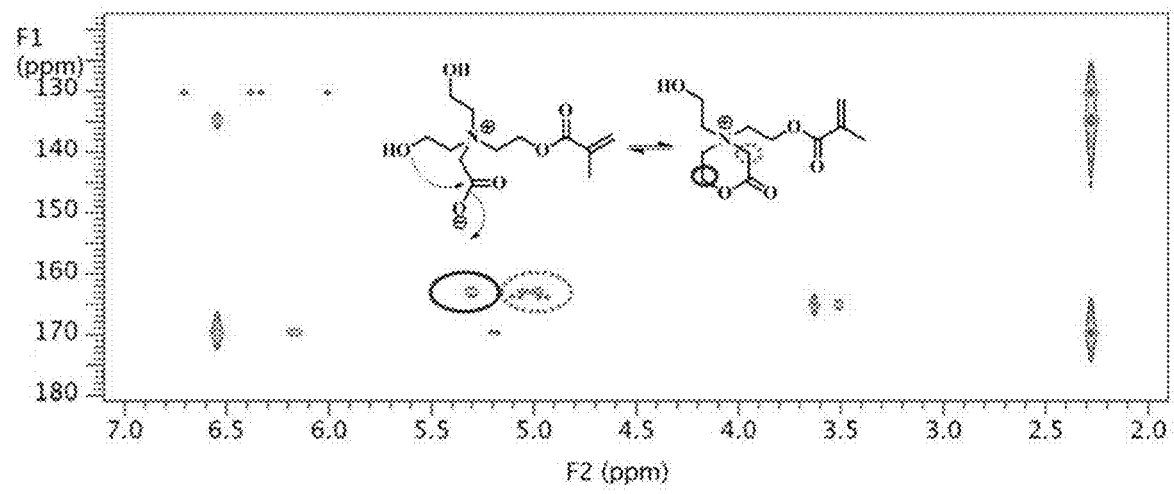

As set forth above, under acidic conditions, the zwitterionic carboxybetaine-based groups undergo self-cyclization to form a corresponding cationic (lactone) ring form and can catch and kill bacteria. See Scheme 1, above. $^1$H, $^{13}$C NMR data and heteronuclear multiple-bond correlation (gHMBC) two dimensional (2D) NMR spectrum, which provides two- and three-bond correlations between $^1$H and $^{13}$C, were used to confirm the ring structure formation of the carboxybetaine-based monomers (CBOH1 and CBOH2) in deuterated trifluoroacetic acid (TFA-d). The crosspeak in solid circle shown in the 2D NMR spectrum FIG. 1A is the three-bond correlation between the resonances of the methylene protons adjacent to hydroxyl group of a first carboxybetaine-based monomer (CBOH1) and the resonances of the carbon on negatively charged carboxylate. This is the solid evidence of ring formation. It should be noted that, after cyclization, the protons from ethylene group in dotted circle change from a single peak into a doublet of doublet. A similar correlation for a second carboxybetaine-based monomer (CBOH2) is shown in FIG. 1B.

The kinetics of lactone ring formation was monitored by $^1$H NMR at different time points. It is known that a 2-morpholinone ring can be obtained in both strong and weak acids, and will hydrolyze into zwitterionic form in basic and physiological condition (PH 7.3). To study the ring formation, two carboxybetaine-based monomers according to at least some embodiments of the present invention (CBOH1 and CBOH2) were dissolved in deuterated trifluoroacetic acid (TFA-d) and deuterated acetic acid (HAc-d) at a concentration of 0.2 M, respectively. Both vinylic protons showed downfield shift after ring formation. (See FIGS. 2A, 2B) Conversion was calculated based on the ratio of vinylic protons from each form.

Figure 2A:
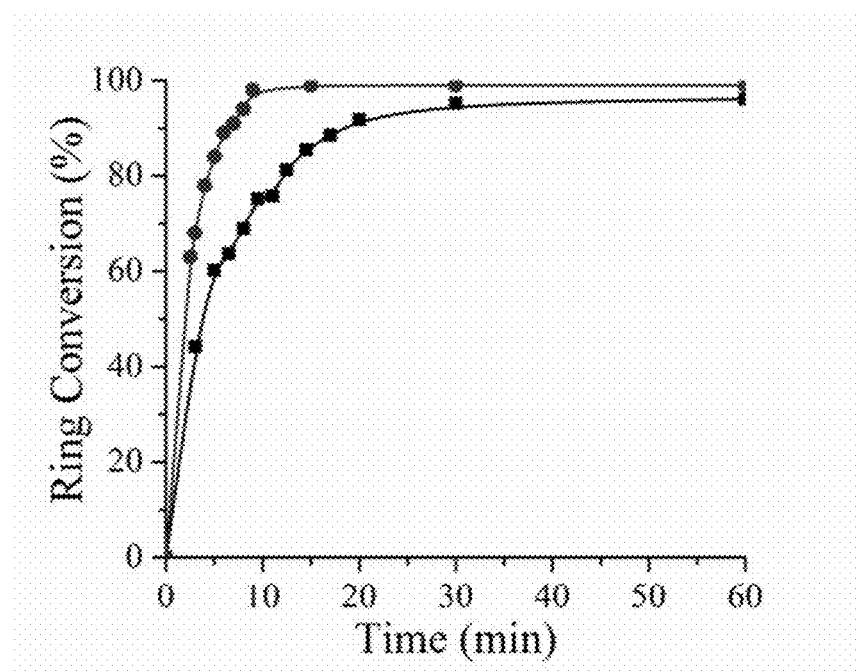
FIG. 2A-B are graphs showing the conversion kinetics of zwitterionic CBOH1 (squares) and CBOH2 (round dots) to their cationic ring form in TFA-d (2A) and HAc-d (2B).
Figure 2B:
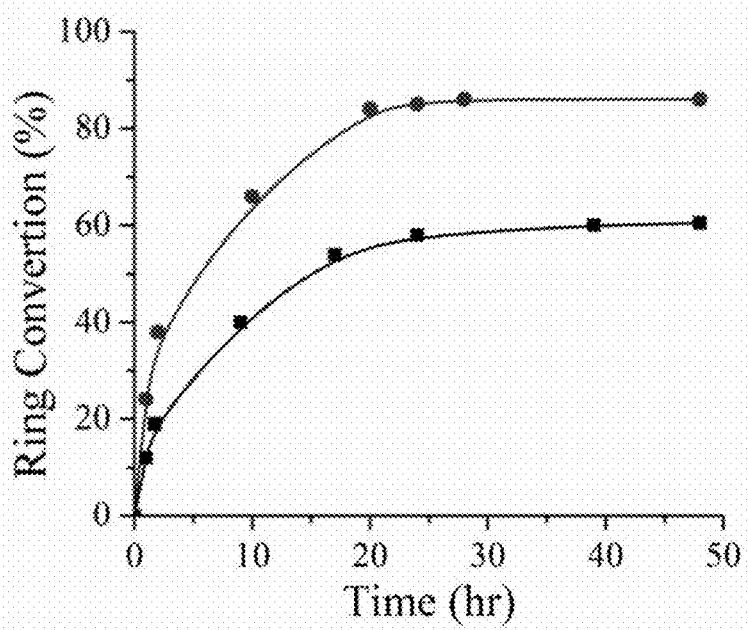

As shown in FIG. 2A, 96% of CBOH1 was converted in to the ring form in TFA within an hour, and for CBOH2 the conversion was 99% within 15 minutes. In acetic acid, (FIG. 2B) CBOH1 and CBOH2 were able to reach 55% and 84% conversion within 20 hours, respectively. In both cases, the sterically favored ring structure of these carboxybetaine-based monomers was found to provide better sensitivity to the stimuli from acidic environment compared with previously reported carboxybetaine-based monomers. The results indicated that CBOH2 structure is more favorable for lactone ring formation than CBOH1 under the same condition. The symmetrically substituted CBOH2 is cyclizable on either side, which gives it a better chance to react with the carbonyl group and result in a much faster response for ring formation.

Besides the pH of a bulk solution, the kinetics of ring formation and ring indicate in the hydrogels of embodiments of the present invention are also affected by the local pH and the steric hindrance of polymer backbone and side chains. The formation of one lactone ring consumes one proton. The consumption of protons subsequently leads to the increase of the local pH and slow down the ring formation, but the effect will not be dramatic. Since zwitterionic/cationic hydrogels have very high water contents and high porous structures, ions in the hydrogel can reach the equilibrium with bulk solution within a few minutes or less.

In some embodiments, the carboxybetaine-based groups of the present invention may have the following cationic ring form:

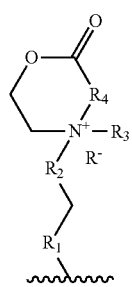

(XIV)

wherein $R_1$ is O or NH; $R_2$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_3$ is —H, —$CH_3$, —$CH_2CH_3$, —$CH_2CH_2CH_3$, —$CH_2CH_2CH_2CH_3$, $CH_2CH_2OH$, —$CH_2CH_2CH_2OH$, —$CH_2CH_2CH_2CH_2OH$, —$CH_2CH_2CH_2CH_2CH_2OH$; $R_4$ is —$CH_2$—, —$CH_2CH_2$—, —$CH_2CH_2CH_2$—, —$CH_2CH_2CH_2CH_2$—, —$CH_2CH_2CH_2CH_2CH_2$—; $R^-$ is any organic or inorganic anion; and ~~~ is the polymer backbone.

In some embodiments, the carboxybetaine-based groups of the present invention may have the following cationic ring form:

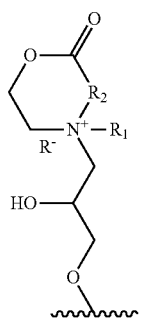

(XV)

wherein $R_1$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; $R_2$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R^-$ is any organic or inorganic anion; and ~~~ is the polymer backbone.

In some embodiments, the carboxybetaine-based groups of the present invention may have one or more of the following cationic ring forms:

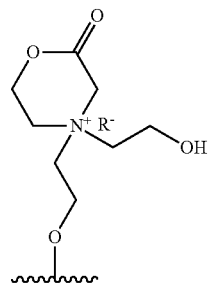

(XVI)

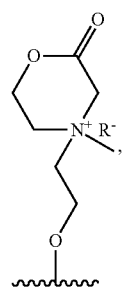

(XVII)

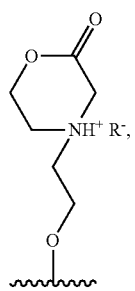

(XVIII)

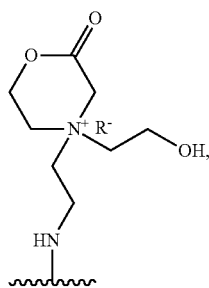

(XIX)

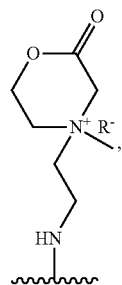

(XX)

-continued
(XXI)
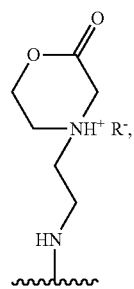
(XXII)
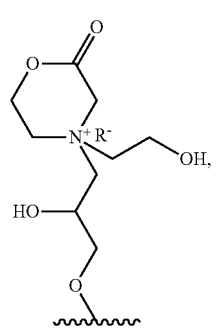
(XXIII)
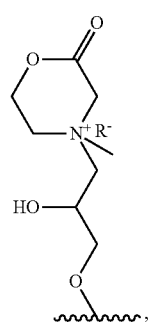
(XXIV)
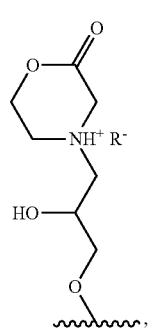
(XXV)
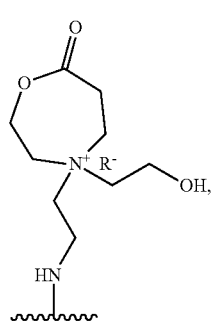
(XXVI)
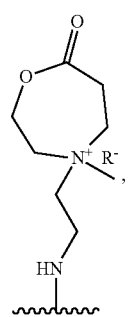
(XXVII)
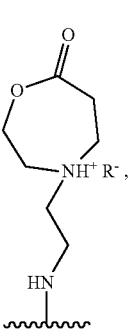
(XXVIII)
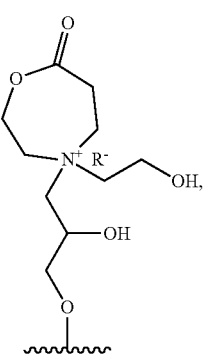
(XXIX)
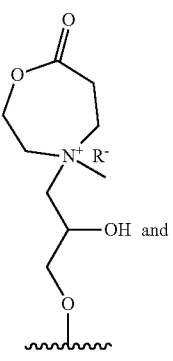

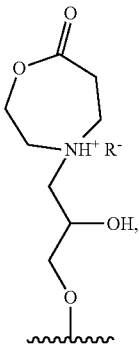

(XXX)

wherein R⁻ is any organic or inorganic anion and ⌇⌇⌇ is the polymer backbone.

Figure 3:
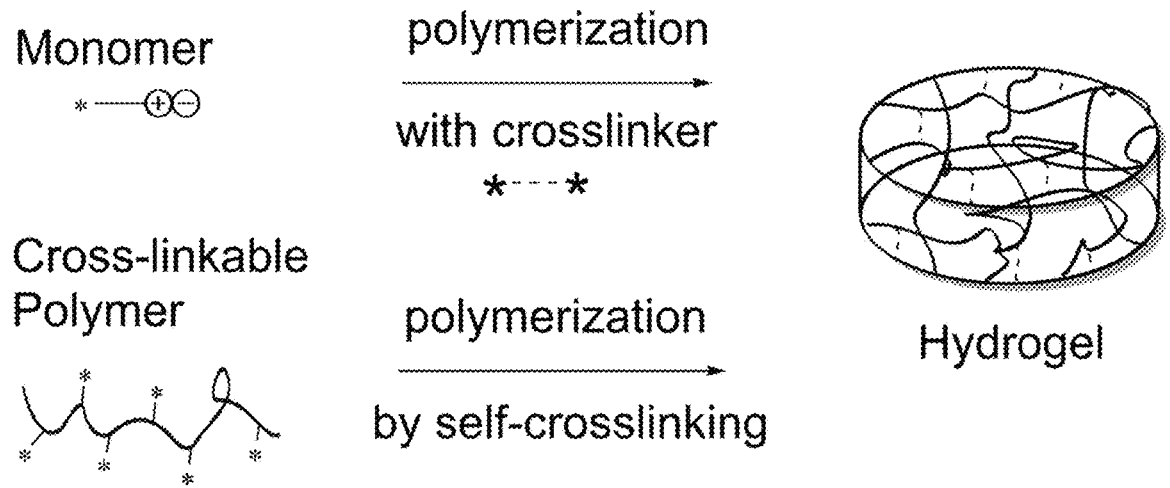
FIG. 3 is a schematic representation of a hydrogel according to at least one embodiment of the present invention.

In some embodiments, these polymers are crosslinked to form a hydrogel or an elastomer as shown in FIG. 3. The crosslinking compound is not particularly limited provided that it is bi- or multi-functional and able to link to the polymer chain and/or the carboxybetaine-based groups that form the side chains of the polymer. In some embodiments, the crosslinking compounds may bind with the polymer chains. In some embodiments, the crosslinking compounds may bind to hydroxyl groups on the carboxybetaine-based groups that form the side chains of the polymer. Suitable crosslinking compounds may include di(methyl)acrylates, multi-(methyl)acrylates, di(methyl)acrylamides, multi-(methyl)acrylamides, diepoxide multi-epoxides, dithiols and multi-thiols carboxybetaine di(methyl)acrylate, carboxybetaine di(methyl)acrylamide, poly(ethylene glycol) di(methyl)acrylate, 1,3-Propanedithiol, 1,4-Butanedithiol, 1,3-Butadiene diepoxide, and combinations and/or analogs thereof.

One of ordinary skill will know how to crosslink the above described zwitterionic polymers using the crosslinking compounds described above, without undue experimentation.

In some embodiments, the crosslinking compound may have the formula:

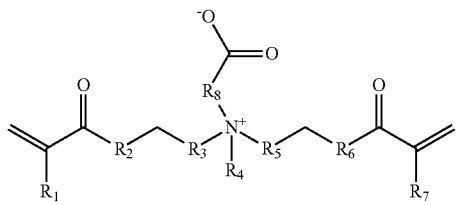

(XXXI)

wherein $R_1$ and $R_7$ are —H, —CH$_3$, or —CH$_2$CH$_3$; $R_2$ and $R_6$ are O or NH; $R_3$ and $R_5$ are —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—; $R_4$ is —H, CH$_3$, CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and $R_8$ is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—.

In some embodiments, the crosslinking compound may have the formula:

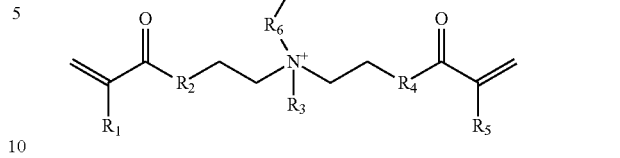

(XXXIII)

wherein $R_1$ and $R_5$ are H, —CH$_3$, or —CH$_2$CH$_3$; $R_2$ and $R_4$ are O or NH; $R_3$ is H, —CH$_3$, —CH$_2$CH$_3$, —CH$_2$CH$_2$OH, —CH$_2$CH$_2$O—COCH=CH$_2$, —CH$_2$CH$_2$O—COC(CH$_3$)=CH$_2$, —CH$_2$CH$_2$NH—COCH=CH$_2$, or —CH$_2$CH$_2$NH—COC(CH$_3$)=CH$_2$ and $R_6$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—.

In some embodiments, the crosslinking compound may have the formula:

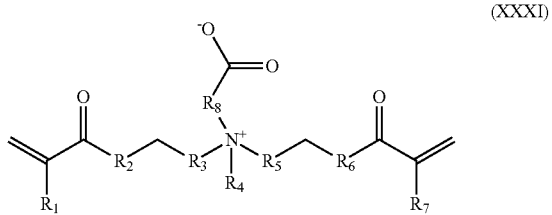

(XXXI)

wherein $R_1$ and $R_7$ are —H, —CH$_3$, or —CH$_2$CH$_3$; $R_2$ and $R_6$ are O or NH; $R_3$ and $R_5$ are —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—; $R_4$ is —H, CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and $R_8$ is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—.

In some embodiments, the crosslinking compound may have the formula:

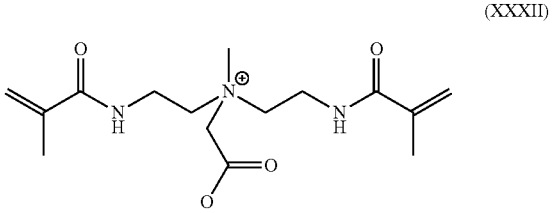

(XXXII)

A representative reaction scheme for synthesizing compound (XXXII) (2-(bis(2-methacrylamidoethyl)(methyl)ammonio)acetate) is shown in Scheme 8 and described in Example 24. In some embodiments, compound XXXII may be synthesized by: dissolving a base in a suitable solvent and adding diethylenetriamine (compound XL); cooling the product of that reaction and reacting it with a stoichiometric quantity of methacrylic anhydride under a dry gas atmosphere to produce N,N'-(azanediylbis(ethane-2,1-diyl))bis(2-methylacrylamide)(compound LXVI); dissolving the N,N'-(azanediylbis(ethane-2,1-diyl))bis(2-methylacrylamide)(compound LXVI) in a suitable organic solvent and reacting it with tert-butyl bromoacetate to produce tert-butyl bis(2-methacrylamidoethyl)glycinate (3); dissolving the reaction product of step C in a suitable solvent and reacting it with methyl iodide under a dry gas atmosphere; reacting the product of step D with trifloroacetic acid (TFA) in a suitable solvent and collecting the reaction product; and re-dissolving the reaction product of step E in suitable solvent and neutralizing it over a baic ionic exchange resin to produce form 2-(bis(2-methacrylamidoethyl)(methyl)ammonio)acetate (compound XXXII)

In some embodiments, hydrogels according to the present invention may have an equilibrium water content (EWC) of more than 30% of the polymer by weight. In some embodiments, hydrogels according to the present invention may have an equilibrium water content (EWC) of from about 30% to about 99.9% of the polymer by weight. In some embodiments, hydrogels according to the present invention may have an equilibrium water content (EWC) of from about 50% to about 99.9% of the polymer by weight. In some embodiments, hydrogels according to the present invention may have an equilibrium water content (EWC) of from about 75% to about 99% of the polymer by weight. In some embodiments, hydrogels according to the present invention may have an equilibrium water content (EWC) of from about 80% to about 98% of the polymer by weight.

As set forth above, another problem with existing zwitterionic materials is that they are relatively fragile and not stretchable. This significantly limits their utility for flexible medical devices (such as heart valve, implantable biosensors, and tissue scaffolds) which require implanted materials to be elastic and fouling-resistant.

Accordingly, in another aspect the present invention is directed to novel zwitterionic monomers having excellent elasticity, stability, antimicrobial and antifouling properties. In has been found that the properties of zwitterionic materials can be accurately tuned at the monomer level. It is believed that this all-in-one material will significantly broaden the application spectrum of zwitterionic materials. To the best of our knowledge, these all-in-one zwitterionic monomers are novel.

Tunable mechanical properties of biomaterials are highly desired, since the requirements for mechanical properties of materials vary dramatically for different applications. And as set forth above, the existing zwitterionic materials lack elasticity. It has been found that use of a polymer backbone that is more hydrophilic and has stronger hydrogen bond forming groups, will make the resulting material softer and more elastic. Crosslinking density can be adjusted to obtain a moderate EWC and optimum elasticity. To the best of our knowledge, no pure zwitterionic material with such a good elastic property has ever been reported.

In some embodiments, the present invention is directed to a carboxybetaine elastomer composition comprising poly(2-((2-hydroxyethyl)(2-methacrylamidoethyl)(methyl)ammonio)acetate), poly(3-((2-hydroxyethyl)(2-methacrylamidoethyl)(methyl)ammonio)propanoate), poly(2-((2-hydroxyethyl) (2-(methacryloyloxy)ethyl)(methyl)ammonio)acetate) and poly(2-(bis(2-hydroxyethyl)(2-(methacryloyloxy)ethyl)ammonio)acetate) and combinations and/or analogs thereof and a crosslinker.

Figure 4A:
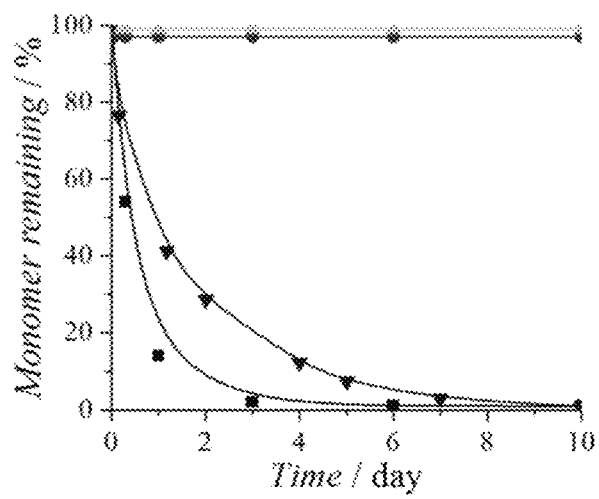
FIG. 4A-C are graphs showing the stability of quaternary ammonium in pure HAc (4A) and in 0.2 M $NaCO_3$ (4B), and the stability of methacrylate and methacrylamide backbone in 0.2 M $Na_2CO_3$ (4C) of CBMAA-1 (triangles), CBMAA-2 (half circles), CBOH-1 (circles) and CBMA-2 (squares) monomers. Note that straight lines were slightly shifted for clarity. The data was calculated from integral values of the corresponding peaks in NMR spectra.
Figure 4B:
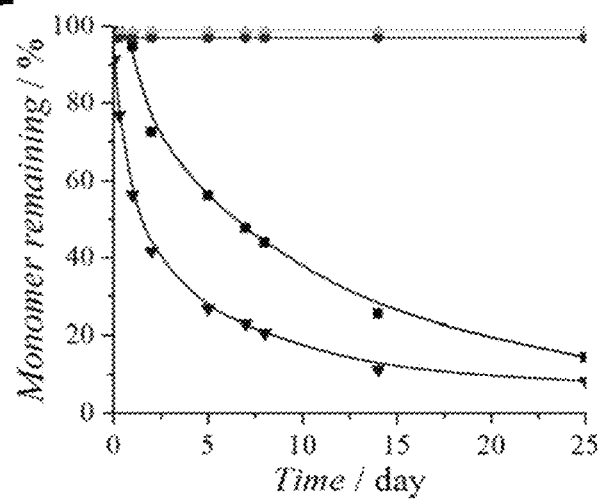
Figure 4C:
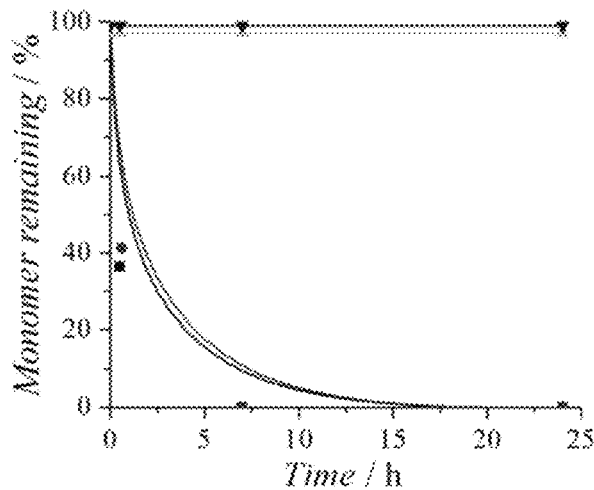

In some embodiments, a methacrylamide polymer backbone is used since as will appreciated by those of skill in the art, amide bonds are more stable than ester bonds under both acidic and basic conditions. FIG. 4C is a graph showing hydrolysis of CBMA-2, CBOH1, CBMAA-1, and CBMAA-2 over time. As can be seen from FIG. 4C, the methacrylamide group is highly resistant to hydrolysis under basic conditions.

In some embodiments, the carboxybetaine-based monomers of the present invention may be synthesized using a three-step reaction as shown in Scheme 2, below.

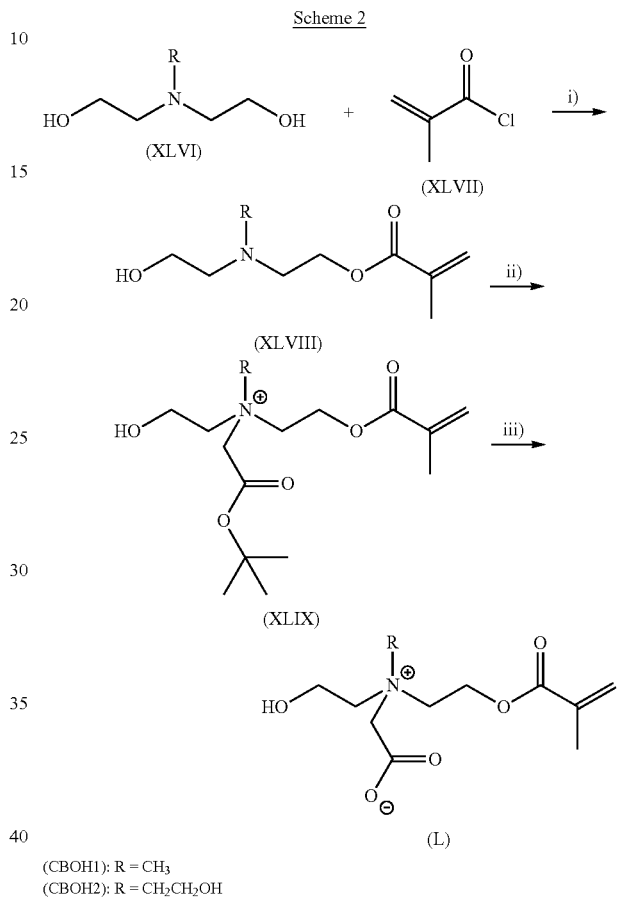

Scheme 2

(CBOH1): R = CH₃
(CBOH2): R = CH₂CH₂OH

Reaction conditions for Scheme 2 are as follows. First, compound XLVI is dissolved in an anhydrous organic solvent such as anhydrous tetrahydrofuran and an anhydrous base such as sodium carbonate is added. One of ordinary skill will be able to select an appropriate anhydrous organic solvent and anhydrous base without undue experimentation. The solution is then cooled and reacted with methacryloyl chloride (XLVII) to form compound XLVIII In some embodiments, compound XLVIII is 2-((2-hydroxyethyl)(methyl)amino)ethyl methacrylate. The method of cooling the solution is not particularly limited and is well within the capabilities of one of skill in the art. In some embodiments, the solution may be cooled in an ice bath. Compound XLIII is then dried and purified according to methods known in the art for that purpose.

Next, compound XLVIII may be dissolved in an organic solvent such as acetonitrile and reacted with tert-butyl bromoacetate at a temperature of from about 40° C. and 150° C. to form compound XLIX. In some embodiments, compound XLIX is 2-(tert-butoxy)-N-(2-hydroxyethyl)-N-(2-methacryloyloxy)ethyl)-N-methyl-2-oxoethanaminium bromide. One of ordinary skill will be able to select an appropriate organic solvent without undue experimentation.

In some embodiments, the reaction temperature is from about 40° C. to 110° C. In some embodiments, the reaction temperature is from about 50° C. to 80° C. In some embodiments, the reaction temperature is from about 50° C. to 70° C. In some embodiments, the reaction temperature is about 60° C. Compound XLIX is then dried and purified according to methods known in the art for that purpose.

Last, compound XLIX may be combined with trifluoroacetic acid (TFA) and an organic solvent such as dichloromethane to remove the tert butyl group of compound XLIX. The resulting compound may be precipitated out and dried according to methods known in the art for that purpose. It is then redissolved in an organic solvent and neutralized over a basic ion exchange resin to form compound 4. One of ordinary skill in the art will be able to select a basic ion exchange resin without undue experimentation. Compound L may then be dried and purified according to any methods known in the art for that purpose.

In some embodiments, R is $CH_3$ and the resulting molecules is 2-((2-hydroxyethyl)(2-(methacryloyloxy)ethyl)(methyl)ammonio)acetate)(CBOH1). In some embodiments, R is $CH_2CH_2OH$ and the resulting molecules is poly(2-(bis(2-hydroxyethyl)(2-(methacryloyloxy)ethyl)ammonio)acetate)(pCBOH2). In some embodiments, CBOH1 and CBOH2 may be synthesized as set forth in Examples 1 and 2.

In some embodiments, the novel zwitterionic monomers of the present invention may be synthesized via the three-step reaction a shown in Scheme 3, and described in more detail in Example 14.

First, an organic or inorganic base, such as NaOH, is dissolved in water and/or a water miscible organic solvent such as methanol and 2-((2-aminoethyl)amino)ethanol (compound LI) is added. The resulting mixture is cooled to about 0° C. and reacted with methacrylic anhydride (LII) under nitrogen protection to produce N-(2-((2-hydroxyethyl)amino)ethyl)methacrylamide (LIII)

Next, compound LIII is dissolved in ethanol or any suitable organic solvent and reacted with either tert-butyl bromoacetate or tert-butyl acrylate at a temperature of from about 40° C. and 150° C. to form tert-butyl N-(2-hydroxyethyl)-N-(2-methacrylamidoethyl)glycinate or tert-butyl 3-((2-hydroxyethyl)(2-methacrylamidoethyl)amino)propanoate. In some embodiments, the reaction temperature is from about 40° C. to 110° C. In some embodiments, the reaction temperature is from about 50° C. to 80° C. In some embodiments, the reaction temperature is from about 50° C. to 70° C. In some embodiments, the reaction temperature is about 60° C. Compound LIV or LV is then dried and purified according to methods known in the art for that purpose.

Last, compounds LIV or LV is dissolved in an organic solvent such as acetonitrile, and reacted with methyl iodide at a temperature of from about from about 40° C. and 150° C. under a nitrogen atmosphere. In some embodiments, the reaction temperature is from about 40° C. to 110° C. In some embodiments, the reaction temperature is from about 50° C. to 80° C. In some embodiments, the reaction temperature is from about 50° C. to 70° C. In some embodiments, the reaction temperature is about 60° C. The resulting mixture may then be combined with trifluoroacetic acid (TFA) and Scheme 3

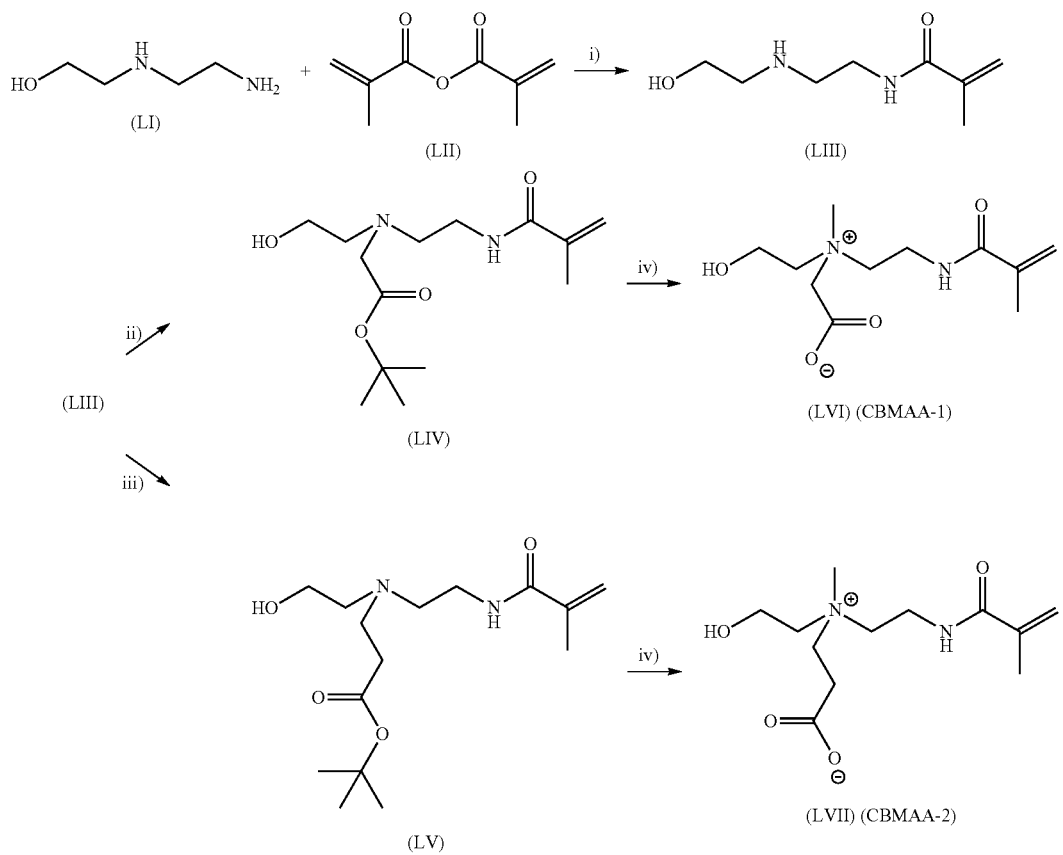

an organic solvent such as dichloromethane to remove the tert butyl group of compound LIV or LV. The resulting compound may be precipitated out and dried according to methods known in the art for that purpose. It may then be redissolved in an organic solvent and neutralized over a basic ion exchange resin to form to form 2-((2-hydroxyethyl)(2-methacrylamidoethyl)(methyl)ammonio)acetate (compound LVI) or 3-((2-hydroxyethyl)(2-methacrylamidoethyl)(methyl)ammonio)propanoate (compound LVII). One of ordinary skill in the art will be able to select an ion exchange resin without undue experimentation. Compound LVI or LVII is then dried and purified according to methods known in the art for that purpose.

In many biofouling processes, limiting protein adsorption on a surface is the initial but critical step. This is particularly true in the field of biomedicine, since these materials often contact blood or other body fluids. Adsorbed proteins can facilitate the attachment and accumulation of bacteria or cells from the immune system and cause infection or inflammation, which subsequently leads to the foreign body response and cause the failure of implanted devices or materials. Beside the surface chemistry, protein adsorption on surfaces can be affected by many factors, including surface packing density, surface roughness, and surface thickness.

To minimize the effect of surface packing density and surface roughness and evaluate the intrinsic antifouling properties of the material, the antifouling properties of pCBOH1 and pCBOH2 were evaluated on the polymer brush surfaces via surface initiated atom transfer radical polymerization (si-ATRP) method. si-ATRP method has been widely used to prepare high packing, well-defined and uniform surfaces.

Figure 5A:
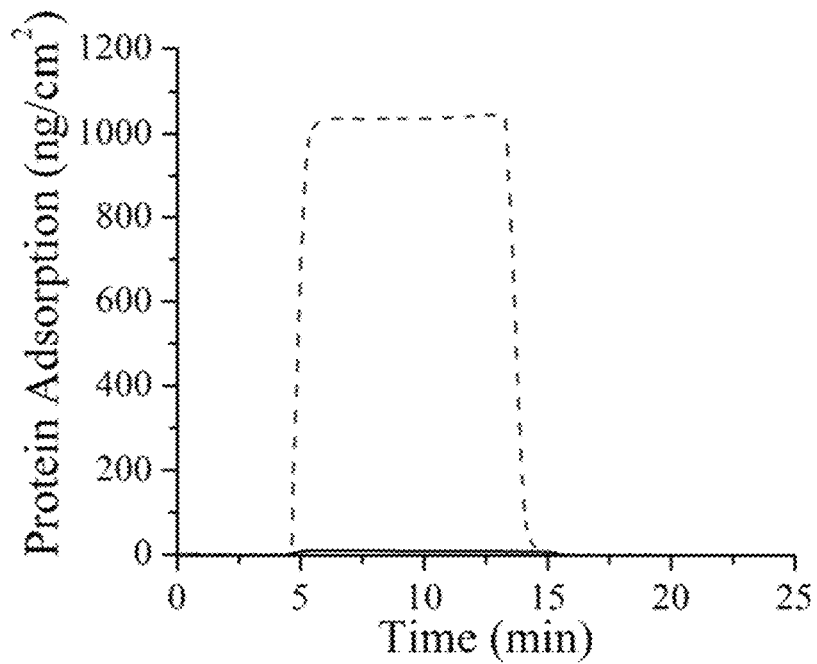
FIG. 5A-B are SPR sensorgrams showing ultra-low fouling properties of zwitterionic pCBOH1 (5A) and pCBOH2 (5B) polymer brushes against 1 mg mL$^{-1}$ fibrinogen (solid line) and undiluted human plasma (dash line).
Figure 5B:
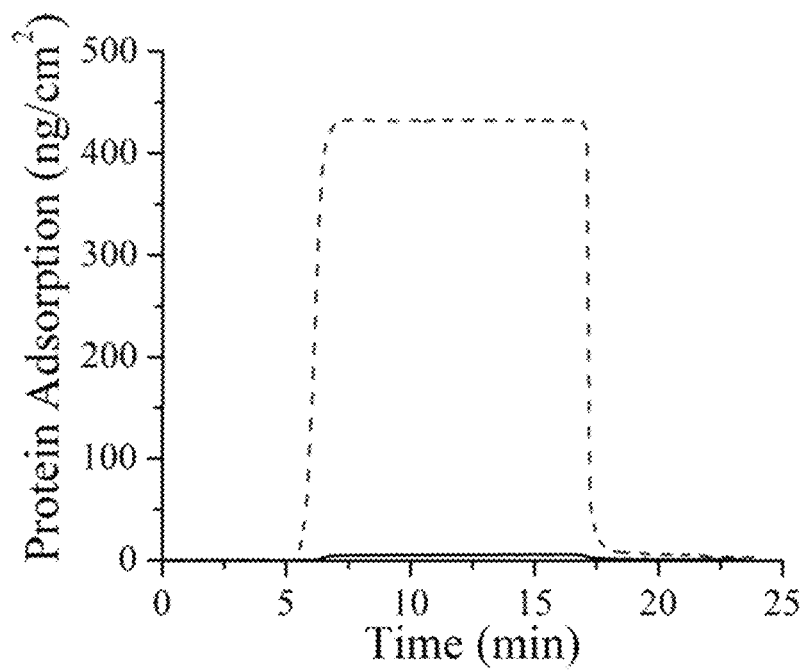
Figure 6:
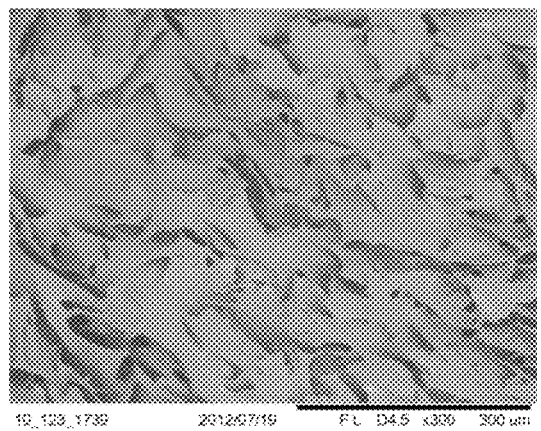
FIG. 6A-F are SEM images of the cross-section from 3M hydrogels after freeze-drying: pCBOH1 (6A) and (6D), pCBOH2 (6B) and (6E), and pCBMA (6C) and (6F) at different resolutions. (scale bars: 6A-C 300 μm, 6D-F 30 μm.)
Figure 6:
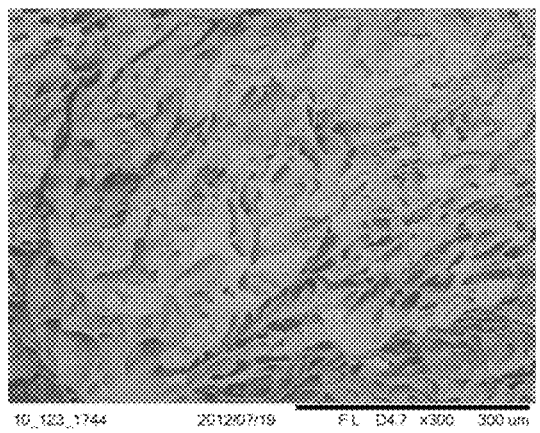
Figure 6:
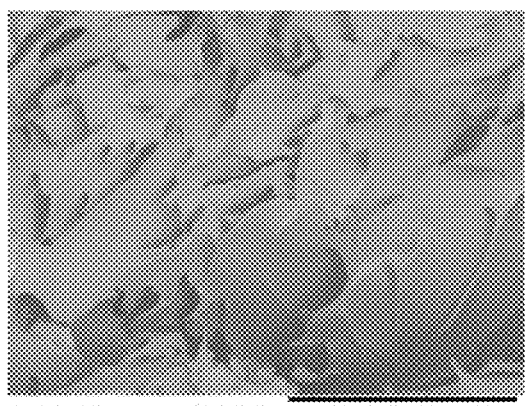
Figure 6:
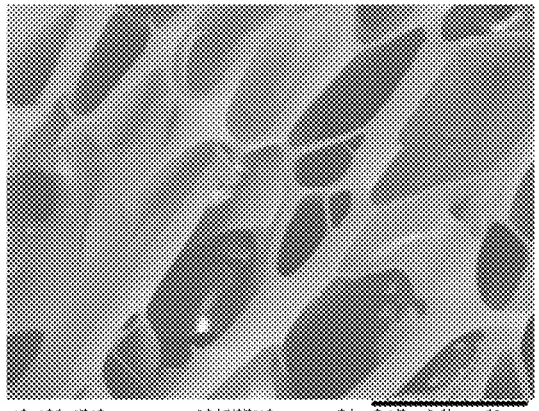
Figure 6:
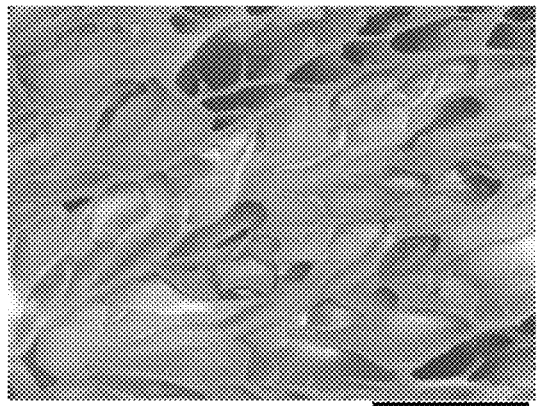
Figure 6:
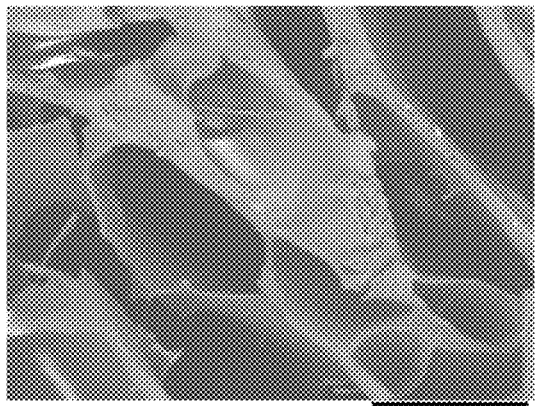

The protein-resistant properties of pCBOH1 and pCBOH2 polymer brushes were characterized by SPR on gold-coated sensor chips using a single protein solution (1 mg mL$^{-1}$ bovine fibrinogen) and a complex solution (100% human blood plasma). As shown in FIG. 5A, 5B, both materials were highly resistant to the adsorption of both fibrinogen (0.8 ng cm$^{-2}$ for pCBOH2 and <0.3 ng cm$^{-2}$ (detection limit of the sensor) for pCBOH1) and 100% human blood plasma (0.2 ng cm$^{-2}$ for pCBOH1 and 2.4 ng cm$^{-2}$ for pCBOH2). It is well understood in the art that materials contacting blood with less than 5 ng cm$^{-2}$ fibrinogen adsorption can delay the blood coagulation caused by platelet activation. Protein adsorption values on both pCBOH1 and pCBOH2 surfaces were below the criteria for ultralow fouling materials.

Results from both experiments and molecular dynamic simulation suggest that the hydration of a surface plays a key role to resist protein adsorption. Zwitterionic materials bind water through their carboxylate anions and quaternary ammonium cations via ionic solvation. For zwitterionic materials, the increase of the film thickness will lead to an increased intramolecular charge-charge interaction which will reduced the hydration of the surface and compromise its antifouling properties. In some embodiments, the film thickness of the polymer brushes can be controlled by adjusting reaction time and monomer concentration. The film thickness was measured by SPR as ~13 nm for pCBOH1 and ~26 nm for pCBOH2. In CBOH1 and CBOH2, hydroxyl groups are linked to quaternary ammonium cation. The substitution of methyl group of quaternary ammonium cation with a larger group will change the hydration of quaternary ammonium cation and affect the antifouling properties of the zwitterionic materials. It has been found that the loss of the hydration of quaternary ammonium in CBOH1 and CBOH2 can be countered by the hydrophilic hydroxyl group(s) in a hydroxymethyl, hydroxyethyl, hydroxypropyl, hydroxybutyl, and/or hydroxypentyl substitution group. Additionally, SPR and bacterial attachment experiments show that the introduction of the hydroxyl groups did not compromise their antifouling properties of the zwitterionic polymers.

It is known that positively charged polymers or small molecule compounds can interrupt the membrane integrity of negatively charged microorganisms and lead to the death of the cells. Permanent cationic materials can kill attached bacterial cells, but killed cells and their debris remain on the surface that can trigger the inflammation. Permanent cationic materials also have poor biocompatibility due to the high protein adsorption. The switchable antimicrobial and antifouling hydrogels of at least some embodiments of the present invention can be used to address these issues.

As set forth above, the utility of known zwitterionic hydrogels has been limited due to their unsatisfactory mechanical properties. It has been found that the mechanical properties of zwitterionic materials can be improved by incorporating hydrogen bond forming groups into the molecular structure.

To study the internal morphology of the polymeric networks of the present invention, the cross-section morphology of freeze-dried hydrogels was studied by using a scanning electron microscope (Hitachi TM-3000 Tabletop SEM). A dramatic morphology difference was observed. (See, FIGS. 8A-F). pCBOH1 hydrogel shows the best homogeneity among all three samples. Additional intermolecular hydrogen bond may play an important role during photopolymerization process. Compared with the randomly distributed big holes appeared on pCBMA hydrogel, pCBOH1 hydrogel shows much stronger internal network across the boundary. In contrast, pCBOH2 hydrogel shows the finest structure and very thin fibrillar-like network, resulting in the lowest resistance to compression but higher break strain compared with pCBMA hydrogel.

As set forth above, biomaterials often contact with blood and/or body fluid and fouling process usually start with protein adsorption on a surface. Adsorbed proteins can aid bacterial attachment and colonization to cause infection and inflammation, and it can also trigger the foreign body response and cause the insulation of implanted devices or materials. Since protein adsorption on hydrogel surface cannot be accurately quantified, antifouling properties of pCBMAA-1 and pCBMAA-2 were evaluated on high packing and well-defined polymer brush surfaces via a surface-initiated photoiniferter-mediated polymerization method. See Example 17.

Figure 7A:
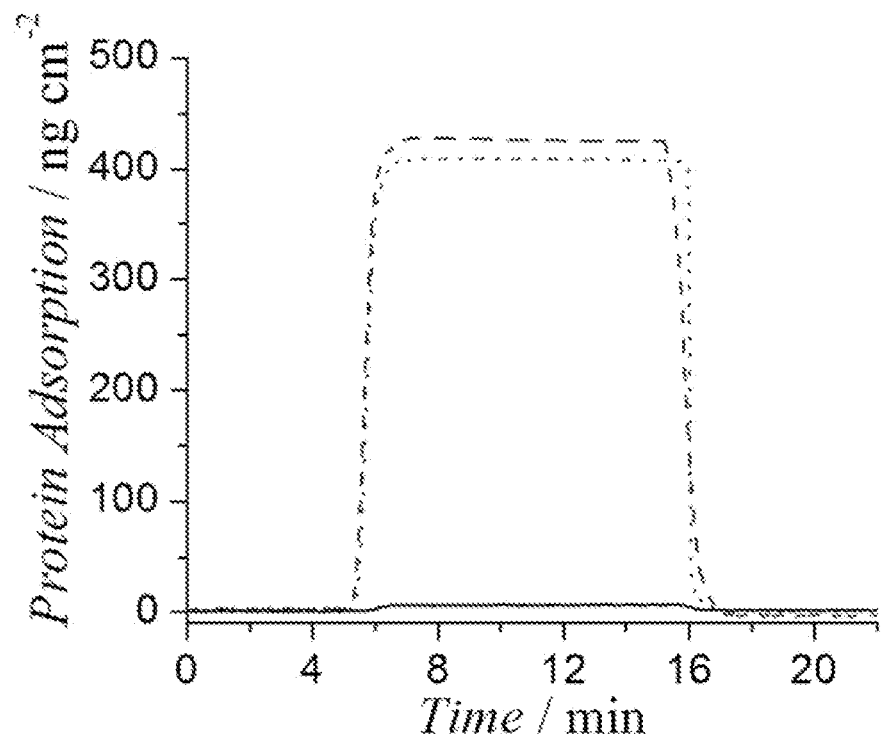
FIG. 7A-B are SPR sensorgrams showing ultralow fouling properties of zwitterionic pCBMAA-1 (7A) and pCBMAA-2 (7B) polymer brushes against the adsorption of 1 mg mL$^{-1}$ fibrinogen (solid line), undiluted human plasma (dashed line) and undiluted human blood serum (dotted line).
Figure 7B:
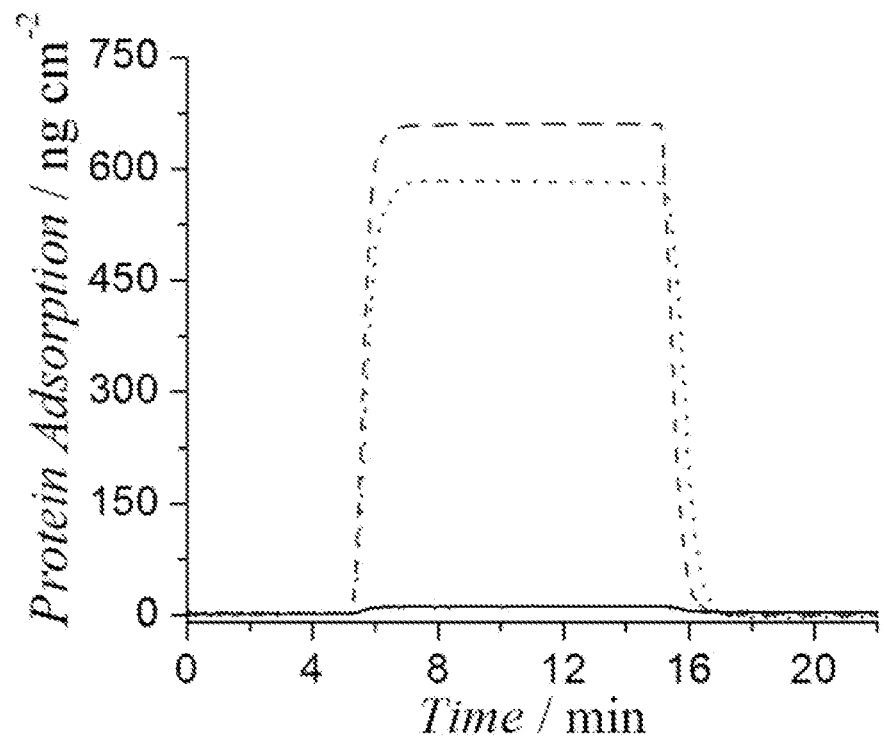
Figure 8:
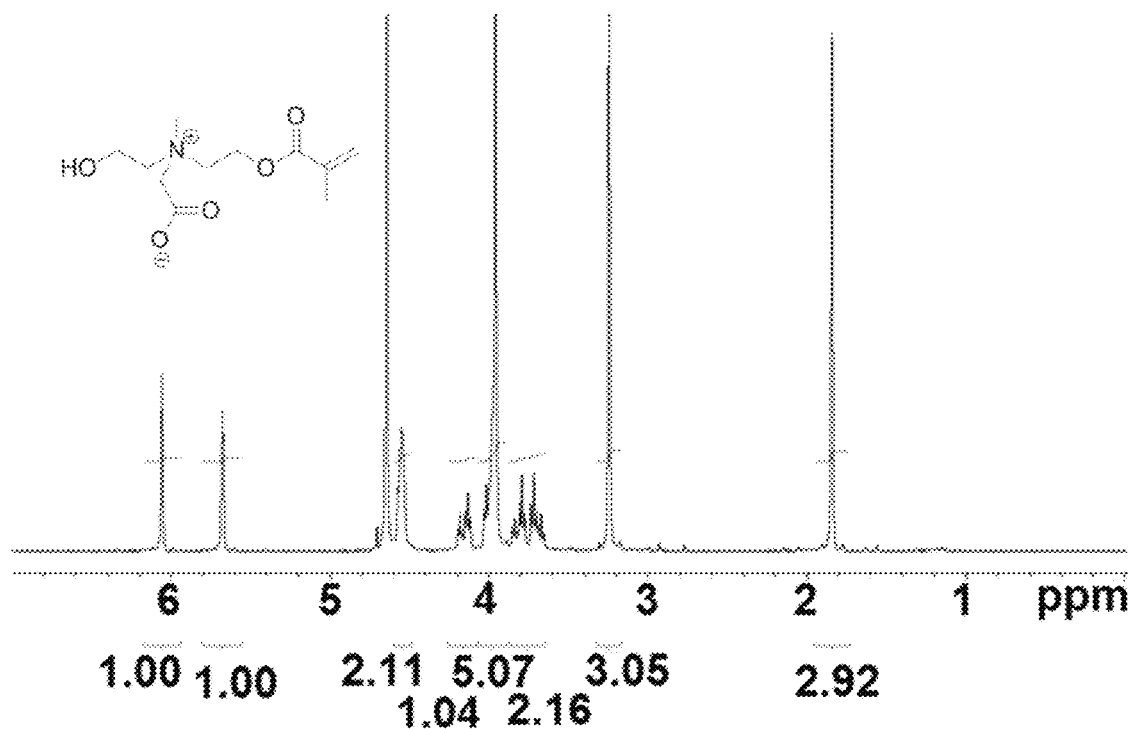
FIG. 8 is a $^1$H NMR of CBOH1 spectrum at 300 MHz, $D_2O$.

As shown in FIGS. 7A, 7B, both pCBMAA-1 and pCBMAA-2 surfaces highly resist protein adsorption from the single protein (fibrinogen) solution and complex solutions (blood plasma and serum). The amount of adsorbed protein is below the detection limit (0.3 ng cm$^{-2}$) of the SPR sensor. SPR results show that both pCBMAA-1 and pCBMAA-2 can achieve excellent antifouling results with very thin films. Materials contacting blood with less than 5 ng cm$^{-2}$ adsorbed fibrinogen is considered as ultralow fouling materials and it is found that ultralow fouling materials is less likely trigger blood coagulation through platelet activation pathway. Ultralow fouling materials are highly desired to be used as the top layer to contact blood.

It can be used as coatings for any devices contacting aqueous complex media, such as blood, urine and body fluid or coatings to protect fouling for any substrate required long-term contact with aqueous media. It can be copolymerized with other ionic or nonionic monomers to form co-polymers and used as the carrier for the delivery of small molecule drugs, protein/peptide drugs and nucleic acids. It can be used as tissue engineering scaffold, wound dressing and antifouling/antimicrobial coatings. It can be used in contact lens. It can be used in biosensor to encapsulate the enzyme or provide antifouling background.

In light of the foregoing, it should be appreciated that the present invention significantly advances the art by providing switchable zwitterionic carboxybetaine-based polymers, hydrogels and/or elastomers, as well as their related uses and methods, that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Ethanol, methanol, ethyl acetate, dichloromethane, hexane, acetonitrile, tetrahydrofuran (THF), anhydrous diethyl ether, iodomethane, trifluoroacetic acid (TFA), acetic acid (HAc), trifluoroacetic acid-d (TFA-d), acetic acid-d (HAc-d), sodium hydroxide, anhydrous magnesium sulfate, ion exchange resin (Amberlyst® A26, OH-form), silica gel 60, phosphate-buffered saline (PBS) and human fibrinogen (Fg) were purchased from Sigma-Aldrich (St. Louis, Mo.). 2-((2-aminoethyl)amino)ethanol, methacrylic anhydride, tert-butyl bromoacetate, tert-butyl acrylate were obtained from Alfa Aesar (Ward Hill, Mass.). Pooled human blood plasma and serum were purchased from BioChemed Services (Winchester, Va.). Water used in all experiments was purified using a Milli-Q Direct 8 Ultrapure Water system (Millipore, Billerica, Mass.) to reach a resistivity above 18.0 MΩ·cm.

Column chromatography was carried out on flash silica gel obtained from Sigma. Carboxybetaine dimethacrylate (crosslinker) was synthesized following a published procedure. See, e.g. L. R. Carr, H. Xue, S. Y. Jiang, Biomaterials 2011, 32, 961, the disclosure of which is incorporated by reference herein in its entirety. Mercaptoundecyl bromoisobutyrate was synthesized through the reaction of bromoisobutyryl bromide and 11-mercapto-1-undecanol using a method published previously. See e.g. D. M. Jones, A. A. Brown, W. T. S. Huck, Langmuir 2002, 18, 1265, the disclosure of which is incorporated by reference herein in its entirety.

Example 1

Synthesis of CBOH1 Monomer

Synthesis of 2-((2-hydroxyethyl)(2-(methacryloyloxy)ethyl)(methyl) ammonio)acetate)(CBOH1) was achieved using a three step method as show in Scheme 4, below.

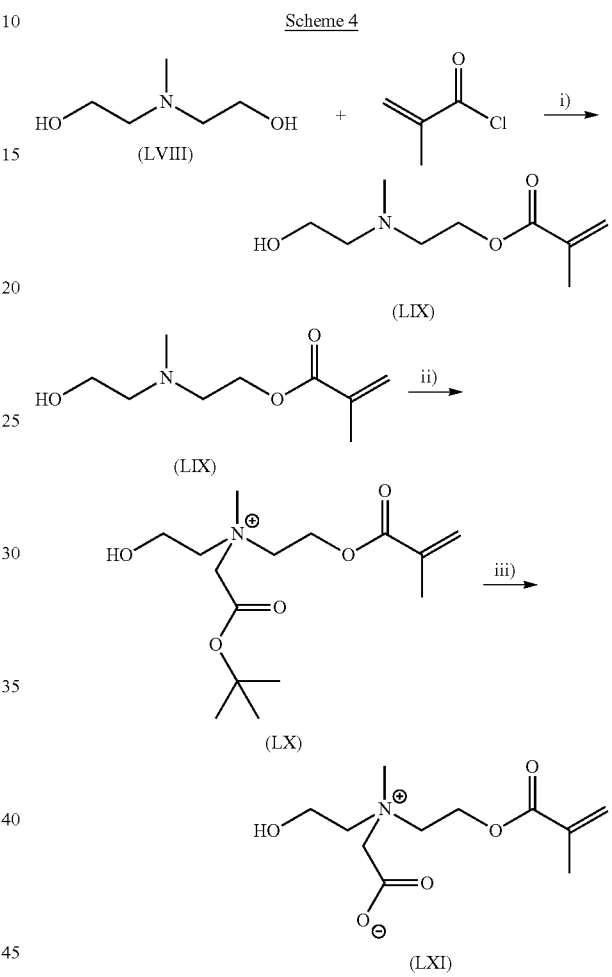

First, synthesis of 2-((2-hydroxyethyl)(methyl)amino) ethyl methacrylate (compound LIX) was achieved as follows. 20 mL (174 mmole) of N-methyl diethanol amine (LVIII), 120 mL of anhydrous tetrahydrofuran (THF) and 60 g (566 mmole) of anhydrous sodium carbonate powder were added to a 500 mL three-neck round bottom flask. The mixture was cooled down to 0° C. with an ice-bath. 17 mL (174 mmole) of methacryloyl chloride (diluted with 30 mL of anhydrous THF) was added dropwise. Then the ice-bath was removed, and the reaction was stirred at room temperature overnight. After the reaction was completed, the reaction solution was filtered. The solvent in the filtrate was removed with a rotary evaporator, and the residue was dried with a vacuum pump fitted with a liquid nitrogen cold trap. The product was further purified by silica gel column chromatography (ethyl acetate/hexane, 1/1 (v/v)). Pure product (compound LIX) was obtained as a colorless liquid. (Yield: 53%). $^1$H NMR (300 MHz, CDCl$_3$) δ6.12 (s, 1H), 5.58 (s, 1H), 4.26 (t, J=5.6 Hz, 2H), 3.58 (t, J=5.3 Hz 2H), 2.77 (t, J=5.7 Hz, 2H), 2.62 (t, J=5.4 Hz, 2H), 2.35 (s, 3H), 1.95 (s, 3H) 1 hydroxy peak not seen due to overlapping signals. $^{13}$C NMR (300 MHz, CDCl$_3$) δ167.61, 136.38, 125.96, 62.50, 59.06, 58.50, 55.94, 42.16, 18.53.

Second, synthesis of 2-(tert-butoxy)-N-(2-hydroxyethyl)-N-(2-methacryloyloxy)ethyl)-N-methyl-2-oxoethanaminium bromide (compound LX) was achieved as follows. 17.1 g (79 mmole) of compound LIX was dissolved in 150 mL of acetonitrile in a nitrogen filled flask, followed by adding 14 mL (95 mmol) of t-butyl bromoacetate. The mixture was stirred at 60° C. for 2 days. After solvent removal with a rotary evaporator, the residue was precipitated in diethyl ether and dried under vacuum to obtain a white solid with quantitative yield. $^1$H NMR (300 MHz, CDCl$_3$) δ6.06 (s, 1H), 5.58 (s, 1H), 4.92 (s, 1H), 4.63 (m, 2H), 4.56 (s, 2H), 4.34 (m, 2H), 4.06 (m, 2H), 4.00 (m, 2H), 3.58 (s, 3H), 1.87 (s, 3H), 1.41 (s, 9H). $^{13}$C NMR (300 MHz, CDCl$_3$) δ166.30, 163.62, 135.19, 127.32, 85.45, 64.87, 62.21, 61.19, 58.18, 55.61, 50.84, 28.02, 18.31.

Figure 9:
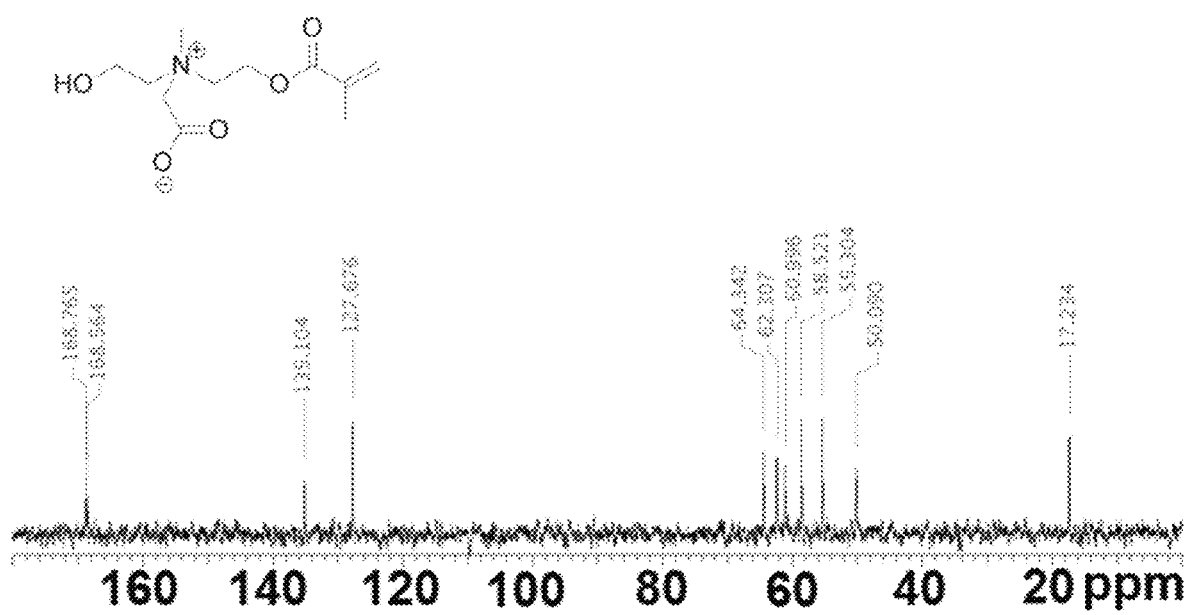
FIG. 9 is a $^{13}$C NMR of CBOH1 spectrum at 300 MHz, $D_2O$.

Last, synthesis of 2-((2-hydroxyethyl)(2-(methacryloyloxy)ethyl) (methyl)ammonio)acetate (compound LXI: CBOH1) was achieved as follows. 3 g of compound LX was dissolved in 6 mL of trifluoroacetic acid (TFA) and 6 mL of dichloromethane for 1.5 hours at room temperature to remove the tert-butyl group. The mixture was precipitated in diethyl ether and dried under vacuum. The product was redissolved in acetonitrile, neutralized over a basic ion exchange resin (IRA-400 OH form), and further purified by silica gel column chromatography (Ethyl Acetate/Methanol 1/1 v/v). (Yield: 86%). $^1$H NMR (300 MHz, D$_2$O) δ6.21 (s, 1H), 5.83 (s, 1H), 4.70 (m, 2H), 4.31 (m, 2H), 3.91 (m, 2H), 4.11 (m, 4H), 3.40 (s, 3H), 1.99 (s, 3H). (FIG. 8) $^{13}$C NMR (300 MHz, D$_2$O) δ168.77, 168.58, 135.11, 127.68, 64.35, 62.32, 61.00, 58.53, 55.31, 50.10, 17.24. $^{13}$C NMR spectrum of CBOH1 is shown in FIG. 9.

Example 2

Synthesis of CBOH2 Polymer

The synthesis procedures of CBOH2 were similar to that of CBOH1 described in Example 1 above, except that the starting material is tri-(2-hydroxyethyl)amine (LXII) rather than N-methyl diethanol amine. The reaction procedures are outlined in Scheme 5, below.

Scheme 5

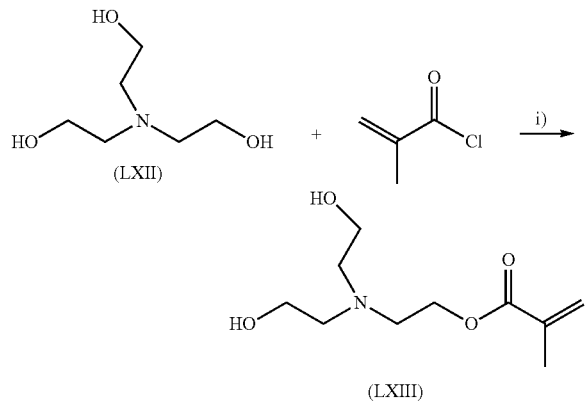

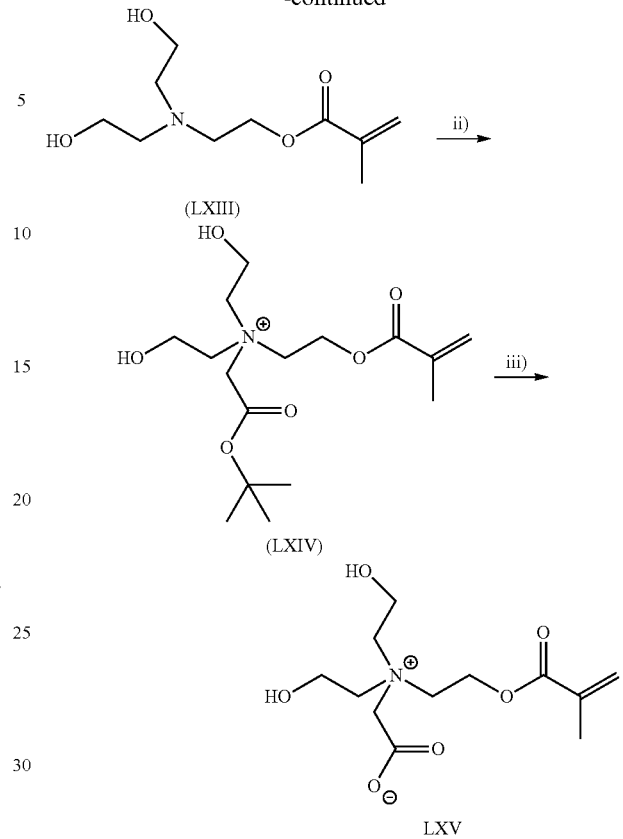

First, synthesis of 2-(bis(2-hydroxyethyl)amino)ethyl methacrylate (compound LXIII) was achieved as by reacting tri-(2-hydroxyethyl)amine (LXII) with methacryloyl chloride in the manner set forth in Example 1 above to form compound LXIII. $^1$H NMR (300 MHz, CDCl$_3$) δ6.13 (s, 1H), 5.59 (s, 1H), 4.27 (t, J=5.6 Hz, 2H), 3.62 (t, J=5.3 Hz, 4H), 2.89 (t, J=5.6 Hz, 2H), 2.75 (t, J=5.3 Hz, 4H), 1.95 (s, 3H) 1 hydroxy peak not seen due to overlapping signals. $^{13}$C NMR (300 MHz, CDCl$_3$) δ167.82, 136.32, 126.14, 62.83, 59.93, 56.89, 53.72, 18.48.

Second, synthesis of (2-(tert-butoxy)-N,N-bis(2-hydroxyethyl)-N-(2-(methacryloyloxy)ethyl)-2-oxoethanaminium bromide)(compound LXIV) was achieved as by reacting compound LXIII with tert-butyl bromoacetate in the manner set forth in Example 1 above to form compound LXIV. The crude product from the second step was not purified and directly used for the next step.

Figure 10:
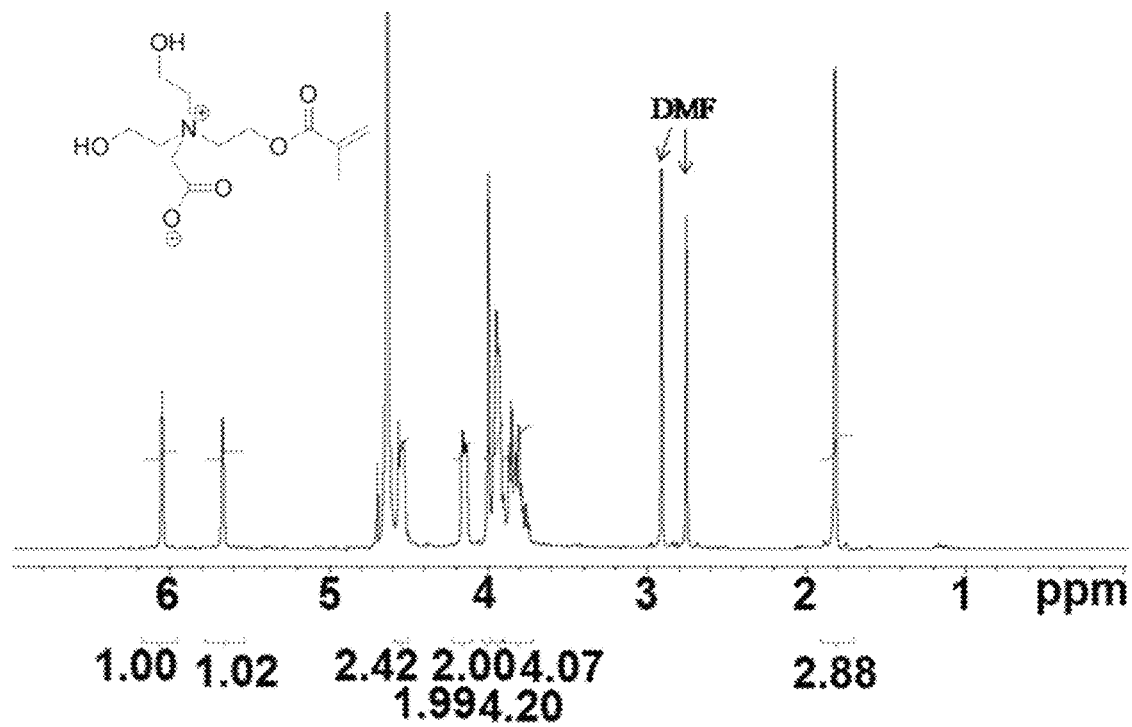
FIG. 10 is a $^1$H NMR spectrum of CBOH2 at 300 MHz, $D_2O$.
Figure 11:
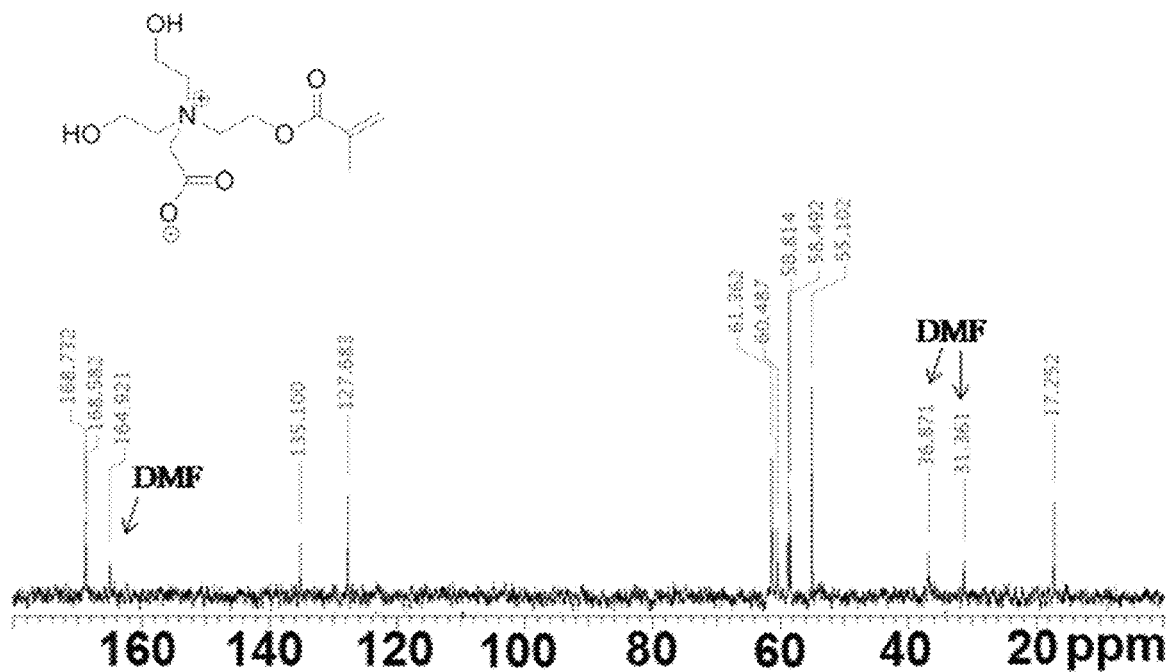
FIG. 11 is a $^{13}$C NMR of CBOH1 spectrum at 300 MHz, $D_2O$.

Last, synthesis of 2-(bis(2-hydroxyethyl)(2-(methacryloyloxy)ethyl) ammonio)acetate (compound LXV: CBOH2) was achieved by combining compound LXIV with trifloroacetic acid (TFA) in dichloromethane and neutralizing the resulting compound over a basic ion exchange resin in the manner set forth in Example 1 above to form compound LXV. $^1$H NMR (300 MHz, D$_2$O) δ6.21 (s, 1H), 5.83 (s, 1H), 4.70 (m, 2H), 4.31 (m, 2H), 4.16 (s, 2H), 4.10 (m, 4H), 4.01 (m, 4H), 1.99 (s, 3H). (See, FIG. 10). $^{13}$C NMR (300 MHz, D$_2$O) δ168.74, 168.58, 135.10, 127.68, 61.37, 60.49, 58.82, 58.50, 55.11, 17.25. (See, FIG. 11).

Example 3

Ring Open Kinetics

Figure 12:
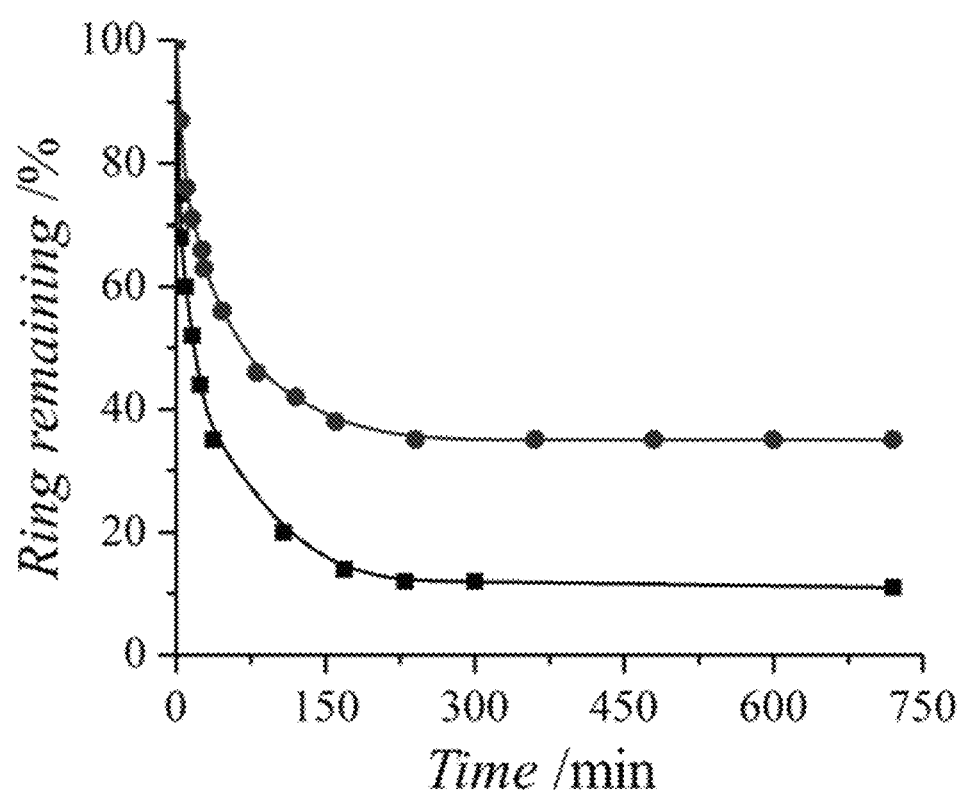
FIG. 12 is a graph showing the conversion kinetics of cationic CBOH1 (squares) and CBOH2 (dots) to zwitterionic CBOH1 and CBOH2 monomers in pH 7.3 solution.

The ring open kinetics of the CBOH1 and CBOH2 monomers were studied by dissolving monomers in their ring form in 0.2 M $Na_2CO_3$ buffer solution in $D_2O$ at pH 7.3. (See, FIG. 12) Calculations were performed with the same method as ring-formation; the final conversion within 5 hours was 89% for CBOH1 and 65% for CBOH2. From the aspect of thermal dynamics, CBOH2 is expected to have a lower dissociation constant compared to CBOH1 under the same condition. From the aspect of kinetics, CBOH2 is expected to have a higher reaction coefficient for ring formation process and has a lower reaction coefficient for ring open compared to CBOH1. Our results reflected both expected trends.

Example 4

Hydrogel Preparation for Antimicrobial Test and Compression Test for CBOH1 and CBOH2 Polymers For antimicrobial tests, both CBOH1 and CBOH2 monomers were kept in their ring form and directly photopolymerized in DMSO. The reaction solution contains monomer (3 M), carboxybetaine dimethacrylate (0.06 M) and 2-hydroxy-2-methylpropiophenone (0.5 wt %). The solution was transferred into a mold made of two quartz slides separated by a 2 mm thick poly tetrofloroethylene (PTFE) spacer and polymerized under UV (362 nm) for 1 hour. The gels were immersed in acetonitrile for 3 days. Before the antimicrobial study, the gels were equilibrated in water for 2 hours to obtain hydrogels. Because of the poor solubility in organic solvents, pCBMA hydrogels (used as a control) were prepared at the same concentration with the same method in $H_2O$.

Hydrogels for compression test were prepared using CBOH1 and CBOH2 monomers in their zwitterionic form in water following a above described procedure.

Example 5

Evaluation of the Bacterial Activity of CBOH1 and CBOH2 Polymers

To evaluate antimicrobial properties, a strain of gram negative E. coli K12 was used as a model species. Before the test, hydrogel samples were punched into 8 mm diameter discs and equilibrated in PBS buffer solution. The method for evaluating the antibacterial efficiency of polymer surfaces was modified from a previously published method. See G. Cheng, H. Xue, Z. Zhang, S. Chen, S. Jiang, Angew. Chem. Int. Ed. 2008, 47, 8831, the disclosure of which is hereby incorporated by references in its entirety. E. coli K12 was cultured at 37° C. in Luria-Bertani (LB) medium (20 g $L^{-1}$) to reached an optical density of 0.8 at 600 nm. After wash with PBS, cells were suspended in PBS to get a final concentration of $5\times10^7$ cells/mL. E. coli suspension (20 µL) was pipetted onto a hydrogel disc (8 mm in diameter) and incubated at room temperature for 1 hour. Then each sample was placed into one well of a sterile 24-well plate with LB medium (1 mL) and cultured at 37° C. for 18 hours. The Bacterial culture in each well was diluted serially in water and spread on LB agar plates. After 18 hours at 37° C., the number of the colony on agar plates was recorded to calculate the concentration of live bacterial cells. See FIG. 13 and Table 1, below. pCBMA hydrogel was used as the negative antimicrobial control. The antimicrobial efficiency was calculated from the amount of live cells on the tested surfaces relative to those on pCBMA hydrogel surfaces. Both hydrogels made from CBOH1 and CBOH2 in cationic ring form inhibited bacterial growth and killed more than 99.99996% E. coli K12 within 1 hour relative to pCBMA-2 surfaces. Since cationic compounds, unlike antibiotics, kill bacterial cells non-specifically, they have less chance to generate antibiotic-resistant strains. This property is particularly important in long-term applications such as chronic infection treatment and wound healing.

TABLE 1

|  | pCBMA | pCBOH1 | pCBOH2 |
|---|---|---|---|
| Live bacterial concentration (CFU/mL) | 5.36E+08 | <200 | <200 |
| Antimicrobial efficiecy (%) | — | >99.99996 | >99.99996 |

Example 6

Bacteria Attachment, Viability and Releasing Test for CBOH1 and CBOH2 Polymers

The ability of catch, kill and release of E. coli K12 were tested on pCBOH1 and pCBOH2 hydrogel surfaces before and after hydrolysis. Fresh E. coli suspension in phosphate buffered saline (PBS) (50 µL) was pipetted onto a hydrogel disc and incubated at room temperature for 1 hour. To analyze the density of bacteria accumulated on hydrogel surfaces, samples were gently rinsed with water, and stained with LIVE/DEAD BacLight Bacterial Viability assay kit. After the staining, the number of live and dead cells was determined with an Olympus IX81 fluorescent microscopy with 60× oil lens through FITC and Cys3 filters. Following imaging, the sample was placed in PBS buffer for 16 hours. The number of remaining E. coli was again determined by fluorescent microscopy. Four separate samples were analyzed for each hydrogel sample.

Figure 13:
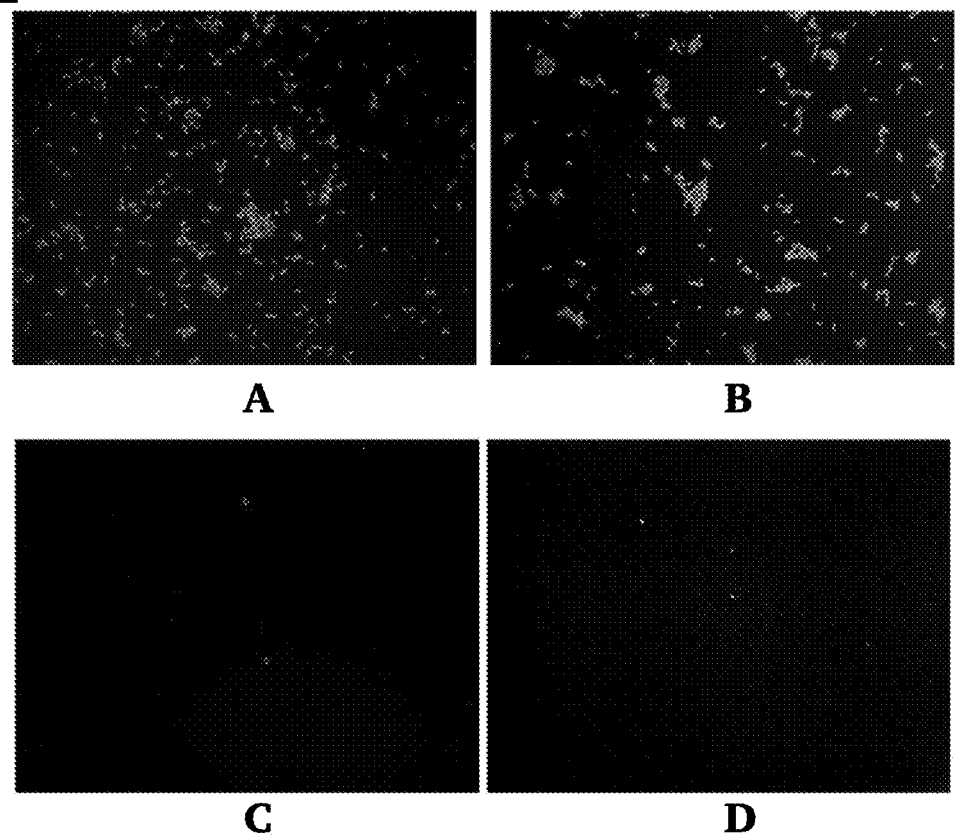
FIG. 13A-D is a series of four representative fluorescence microscopy images of bacterial attachment on pCBOH1 in cationic form (A), pCBOH2 in cationic form (B), hydrogels before hydrolysis and on pCBOH1 in zwitterionic form (C), pCBOH2 in zwitterionic form (D), hydrogels after 16 hours hydrolysis in PBS. Bacterial cells were stained with LIVE/DEAD BacLight Bacterial Viability assay kit.
Figure 14:
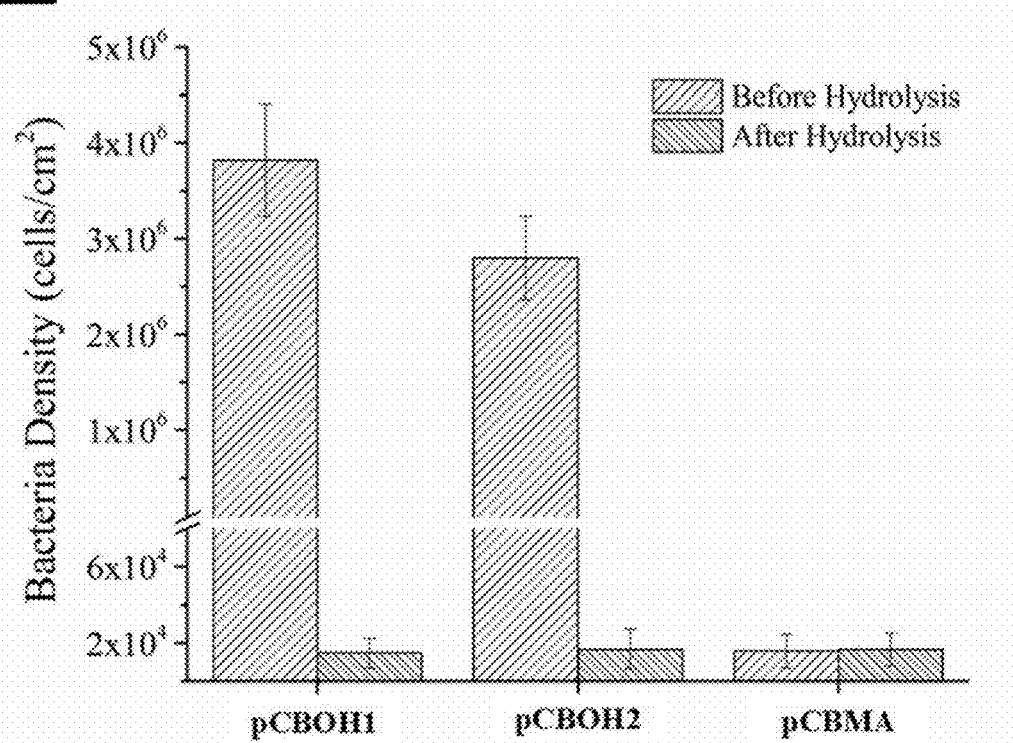
FIG. 14 is a graph showing the attachment of E. coli K12 from a suspension with 5×10$^7$ cells mL$^{-1}$ for 1 hour exposure to cationic pCBOH1, cationic pCBOH2 and zwitterionic pCBMA hydrogels before and after hydrolysis (n=6).

As shown in FIG. 13, a large amount of bacteria were caught and trapped on the cationic pCBOH1 (ring form) and pCBOH2 (ring form) hydrogel surfaces before hydrolysis, whereas only few bacterial cells were found on the zwitterionic pCBMA surface. The quantitative data for the amount of bacterial cells remaining on hydrogel surface before and after hydrolysis is shown in FIG. 14. The surface density of attached E. coli on cationic pCBOH1 and pCBOH2 (ring form) hydrogels are $3.8\times10^6$ and $2.8\times10^6$ cells $cm^{-2}$ respectively, and after overnight hydrolysis, the surfaces released 99.6% and 99.4% of attached cells for pCBOH1 and pCBOH2 hydrogels at zwitterionic form respectively. The cell viability assay (See, FIGS. 13, 14, Table 1, below) showed that pCBOH1 and pCBOH2 in their cationic ring form can cause cell membrane damage of over 99% attached cells. Upon overnight hydrolysis in PBS buffer solution, both pCBOH1 and pCBOH2 hydrogels became antifouling and released most of the killed bacterial cells, while CBMA hydrogel retained very low bacterial adhesion, but it cannot kill any of attached bacterial cells. See Table 1, above.

Example 7

Synthesis of Polymer Brushes Via Si-ATRP

The polymer brushes were synthesized via surface initiated ATRP (si-ATRP). Gold-coated sensor chips were treated followed previous reported procedures. See e.g. G. Cheng, H. Xue, Z. Zhang, S. Chen, S. Jiang, Angew. Chem. Int. Ed. 2008, 47, 8831, the disclosure of which is incorporated by reference herein in its entirety. The initiator self assembled SAMs were formed by soaking gold-coated substrates in a pure ethanol solution containing 0.1 mM co-mercaptoundecyl bromoisobutyrate at room temperature for 24 h. A monomer solution (0.12 g/mL) in DMF/water (3/1) was degas under a positive nitrogen flow, two treated chips with an initiator self-assembled monolayer (SAM), 71.3 mg of copper(I) bromide and 154.3 mg of 2,2'-bipyridine (BPY) were placed in a reaction tube under nitrogen. The degassed monomer solution was then transferred into the reactor and left shaking on an orbital shaker for 16 h. After the reaction, the chips were rinsed with ethanol and water, and stored in PBS.

Example 8

Protein Adsorption Test for pCBOH1 and pCBOH2 Polymer Brushes

A four-channel SPR sensor was used to measure protein adsorption on pCBOH1 and pCBOH2 polymer brushes. First, a PBS buffer at 50 μL/min flow rate was used to obtain a baseline signal. 1 mg/mL bovine fibrinogen solution or 100% human blood plasma was then injected for 10 minutes followed by a PBS wash to remove any loosely bound proteins. The amount of adsorbed proteins was calculated as the change in wavelength before and after protein injection and is reported on FIGS. 2A, 2B.

Example 9

Hydrogel Preparation for Antimicrobial Test and Compression Test for pCBOH1 and pCBOH2

For antimicrobial test, both CBOH1 and CBOH2 monomers were kept in their cationic ring form and directly photopolymerized in DMSO as set forth above. The reaction solution contained 3 M monomer, 0.06 M carboxybetaine dimethacrylate as a crosslinker and 0.5 wt % 2-hydroxy-2-methylpropiophenone, as a photoinitiator. The carboxybetaine dimethacrylate was synthesized following a published procedure. See L. R. Carr, H. Xue, S. Y. Jiang, *Biomaterials* 2011, 32, 961, the disclosure of which is incorporated by reference herein in its entirety. The reaction solution was transferred into a mold made of two quartz slides separated by a 2 mm thick PTFE spacer and polymerized under UV (362 nm) for 1 hour. The resulting gels were immersed in acetonitrile for 3 days. Before the antimicrobial study, the gels were equilibrated in water for 2 hours to obtain hydrogels. Because of its poor solubility in organic solvents, the pCBMA hydrogel (used as a control) was prepared at the same concentration with the same method in $H_2O$.

The hydrogels for the compression testing were prepared using CBOH1 and CBOH2 monomers in their zwitterionic form in water following the above procedure.

Example 10

Water Content Evaluation of pCBMA, pCBOH1, and pCBOH2 Hydrogels

The water content is a basic property of hydrogel materials used for biomedical applications. Wet weight of the samples of pCBMA pCBOH1, and pCBOH2 hydrogels at two concentrations (1.5M and 3.0M) were measured after removal of excess water from the samples. Dry weight was recorded after the samples had been dried at 65° C. under vacuum for 72 hours. The water contents of hydrogels (as a percent) were calculated by (Wet weight−Dry weight)/Wet weight×100 and are reported on Table 2, below.

TABLE 2

| Equilibrium water content (average of 3 samples) | | | |
|---|---|---|---|
| | pCBMA | pCBOH1 | pCBOH2 |
| Water content of hydrogel (1.5M) | 90.6% | 84.2% | 87.2% |
| Water content of hydrogel (3M) | 85.3% | 71.7% | 73.7% |

Example 11

Compression Test for pCMBA, pCBOH1, and pCBOH2 Hydrogels

The compression moduli of pCBOH1 and pCBOH2 hydrogels at two concentrations (1.5M and 3.0M) were tested. At least five disks of each hydrogel (2 mm thickness when cast) were compressed to failure at a rate of 1 mm/min using an Instron 5543 mechanical tester with a 100 N load cell. The Young's modulus was calculated from the linear portion between 1-2% and 11-12% strain.

Figure 15A:
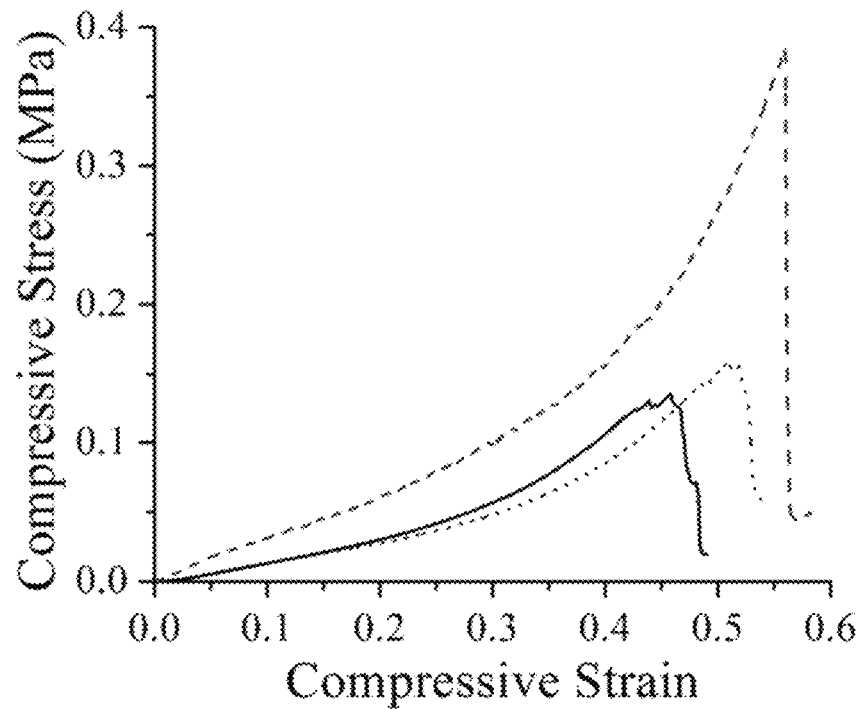
FIG. 15A-B are graphic comparisons of compression stress vs. strain curve for pCBOH1 (dashed line), pCBOH2 (dotted line), and pCBMA (solid line) hydrogels prepared at 1.5 M (A) and 3M (B) respectively.
Figure 15B:
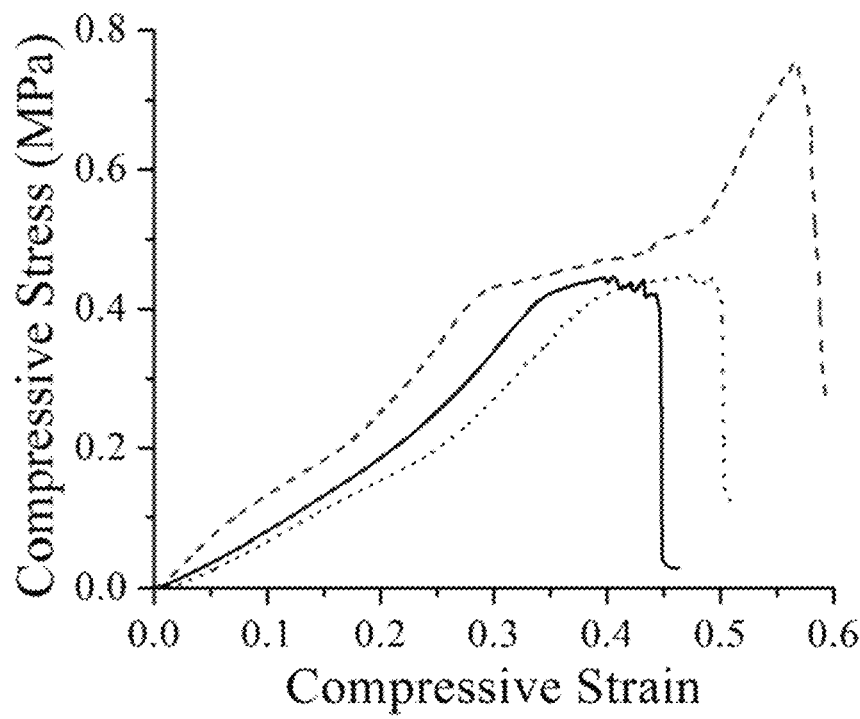

Compared with the pCBMA hydrogels, the pCBOH1 hydrogels showed significantly increased modulus, about 73% higher at 1.5 M, and 43% higher at 3 M. pCBOH1 hydrogels also show about two times higher break stress and about 30% higher break strain than pCBMA hydrogels, at both low and high concentration. The higher compression modulus, break stress, and strain at break were attributed to asymmetrically fused hydroxyethyl groups with neighboring carbonyl groups. As shown in FIG. 15A, 15B, hydrogen bonding is more predominant at the lower concentration than the higher concentration.

Example 12

Bacterial Activity Test for pCBMA, pCBOH1, and pCBOH2 Hydrogels

The method for evaluating the antibacterial efficiency of polymer surfaces was modified from a previously published method. See G. Cheng, H. Xue, G. Z. Li, S. Y. Jiang, *Langmuir* 2010, 26, 10425, the disclosure of which is incorporated by reference herein in its entirety. *E. coli* K12 was cultured at 37° C. in Luria-Bertani (LB) medium (20 g/L) to reach an optical density of 0.8 at 600 nm. After wash with PBS, cells were suspended in PBS to get a final concentration of $5 \times 10^7$ cells/mL. 20 μL of *E. coli* suspension was pipetted onto a hydrogel disc (8 mm in diameter) and incubated at room temperature for 1 hour. Then each sample was placed into one well of a sterile 24-well plate with 1 mL of LB medium and cultured at 37° C. for 18 hours. Bacterial culture in each well was diluted serially in water and spread on LB agar plates. After 18 hours at 37° C., the number of the colony on agar plates was recorded to calculate the concentration of live bacterial cells. The results of these tests are reported on Table 2, above.

Example 13

Bacteria Attachment, Viability and Releasing Test for pCBMA, pCBOH1, and pCBOH2 Hydrogels 50 μL of fresh *E. coli* suspension in PBS was pipetted onto a pCBMA, pCBOH1, or pCBOH2 hydrogel disc (8 mm in diameter) and incubated at room temperature for 1 hour. To analyze the density of bacteria accumulated on hydrogel surfaces, samples were gently rinsed with water, and stained with LIVE/DEAD BacLight Bacterial Viability assay kit. After the staining, the number of live and dead cells was determined with an Olympus IX81 fluorescent microscopy with 60× oil lens through FITC and Cys3 filters, and the results are shown in Table 3. Following imaging, the sample was placed in PBS buffer for 16 hours. The number of remaining E. coli was again determined by fluorescent microscopy. Four separate samples were analyzed for each hydrogel sample.

TABLE 3

Cell viability of E. coli K12 on hydrogels in their ring form before hydrolysis.

|  | pCBMA | pCBOH1 | pCBOH2 |
|---|---|---|---|
| % of cells with membrane damage (in red) | 38.89 ± 37.51 | 99.13 ± 0.45 | 99.42 ± 0.34 |

Example 14

Synthesis of CBMAA-1 and CBMAA-2

Two carboxybetaine-based monomers, CBMAA-1 and CBMAA-2, were synthesized via three-step reactions as shown in Scheme 3, above.

1. Synthesis of N-(2-((2-hydroxyethyl)amino)ethyl) methacrylamide (LIII)

Figure 16:
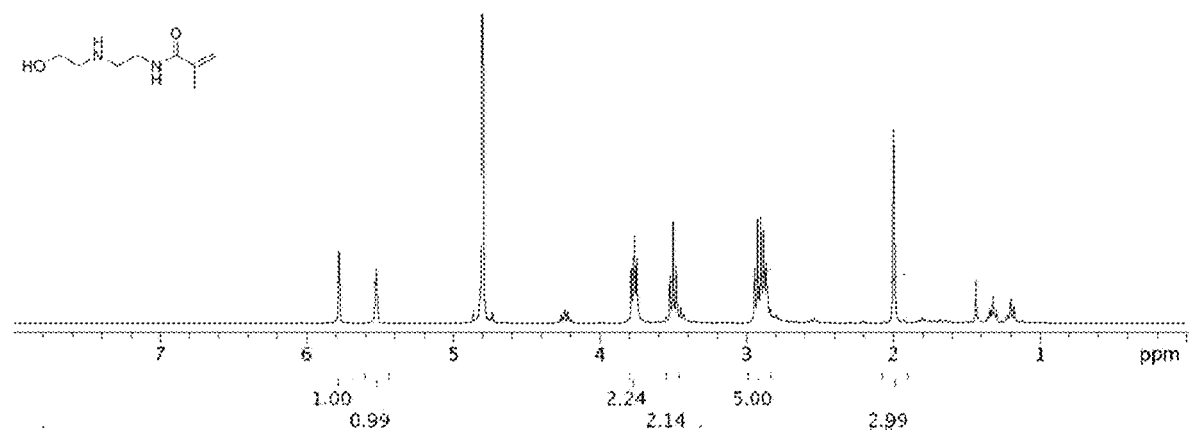
FIG. 16 is a $^1$H NMR Spectra of compound LIII (300 MHz).
Figure 17:
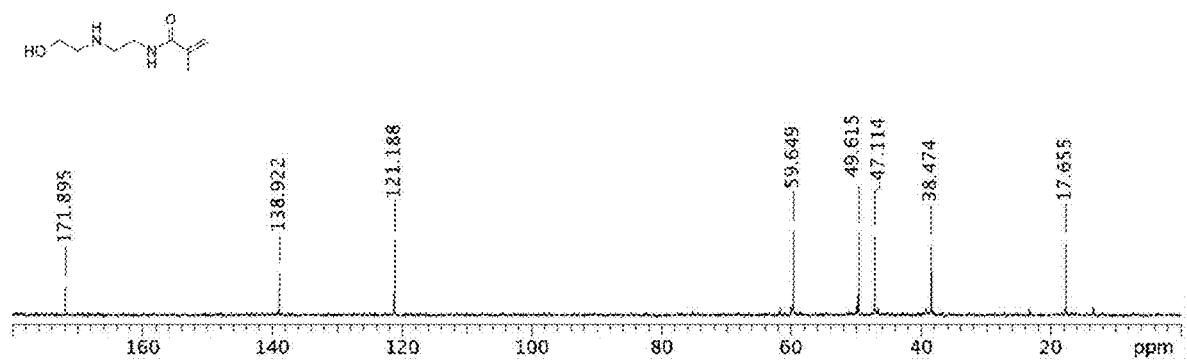
FIG. 17 is a $^{13}$C NMR Spectra of compound LIII (75 MHz).

4.8 g (0.12 mole) of NaOH was dissolved in a mixture of 30 mL de-ionized water and 70 mL ethanol in a 250 mL three-neck round bottom flask, followed by 10.1 mL (0.1 mole) of 2-((2-aminoethyl)amino)ethanol (LI). The mixture was cooled down to 0° C. with an ice bath. 17.4 mL (0.11 mole) of methacrylic anhydride (LII) was added dropwise under nitrogen protection. After stirring at 0° C. for 2 hours, the reaction was stirred at room temperature for 3 hours to produce compound LIII. The crude product was directly used for the next reaction without purification. For verification purposes, a small amount of the crude product was purified by silica gel column chromatography (ethyl acetate/methanol, 2/1 (v/v)). The pure product was obtained as a colorless liquid and analyzed by NMR. $^1$H NMR (300 MHz, CDCl$_3$) δ 5.79 (s, 1H), 5.27 (s, 1H), 3.77 (t, J=5.7 Hz, 2H), 3.50 (t, J=6.3 Hz 2H), 2.94-2.86 (m, 4H), 1.99 (s, 3H) FIG. 16. $^{13}$C NMR (75 MHz, CDCl$_3$) δ 171.90, 138.92, 121.19, 59.65, 49.62, 47.11, 38.47, 17.66 FIG. 17.

2. Synthesis of Tert-butyl N-(2-hydroxyethyl)-N-(2-methacrylamidoethyl)glycinate (LIV)

Figure 18:
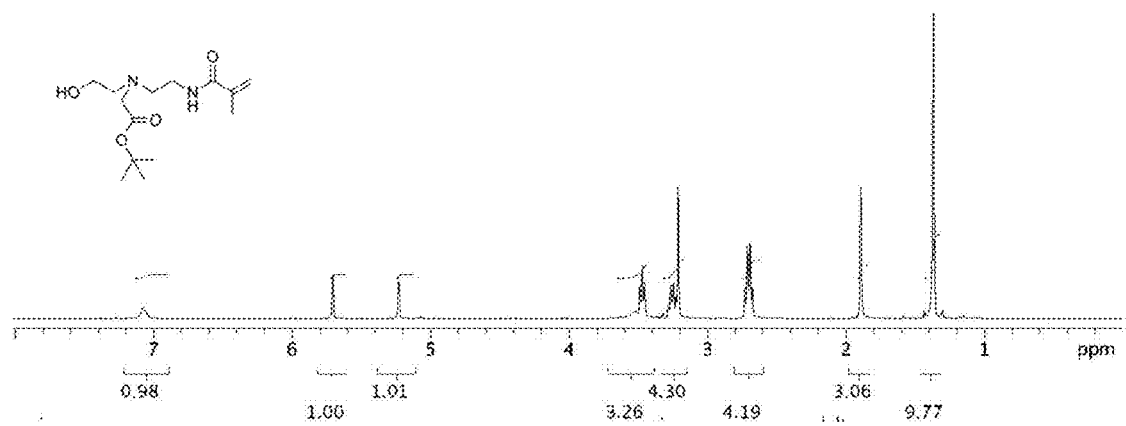
FIG. 18 is a $^1$H NMR Spectra of compound LIV (300 MHz).
Figure 19:
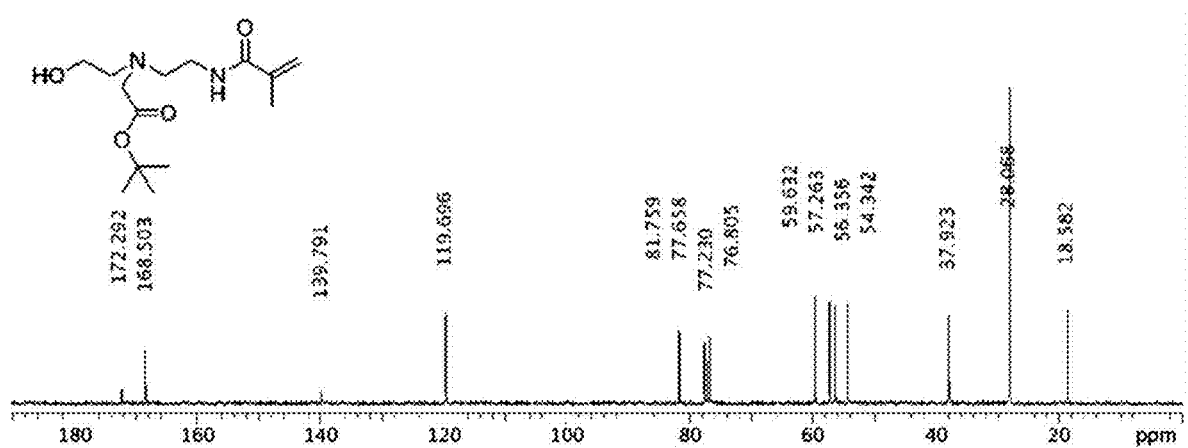
FIG. 19 is a $^{13}$C NMR Spectra of compound LIV (75 MHz).

17.7 mL (0.12 mole) of tert-butyl bromoacetate was added into the mixture of the crude compound LIII and heated overnight at 60° C. under nitrogen with stirring. Ethanol was removed with a rotary evaporator, and the pH value was adjusted to ~10 with NaOH. After extraction with ethyl acetate twice, the organic phase was washed by water and dried with anhydrous magnesium sulfate. After filtration, the liquid was concentrated and purified by silica gel column chromatography (ethyl acetate/hexane, 4/1 (v/v)) to produce compound LIV. (Two-step yield: 36%). $^1$H NMR (300 MHz, CDCl$_3$) δ 7.07 (s, 1H), 5.71 (s, 1H), 5.23 (s, 1H), 3.54 (s, 1H), 3.47 (t, J=5.3 Hz, 2H), 3.26 (m, 2H), 3.22 (s, 2H), 2.70 (m, 4H), 1.89 (s, 3H), 1.37 (s, 9H) (FIG. 18). $^{13}$C NMR (75 MHz, CDCl$_3$) δ 172.29, 168.50, 139.79, 119.70, 81.76, 59.63, 57.26, 56.36, 54.34, 37.92, 28.07, 18.58 (FIG. 19).

3. Synthesis of Tert-butyl 3-((2-hydroxyethyl) (2-methacrylamidoethyl)amino)propanoate (LV)

Figure 20:
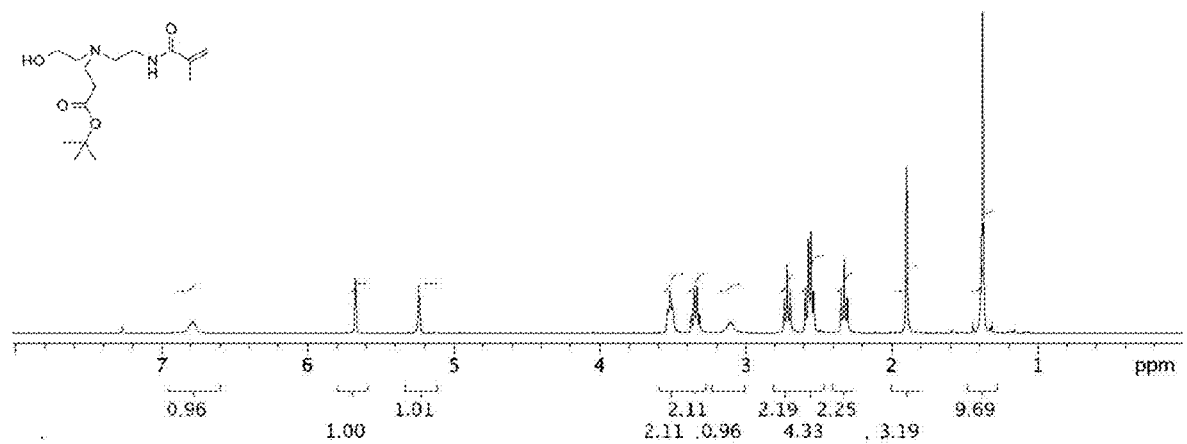
FIG. 20 is a $^1$H NMR Spectra of compound LV (300 MHz).
Figure 21:
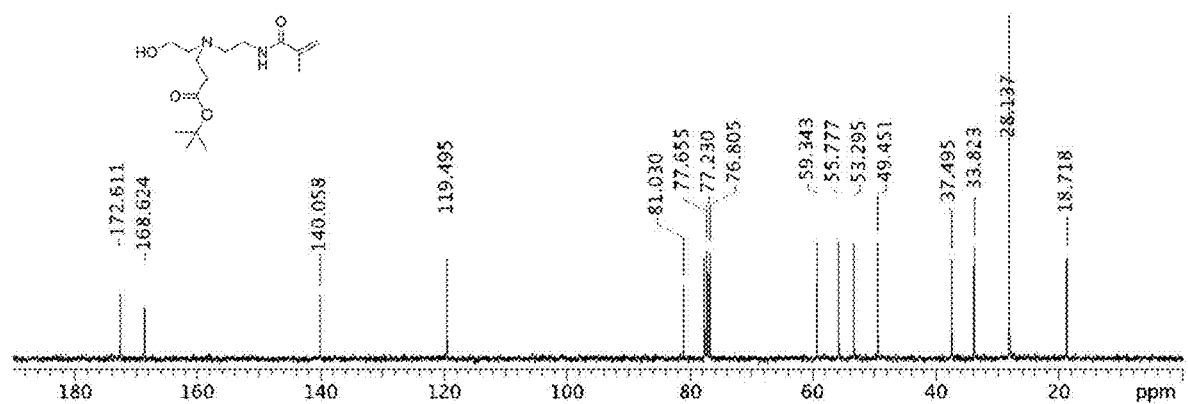
FIG. 21 is a $^{13}$C NMR Spectra of compound LV (75 MHz).

The synthesis procedures of Tert-butyl 3-((2-hydroxyethyl)(2-methacrylamidoethyl)amino)propanoate (compound LV) were similar to that of compound LIV describe in detail above except that tert-butyl acrylate was used instead of tert-butyl bromoacetate. The product was purified by silica gel column chromatography (ethyl acetate/hexane, 4/1 (v/v)). (Two-step yield: 33%). $^1$H NMR (300 MHz, CDCl$_3$) δ 6.78 (s, 1H), 5.67 (s, 1H), 5.24 (s, 1H), 3.52 (t, J=5.0 Hz, 2H), 3.34 (m, 2H), 3.11 (s, 1H), 2.71 (t, J=6.3 Hz, 2H), 2.56 (m, 4H), 2.32 (t, J=6.3 Hz, 2H), 1.90 (s, 3H), 1.38 (s, 9H) (See, FIG. 20). $^{13}$C NMR (75 MHz, CDCl$_3$) δ 172.61, 168.62, 140.06, 119.50, 81.03, 59.34, 55.78, 53.30, 49.45, 37.50, 33.82, 28.14, 18.72 (See, FIG. 21)

4. Synthesis of 2-((2-hydroxyethyl)(2-methacrylamidoethyl) (methyl)ammonio)acetate (LVI: CBMAA-1)

Figure 22:
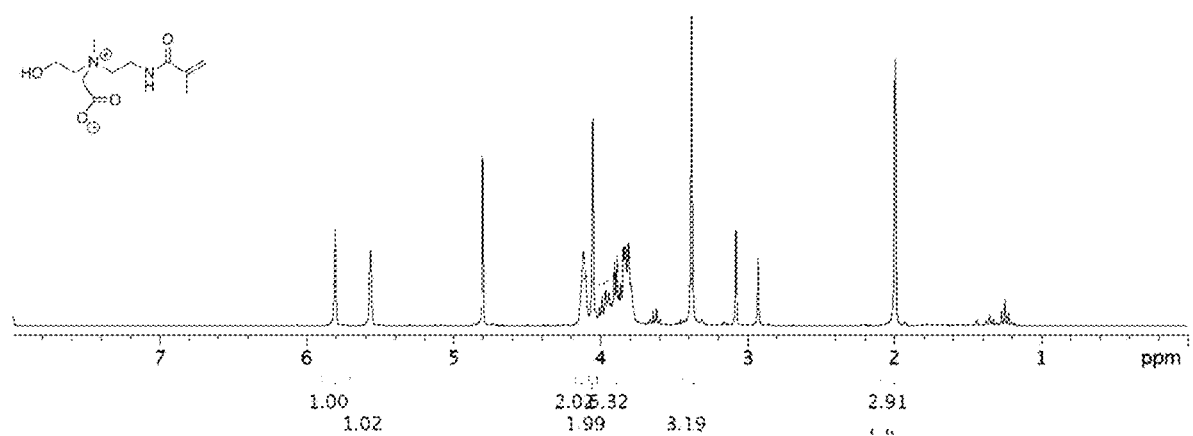
FIG. 22 is a $^1$H NMR Spectra of compound LVI (300 MHz).
Figure 23:
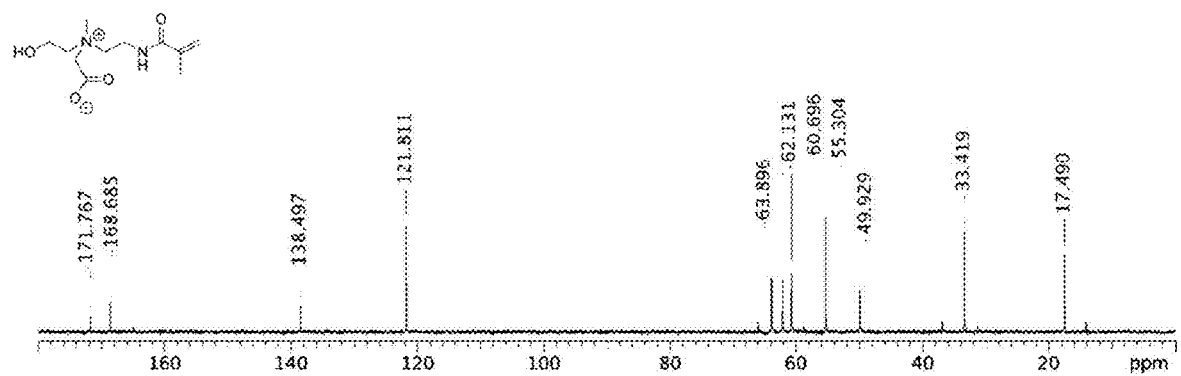
FIG. 23 is a $^{13}$C NMR Spectra of compound LVI (75 MHz).

10.3 g (0.036 mole) of compound LIV, synthesized as shown above, was dissolved in 75 mL of acetonitrile in a nitrogen filled flask, followed by adding 4 mL (0.05 mole) of CH$_3$I. The reaction solution was stirred at 60° C. under nitrogen for 24 hours. After solvent removal, the residue was precipitated in anhydrous diethyl ether and dried under vacuum. The obtained white solid was sequentially treated with a mixture of 15 mL TFA and 15 mL of dichloromethane for 1.5 hours at room temperature, concentrated with a rotary evaporator, precipitated in ether, dried under vacuum, redissolved in methanol, neutralized over an ion exchange resin (Amberlyst® A26, OH-form), and further purified by silica gel column chromatography (ethyl acetate/methanol 1/2 v/v) to provide 2-((2-hydroxyethyl)(2-methacrylamidoethyl)(methyl)ammonio)acetate (compound LVI) (CBMAA-1). (Yield: 73%). $^1$H NMR (300 MHz, D$_2$O) δ 5.81 (s, 1H), 5.56 (s, 1H), 4.11 (m, 2H), 4.05 (s, 2H), 4.01-3.80 (m, 6H), 3.38 (s, 3H), 1.99 (s, 3H) (See, FIG. 22). $^{13}$C NMR (75 MHz, D$_2$O) δ 171.77, 168.69, 138.50, 121.81, 63.90, 62.13, 60.70, 55.30, 49.93, 33.42, 17.49. (See, FIG. 23).

5. Synthesis of 3-((2-hydroxyethyl)(2-methacrylamidoethyl) (methyl)ammonio)propanoate (LVII: CBMAA-2)

Figure 24:
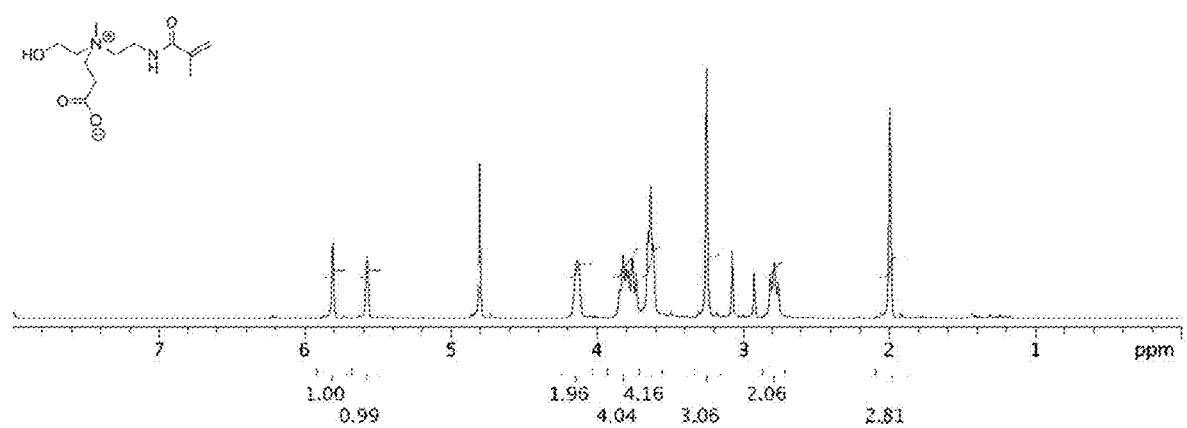
FIG. 24 is a $^1$H NMR Spectra of compound LVII (300 MHz).
Figure 25:
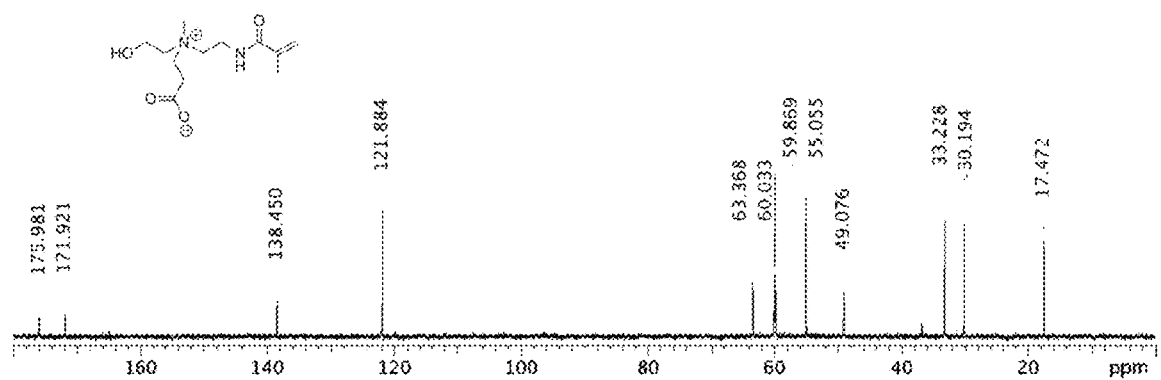
FIG. 25 is a $^{13}$C NMR Spectra of compound LVII (75 MHz).

3-((2-hydroxyethyl)(2-methacrylamidoethyl)(methyl)ammonio) propanoate (compound LVII) was synthesized following the same procedures as were used for 2-((2-hydroxyethyl)(2-methacrylamidoethyl) (methyl)ammonio)acetate (compound LVI). Pure product was obtained by silica gel column chromatography (ethyl acetate/methanol 1/2 v/v). (Yield: 70%). $^1$H NMR (300 MHz, D$_2$O) δ 5.81 (s, 1H), 5.57 (s, 1H), 4.13 (m, 2H), 3.82-3.72 (m, 4H), 3.65-3.63 (m, 4H), 3.25 (s, 3H), 1.99 (s, 3H). (See, FIG. 24). $^{13}$C NMR (75 MHz, D$_2$O) δ 175.98, 171.92, 138.45, 121.88, 63.37, 60.03, 59.87, 55.06, 49.08, 33.23, 30.19, 17.47 (See, FIG. 25).

6. 2D-NMR Spectrum for CBMAA-1 and CBMAA-2

Figure 26:
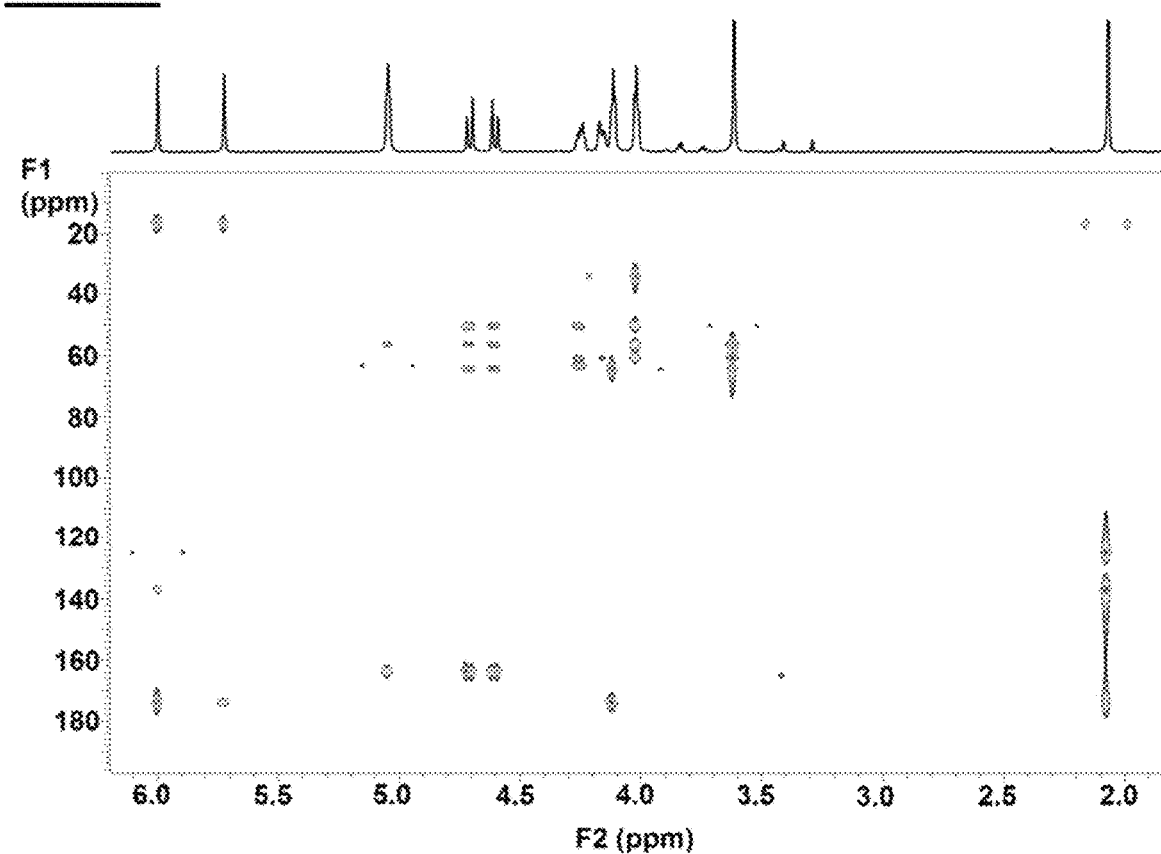
FIG. 26 is a 750 MHz $^1$H-$^{13}$C gHMBC NMR spectrum of CBMAA-1 in its cationic ring form. 2D-NMR can provide superior resolution and unique atomic connectivity information, so that unambiguous resonance assignment can be made for molecules.
Figure 27:
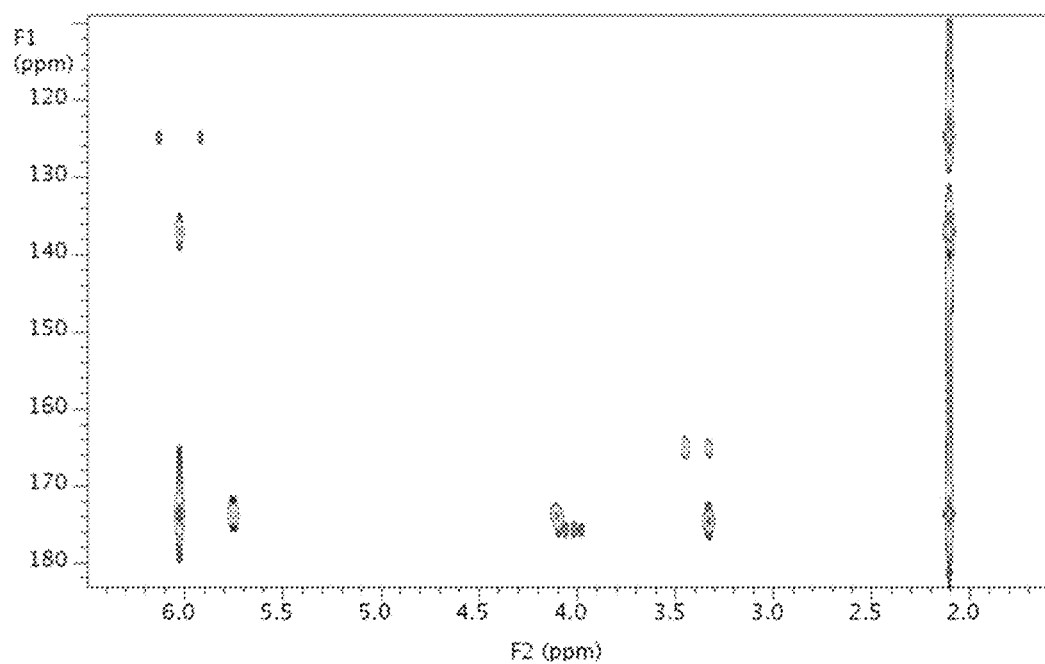
FIG. 27 is a 750 MHz $^1$H-$^{13}$C gHMBC NMR spectrum of CBMAA-2 as the evidence of seven membered ring formation in TFA.
Figure 28A:
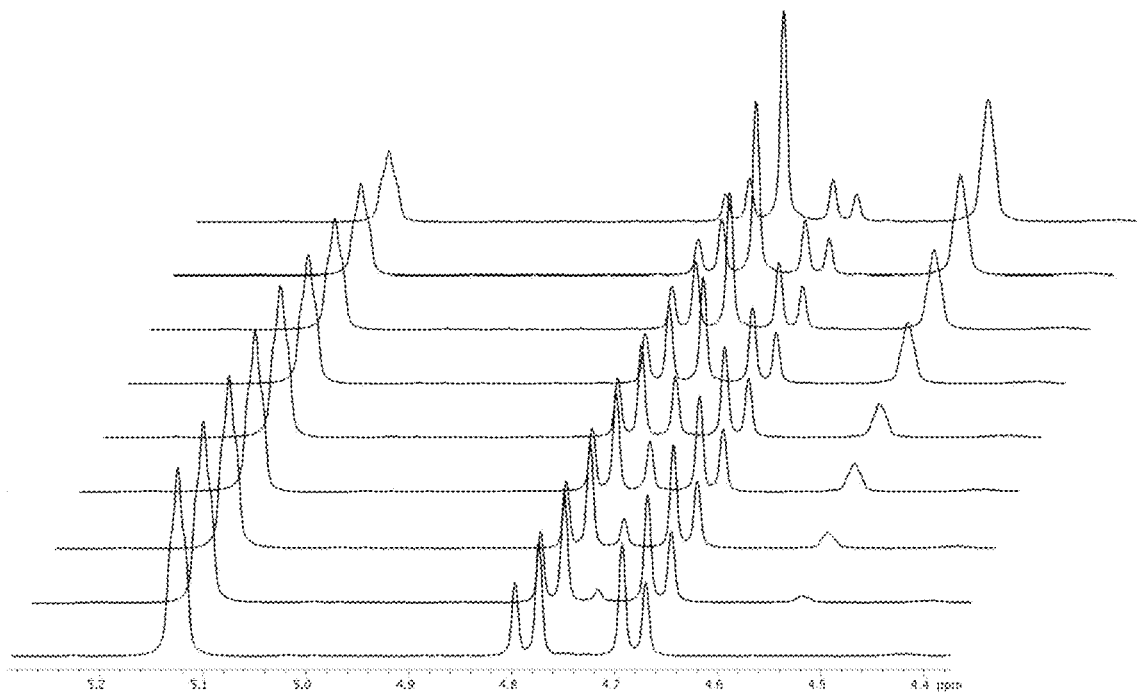
FIG. 28A-D are graphs showing changes in the NMR spectra of CBMAA-1 from zwitterionic form to its cationic ring form in TFA-d (28A); the conversion kinetics of zwitterionic CBMAA-1 from zwitterionic form to its cationic ring form in TFA-d (28B) and HAc-d (28C); and the conversion kinetics of cationic CBMAA-1 from ring form to its zwitterionic form in $D_2O$ (28D).
Figure 28B:
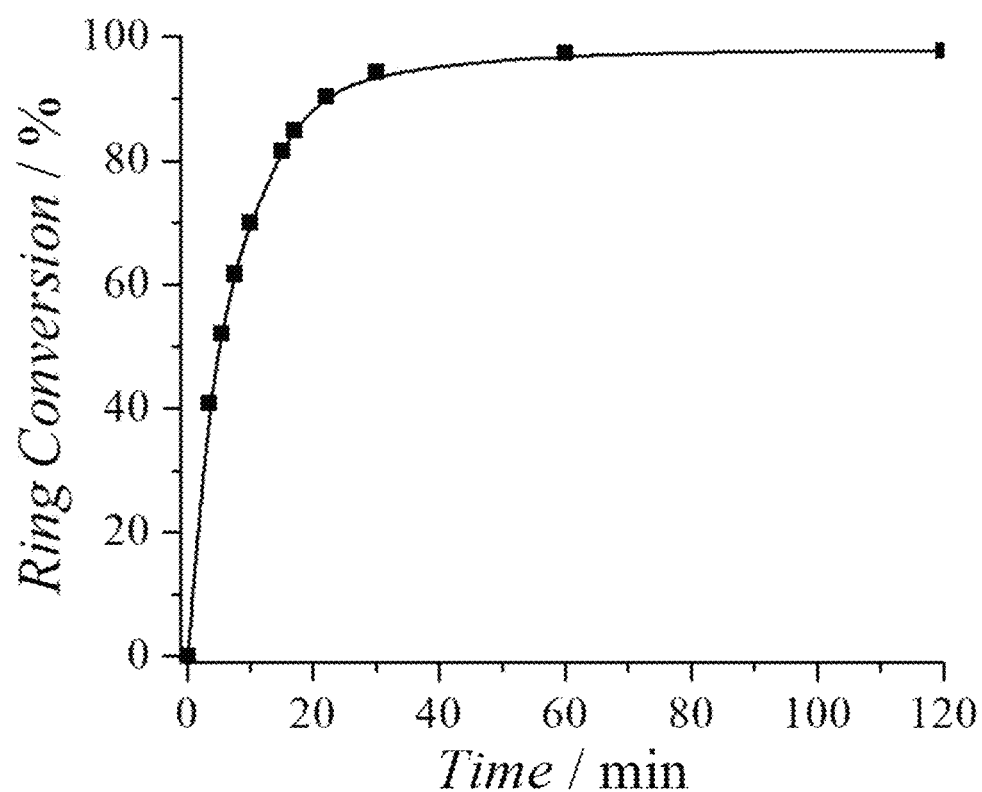
Figure 28C:
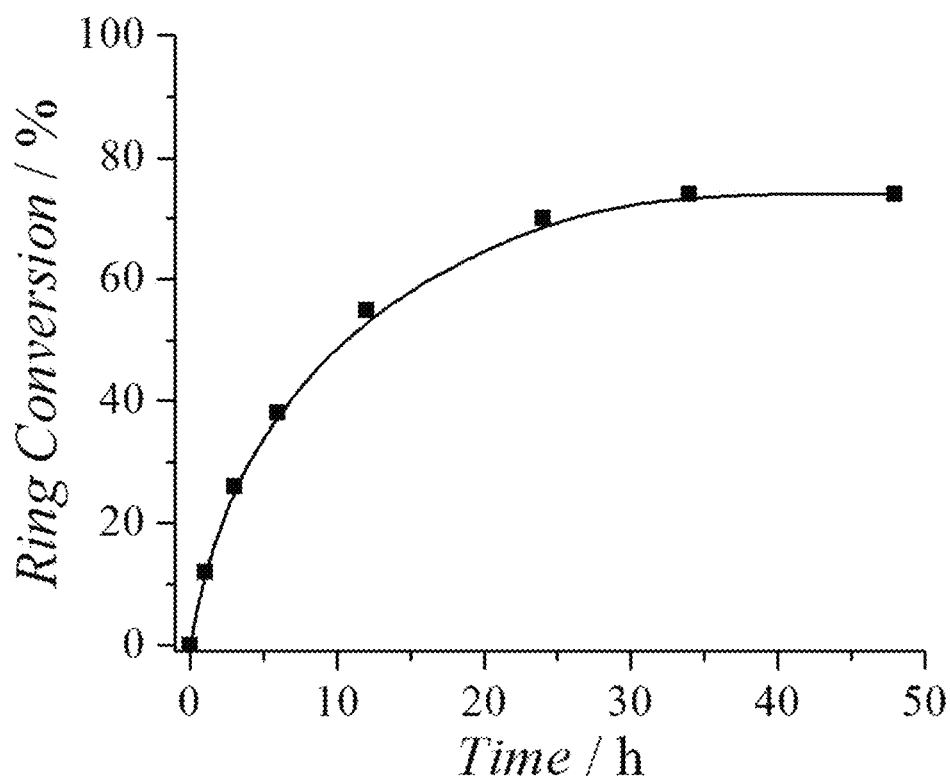
Figure 28D:
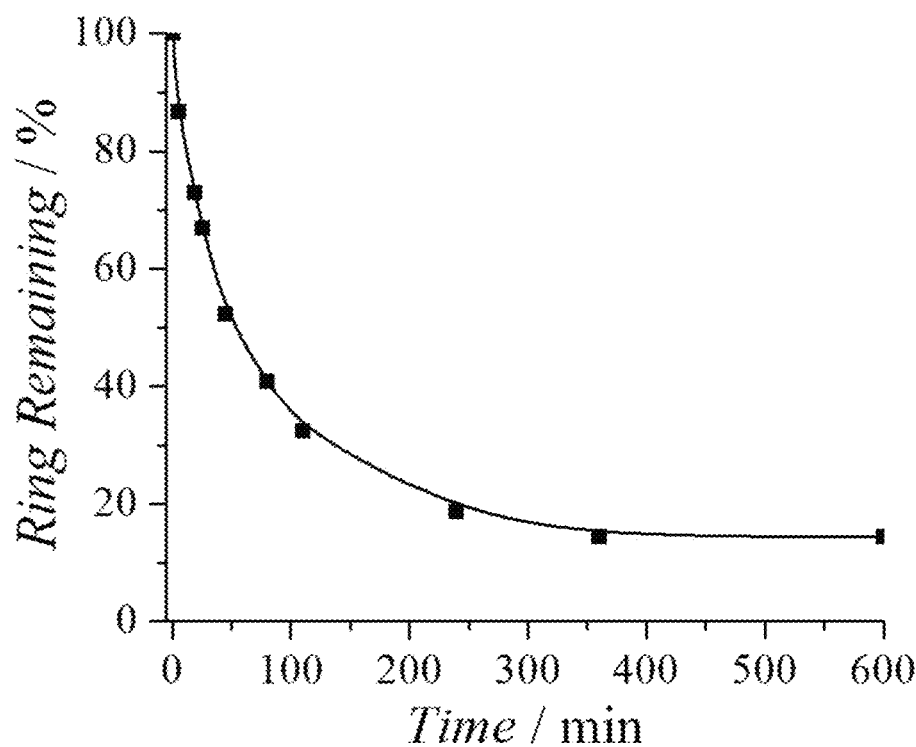

Heteronuclear multiple-bond correlation (gHMBC) 2D-NMR spectrum, which provides two- and three-bond correlations between $^1$H and $^{13}$C, were used to verify the ring structure formation of CBMAA-1 (FIG. 26) and to monitor whether there is the lactone ring formation for CBMAA-2 (FIG. 27) in TFA-d. CBMAA-1 formed six-membered lactone ring and showed well resolved correlations in the NMR spectrum, which is similar to the 2D-NMR spectrum of CBOH-1 shown in FIG. 1A. $^1$H NMR data shown in FIG. 28A were recorded at different time points to observe the dynamic ring formation process of CBMAA-1. The conversion ratio was calculated based on the integral value of vinylic protons in each form. As shown in FIG. 28B, 98% of CBMAA-1 converted into the six-membered ring form in TFA within an hour. In acetic acid FIG. 28C, a 70% conversion was achieved for CBMAA-1 within 24 hours. The ring opening kinetics (FIG. 28D) were studied by dissolving monomers in their cationic forms in pure D$_2$O. Calculations were performed with the same method as ring formation, and the final conversion was 86% for CBMAA-1 in 10 hours. In the case of CBMAA-2, seven-membered ring structure formation was also observed in TFA, but was at a much slower rate (after 52 hours) due to a higher ring strain upon closure.

Example 15

Synthesis of CBMA-2 and CBOH1

Carboxybetaine methacrylate (CBMA-2) was synthesized using previously published methods (See, e.g. B. Baroli, *J. Pharm. Sci.* 2007, 96, 2197, the disclosure of which is hereby incorporated by reference in their entirety and 2-((2-hydroxyethyl)(2-(methacryloyloxy)ethyl)(methyl)ammonio)acetate (CBOH-1) was synthesized as set forth in Example 1, above. CBMA-2 and CBOH-1 were used as controls.

Example 16

Monomer Stability Studies

Zwitterionic monomers may undergo two types of decomposition: Hofmann type elimination (side group elimination of quaternary ammonium) and side chain-backbone linkage hydrolysis; however, there is little attention on these possible and undesired transformations, which have a significant influence on the life and performance of the material. Schemes 6 and 7 show proposed mechanisms for eliminations of CBMAA-2 in acetic acid (Scheme 6) and Na$_2$CO$_3$ (Scheme 7) solutions.

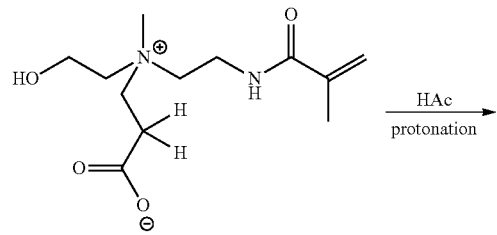

Scheme 6

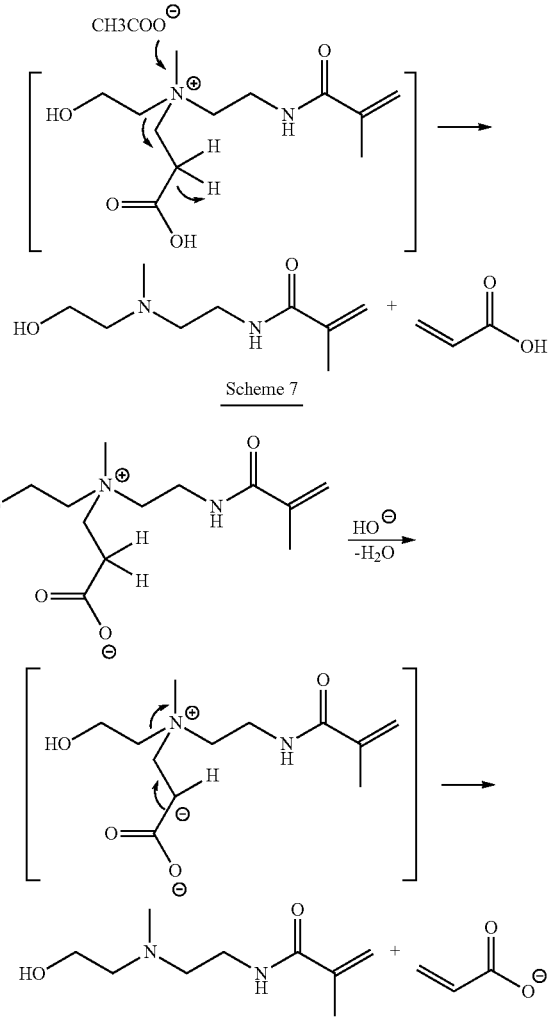

Scheme 7

Hofmann type elimination of quaternary ammoniums is commonly seen under basic conditions, but elimination under acidic conditions has been rarely reported. A systematic study of four monomers was carried out to investigate the effect of their structure on their stability in harsh acidic (pure HAc-d) and basic (0.2 M Na$_2$CO$_3$ solution, pH 12.1) conditions. In terms of elimination, monomers with one carbon spacer between carboxylate and quaternary ammonium, CBMAA-1 and CBOH-1, were very stable under both acidic (FIG. 3A) and basic (FIG. 3B) conditions, while CBMA-2 and CBMAA-2 bearing a two-carbon spacer underwent elimination in both conditions. The elimination reaction in HAc was relatively faster, compared to that in 0.2 M Na$_2$CO$_3$ solution. The elimination reaction of CBMA-2 and CBMAA-2 completed in ten days in HAc, while it took over twenty five days for the elimination reaction to finish in 0.2 M Na$_2$CO$_3$ solution. Although the carboxylate group in monomers with a two-carbon spacer are slightly easier to be further functionalized for conjugating other moieties, the monomer with one carbon spacer dramatically increases the stability of materials. The stability of a material is particularly important for long-term applications.

It was also found that the methacrylate groups were hydrolyzed completely within 7 hours in 0.2 M Na$_2$CO$_3$ solution, while methacrylamide group was still stable after 30 days under the same condition. The hydrolysis and elimination reactions occur simultaneously, but the rate of ester hydrolysis is much faster than that of Hofmann elimination. Hofmann elimination of CBMA-2 was observed after the completion of its hydrolysis. It should be noted that decomposition kinetics of monomers might be different from that of polymers. We expect that the hydrolysis and elimination reactions occur at slower rates in polymers than corresponding monomers due to steric hindrance. The CBMAA-1 monomer demonstrated the highest stability under both harsh acidic and basic conditions.

CBMAA-2 was chosen as a model molecule to further study elimination mechanisms of carboxybetaine-based compounds. Under acidic conditions, nucleophilicity of the negatively charged acetate anion could be the reason of elimination reaction. CBMAA-2 may undergo elimination via the mechanism described in Scheme 6 The superior electronegative nature of —$CF_3$ group makes TFA a 100,000-fold stronger acid than HAc; however the nucleophilicity of trifluoroacetate anion is much lower. This mechanism can explain why the slow seven-membered ring formation of CBMAA-2 was observed but there was no elimination detected in TFA. Under basic conditions, the hydrogen's acidity of the beta carbon is important for possible elimination reactions, since protons adjacent to carbonyl groups are more acidic than other proton. The proposed mechanism is illustrated in Scheme 7. Theoretically, any side group of the quaternary ammonium may undergo elimination reactions; however, the resonance stabilized carboxylate make it a thermodynamically favored leaving group in this case (this may apply to both acidic and basic conditions). Thus only one tertiary amine product, (N-(2-((2-hydroxyethyl)(methyl)amino)ethyl)methacrylamide), was observed and isolated. See Scheme 7, above.

Example 17

Synthesis of Polymer Brushes Using Surface-Initiated Photoiniferter-Mediated Polymerization (si-PIMP)

Polymer brushes were synthesized via Photoiniferter-Mediated Polymerization (si-PIMP). The photoiniferter, 11-mercaptorundecane-1-[4-(phenyl)carbamate] (DTCA), was synthesized following the procedure reported previously. See Benetti E M, Zapotoczny S, Vancso J. Tunable thermoresponsive polymeric platforms on gold by "photoiniferter"-based surface grafting. Adv Mater 2007; 19:268-71, the disclosure of which is hereby incorporated by reference in its entirety. The photoiniferter self-assembled monolayer (SAM) was formed by soaking cleaned chips in 1 mM photoiniferter in THF overnight at room temperature. Chips were then rinsed with THF and dried with filtered air. One of treated chips was placed in a quartz reaction tube under nitrogen. 10 mL of a monomer solution (50 mg/mL) in PBS was deoxygenated via nitrogen purge. The deoxygenated monomer solution was transferred into the reactor via a syringe and then irradiated with a 302 nm UV lamp (UVP, model UVM-57) coupled with a 280 nm cutoff filter for 2 hours. After the reaction, the chip was rinsed with water and ethanol, and then stored in PBS before use.

Example 18

Preparation of Hydrogels of pCBMA, pCBMAA-1, and CBMAA-2 for Antimicrobial Testing To prepare hydrogels for antimicrobial test, CBMAA-1 monomer was equilibrated in pure acetic acid to obtain above 70% conversion of its cationic ring form. After checked the conversion ratio with NMR, the monomer was precipitated in ether, vacuum dried, and then photopolymerized in DMSO. The reaction solution contains 1.5 M monomer, 0.045 M carboxybetaine dimethacrylate as a cross-linker and 0.5 wt % 2-hydroxy-2-methylpropiophenone, as an photoinitiator. The solution was transferred into a mold made of two quartz slides separated by an 2 mm thick PTFE spacer and polymerized under UV (362 nm) for 1 hour. The gel was immersed in acetonitrile for 2 days. Before the antimicrobial study, the gel was equilibrated in water for 2 hours to obtain hydrogels. Because of the poor solubility of CBMA in organic solvents and instability of CBMAA-2 in its ring form, pCBMA and pCBMAA-2 hydrogels were prepared in their zwitterionic form at the same concentration with the same method in $H_2O$. The wet weight of the hydrogel sample was measured after the removal of excess water. Dry weight was recorded after the samples had been freeze-dried for 48 hours. The water contents of hydrogels (as a percent) are calculated by (Wet weight−Dry weight)/Wet weight×100% and the results reported on Table 4, below.

Example 19

Hydrogel Compression and Tensile Strength Tests for CBMAA-1, CBMAA-2, CBMA-2, and CBOH1 Monomers Hydrogels for compression and tensile tests were prepared with CBMAA-1, CBMAA-2, CBMA-2, and CBOH1 monomers (zwitterionic form) at the same concentration in water. At least five disks of each kind of hydrogel (about 2 mm thickness when swell to equilibrium in water) were compressed to failure at a rate of 0.5 mm $min^{-1}$ using an Instron 5543 mechanical tester (Instron, Norwood, Mass.) with a 100 N load cell. For tensile test, hydrogel samples were cut into rectangular shapes of about 15 mm in width, 40 mm in length, and 2-3 mm in thickness. All samples were pulled to failure at a rate of 0.1 mm $s^{-1}$ using a TA.XT Plus Texture Analyzer (Texture Technologies, Scarsdale, N.Y.) with a 500 g load cell. See FIGS. 29A, 29B.

Figure 29A:
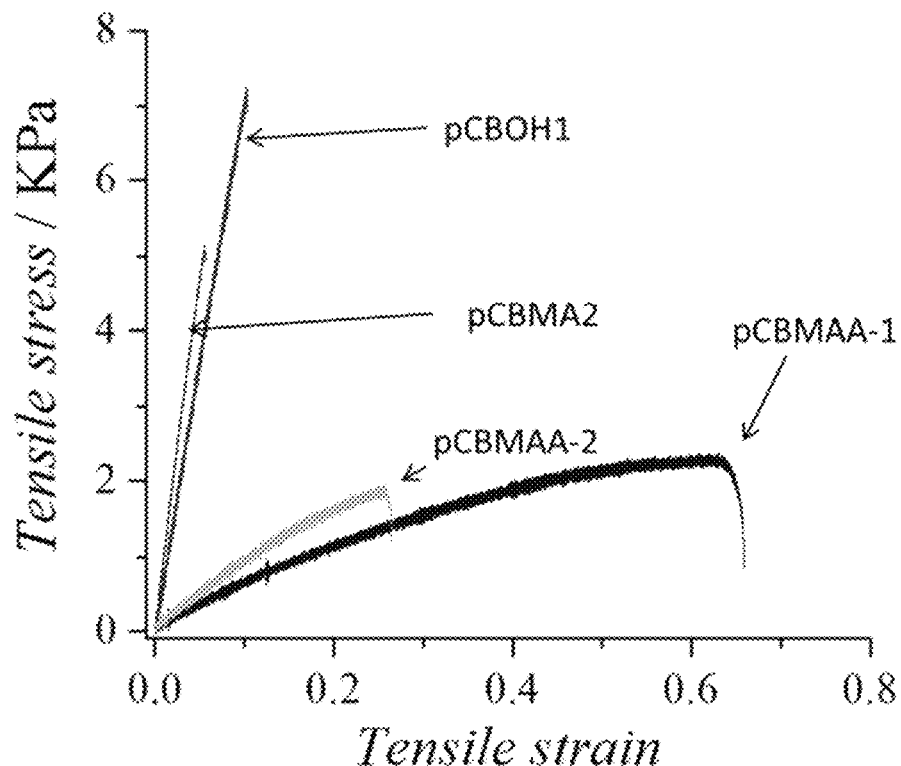
FIG. 29A-B are graphs showing the results of tensile (29A) and compression (29B) studies for pCBMAA-1, pCBMAA-2, pCBOH-1, and pCBMA-2 hydrogels prepared at 1.5 M.
Figure 29B:
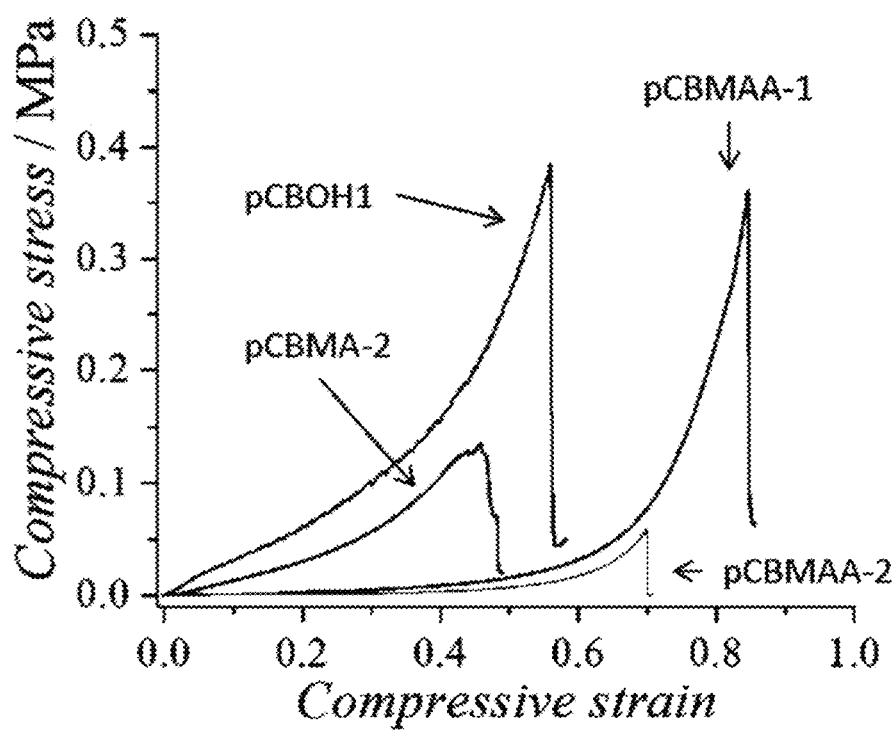

As shown in FIGS. 29A, 29B, pCBMAA-1 hydrogel shows typical elastomeric stress-strain curves with low Young's modulus and high yield strain, in both tensile and compression test. About 65% tensile strain and 85% compressive strain were achieved for this hydrogel. In the tensile study, the breaking strain of pCBMAA-1 hydrogel is increased 11-fold and 6-fold compared to pCBMA-2 and pCBOH-1 hydrogels respectively. The compressive breaking strain of pCBMAA-1 hydrogel has 1.8-fold and 1.5-fold increases compared to pCBMA-2 and pCBOH-1 hydrogels respectively and its compressive breaking stress is comparable to that of pCBOH-1 hydrogel. Our results indicate that pCBMAA-1 hydrogel is stronger in compression and much more elastic in tensile than existing zwitterionic hydrogels. pCBMAA-2 hydrogel also shows an improved elasticity, but the change is not as dramatic as pCBMAA-1 hydrogel. Higher equilibrium water content (EWC) (See, Table 4) and swelling ratio of pCBMAA-2 may be the cause of the lower elasticity than that of pCBMAA-1 hydrogels.

TABLE 4

Equilibrium water content of hydrogels (average of 3 samples

|  | pCBMAA-1 | pCBMAA-2 | pCBOH-1 | pCBMA-2 |
|---|---|---|---|---|
| Water content of hydrogel (1.5M) | 94.3% | 97.8% | 84.2% | 90.6% |

Example 20

Analysis of Protein Adsorption for pCBMAA-1 and pCBMAA-2 Polymer Brushes

A four-channel SPR sensor was used to measure protein adsorption on pCBMAA-1 and pCBMAA-2 polymer brushes. First, PBS solution at 50 μL min' flow rate was used to obtain a baseline signal. 1 mg mL$^{-1}$ bovine fibrinogen solution, 100% human blood plasma or 100% human serum was then injected for 10 minutes followed by a PBS wash to remove any loosely bound proteins. The amount of adsorbed proteins was calculated as the change in wavelength before and after protein injection. See FIGS. 7A, 7B.

Example 21

Measurement of the Film Thickness for pCBMAA-1 and pCBMAA-2

The film thickness was measured by Ellipsometry as ~18.07 nm for pCBMAA-1 and ~9.26 nm for pCBMAA-2. The protein-resistant properties of pCBMAA-1 and pCBMAA-2 polymer brushes were characterized by SPR sensor on gold-coated sensor chips using human fibrinogen (1 mg mL$^{-1}$), 100% human blood plasma and 100% human blood serum. The results are shown in FIGS. 7A and 7B.

Example 22

Bacterial Attachment, Viability and Releasing Test for CBMAA-1 and CBMAA-2 Hydrogels

*Escherichia coli* K12 was cultured at 37° C. in Luria-Bertani (LB) medium (20 g L$^{-1}$) to reached an optical density of 0.8 at 600 nm. After three wash with phosphate buffered saline (PBS), cells were suspended in PBS to get a final concentration of 5×10$^7$ cells mL$^{-1}$. 50 μL of fresh *E. coli* suspension in PBS was pipetted onto CBMAA-1 and CBMAA-2 hydrogel discs (8 mm in diameter) and incubated at room temperature for 1 hour. To analyze the density of bacteria accumulated on hydrogel surfaces, samples were gently rinsed with water, and stained with LIVE/DEAD BacLight bacterial viability assay kit. After the staining, the number of live and dead cells was determined with an Olympus IX81 fluorescent microscopy (Olympus, Japan) with 60× oil lens through FITC and Cys3 filters. Following imaging, the sample was placed in PBS solution for 16 hours. The number of remaining *E. coli* was again determined by the fluorescent microscopy. Three separate samples were analyzed for each hydrogel sample. See FIGS. 30A-D and Table 5, below.

TABLE 5

Bacteria attachment, viability and releasing test of hydrogel surfaces (n = 3).

|  | pCBMAA-1 | pCBMAA-2 | pCBMA-2 |
|---|---|---|---|
| Cell density before hydrolysis (cells cm$^{-2}$) | 1.0 ± 0.1 E6 | 8.3 ± 2.3 E4 | 4.0 ± 0.9 E4 |
| Cell density after hydrolysis) (cells cm$^{-2}$) | 4.4 ± 2.1 E4 | 3.5 ± 1.1 E4 | 4.9 ± 1.2 E4 |
| Antimicrobial efficiecy (%) | >99.5 | — | — |

Figure 30:
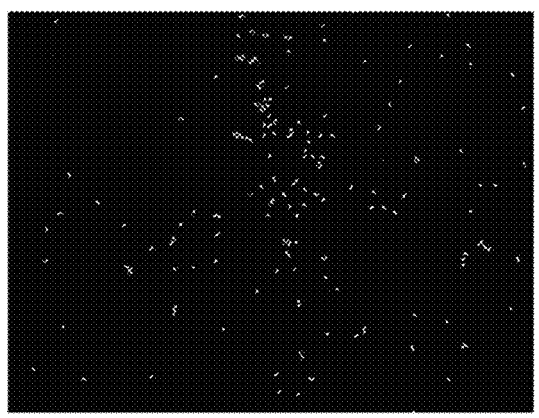
FIG. 30A-D are representative fluorescence microscopy images of bacterial attachment on pCBMAA-1 in cationic form (30A), pCBMAA-2 (30B), and pCBMA-2 (30C) hydrogels before hydrolysis and on pCBMAA-1 in zwitterionic form (30D), after 16 hours hydrolysis in PBS. Bacterial cells were stained with LIVE/DEAD BacLight Bacterial Viability assay kit.
Figure 30:
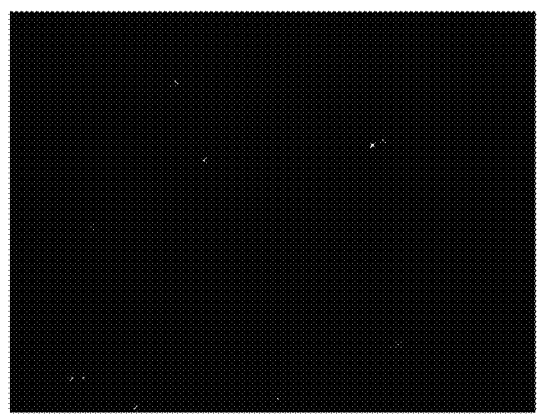
Figure 30:
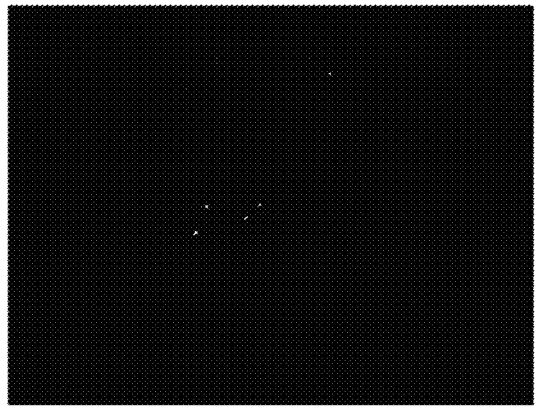
Figure 30:
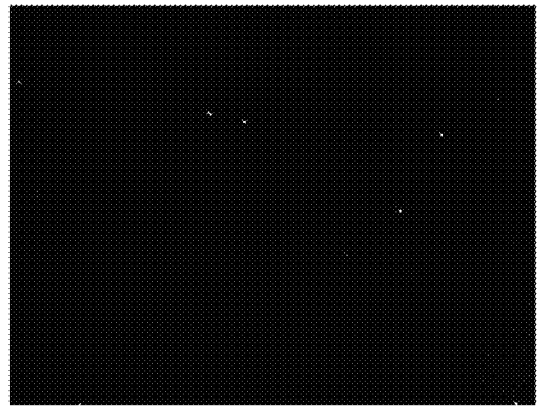
Figure 31:
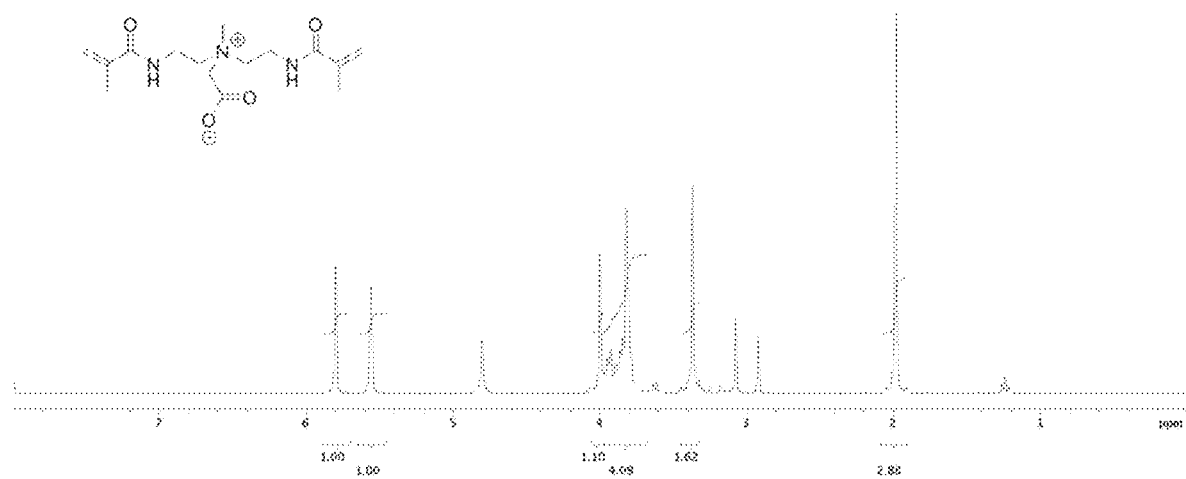
FIG. 31 is a $^1$H NMR spectrum of 2-(bis(2-methacrylamidoethyl)(methyl)ammonio)acetate at 300 MHz, $D_2O$.
Figure 32:
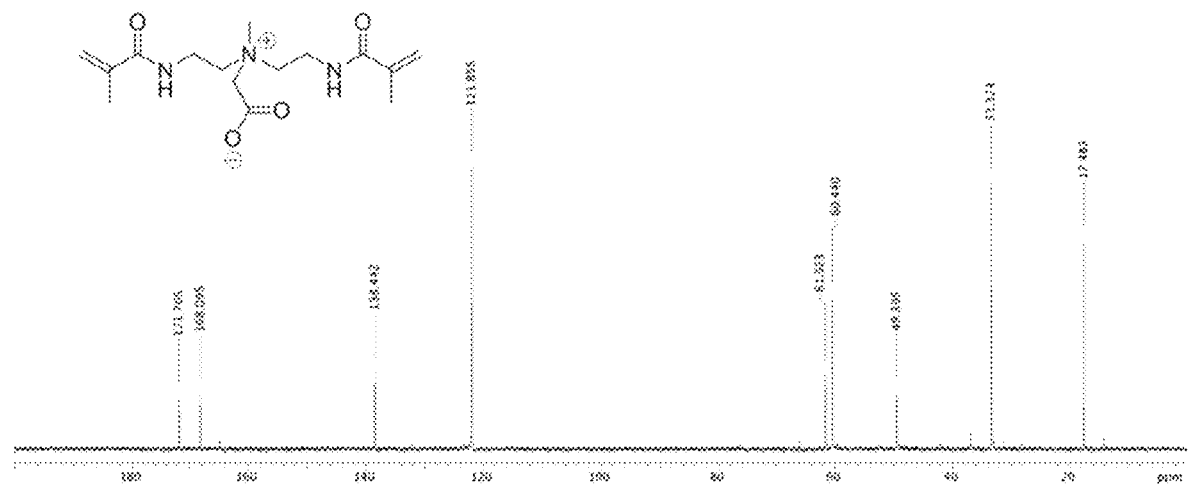
FIG. 32 is a $^{13}$C NMR of 2-(bis(2-methacrylamidoethyl)(methyl)ammonio)acetate spectrum at 300 MHz, $D_2O$.

CBMAA-1, in particular, showed good switchability and ring stability. The ability of catch, kill and release of *E. coli* K12 was tested on pCBMAA-1 hydrogel surfaces before and after hydrolysis with zwitterionic pCBMAA-2 and pCBMA-2 hydrogels as both negative antimicrobial control and positive antifouling control. As shown in FIG. 30, a large amount of bacteria were caught on cationic pCBMAA-1 (ring form) hydrogel surfaces before hydrolysis, whereas only few bacterial cells were found on the zwitterionic pCBMAA-2 and pCBMA-2 surfaces. pCBMAA-1 hydrogel in the cationic ring form could effectively catch and cause the membrane damage of *E. coli* K12 within 1 hour compared to zwitterionic pCBMAA-2 and pCBMA-2 hydrogel surfaces, since positively charged compounds can interrupt the membrane integrity of microorganisms and cause the death of cells. Zwitterionic pCBMAA-2 and pCBMA-2 surfaces had fewer attached cells and they were not able to kill attached cells. Quantitative results are shown in Table 2. The surface density of attached *E. coli* on cationic pCBMAA-1, zwitterionic pCBMAA-2 and pCBMA-2 hydrogels were 1.0×10$^6$, 8.3×10$^4$ and 4.0×10$^4$ cells cm$^{-2}$ respectively. After overnight hydrolysis, pCBMAA-1 surfaces released 95% of attached cells. The results demonstrate that pCBMAA-1 hydrogels in its ring form can kill bacteria and then release killed bacteria via hydrolysis and that zwitterionic pCBMAA-2 and pCBMA-2 hydrogels can effectively resist bacterial adhesion.

Example 24

Synthesis of Compound XXXII (2-(bis(2-methacrylamidoethyl)(methyl)ammonio)acetate)

The novel crosslinker 2-(bis(2-methacrylamidoethyl) (methyl)ammonio) acetate was synthesized using the three step reaction procedure shown in Scheme 8 and described below.

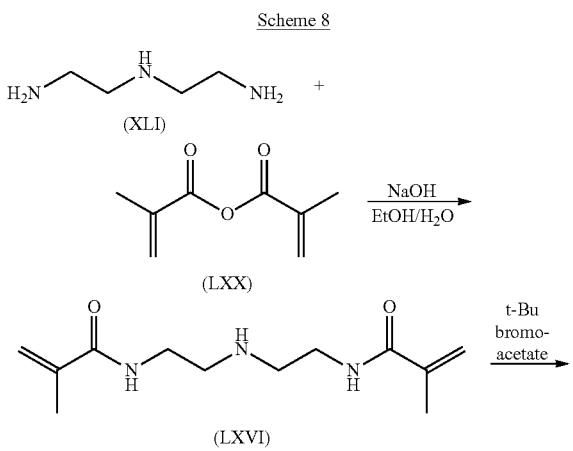

Scheme 8

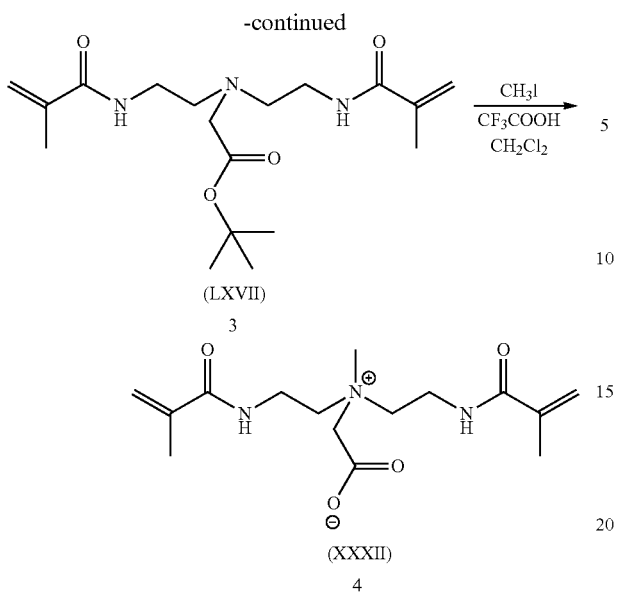

(LXVII)
3

(XXXII)
4

1. Synthesis of Compound 2 (N,N'-(azanediylbis(ethane-2,1-diyl)) bis(2-methylacrylamide))

5.2 g (0.13 mol) of NaOH was dissolved in a mixture of 40 mL of de-ionized water and 70 mL of absolute ethanol in a 250 mL three-necked round bottom flask, followed by 5.4 mL (50 mmol) of diethylenetriamine. The mixture was cooled down to 0° C. with an ice bath. 17.1 mL (0.12 mol) of methacrylic anhydride was added dropwise with a dropping funnel under a positive nitrogen flow. After stirring at 0° C. for 2 hours, the reaction was stirred at room temperature for 3 hours. The crude product was used directly for the next reaction without purification.

2. Synthesis of Compound 3 (tert-butyl bis(2-methacrylamidoethyl)glycinate)

7.38 mL (50 mmol) of tert-butyl bromoacetate was added into the mixture of the crude compound 2 and heated overnight at 60° C. under nitrogen with stirring. Another eqv. Of NaOH was added after stirring overnight. Ethanol was removed with a rotary evaporator, and the pH value was adjusted to ~10 with NaOH. After extraction with ethyl acetate twice, the organic phase was washed by water and dried with anhydrous magnesium sulfate. After filtration, the liquid was concentrated and purified by silica gel column chromatography (ethyl acetate/hexane, 4/1 (v/v)). (Two-step yield: 32%).

3. Synthesis of Compound 4 (2-(bis(2-methacrylamidoethyl)(methyl)ammonio)acetate)

4.8 g (13.6 mmol) of compound 3 was dissolved in 50 mL of acetonitrile in a nitrogen filled flask, followed by adding 1.7 mL (27.2 mmol) of $CH_3I$. The reaction mixture was stirred at 60° C. under nitrogen for 24 hours. After solvent removal, the residue was precipitated in anhydrous diethyl ether and dried under vacuum. The obtained white product was sequentially treated with a mixture of 6 mL TFA and 6 mL of dichloromethane for 2 hours at room temperature, concentrated with a rotary evaporator, precipitated in anhydrous diethyl ether, dried under vacuum, re-dissolved in methanol, neutralized over an ion-exchange resin (Amberlyst A26, OH form) and further purified by silica gel column chromatography (ethyl acetate/methanol 2/1 v/v). (Yield: 76%).

What is claimed is:

1. A zwitterionic composition having anti-fouling and antimicrobial properties comprising:
   a polymer backbone formed from monomers selected from the group consisting of acrylates, methacrylates, acrylamides, methacrylamides, vinyl alcohols, serines and combinations thereof;
   one or more zwitterionic moieties chemically bonded to said polymer backbone, said zwitterionic moieties further comprising a carboxybetaine group having at least one ethanol, propanol, butanol or pentanol group bonded to the nitrogen atom of said carboxybetaine group; and
   a crosslinking compound.

2. The zwitterionic composition of claim 1 wherein said polymer backbone is selected from the group consisting of polymethacrylate, polyethylacrylate, polymethacrylamide, polyethylacrylamide poly(2-hydroxyethyl methacrylate), polyserine, polyvinyl alcohol, and combinations thereof.

3. The zwitterionic composition of claim 1 wherein said one or more zwitterionic moieties have a formula selected from the group consisting of:

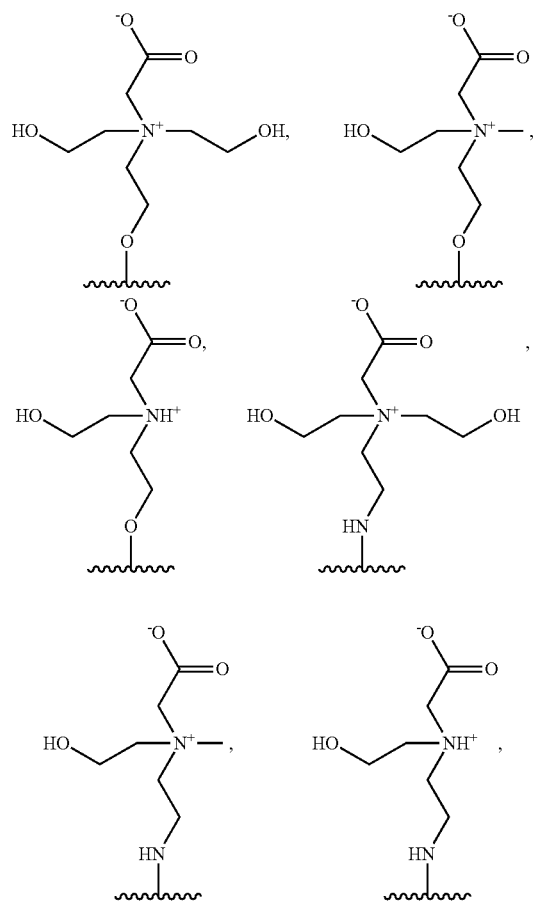

-continued

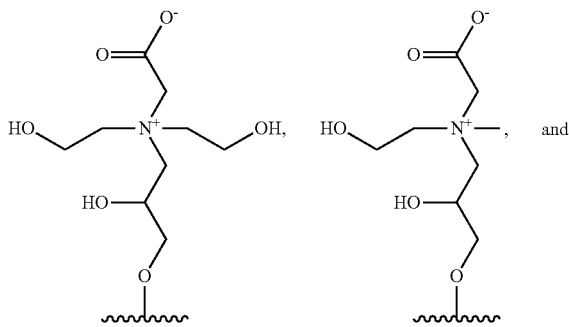

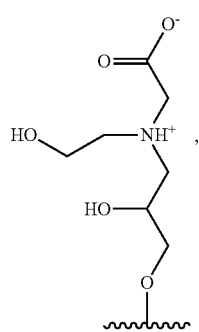

wherein ~ is the polymer backbone.

4. The zwitterionic composition of claim 1 having the formula:

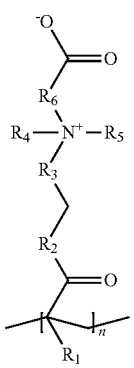

wherein $R_1$ is H, —$CH_3$ or —$CH_2CH_3$; $R_2$ are O or NH; $R_3$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$, or —$CH_2CH_2CH_2CH_2CH_2OH$; $R_5$ is H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or $CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$— and n is an integer from 2 to 10,000.

5. The zwitterionic composition of claim 1 wherein said one or more zwitterionic moieties have a formula:

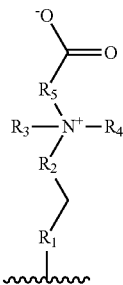

wherein $R_1$ is O or NH; $R_2$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_3$ is —$CH_2CH_2OH$, —$CH_2CH_2CH_2OH$, —$CH_2CH_2CH_2CH_2OH$, or —$CH_2CH_2CH_2CH_2CH_2OH$; $R_4$ is H, —$CH_3$, $CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, —$CH_2CH_2CH_2CH_2CH_2OH$; $R_5$ is —$CH_2$—, —$CH_2CH_2$—, —$CH_2CH_2CH_2$—, —$CH_2CH_2CH_2CH_2$—, or —$CH_2CH_2CH_2CH_2CH_2$— and ~ is the polymer backbone.

6. The zwitterionic composition of claim 1 wherein said one or more zwitterionic moieties have a formula:

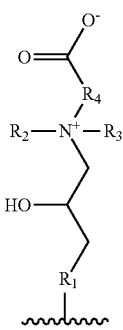

wherein $R_1$ is O or NH; $R_2$ is —$CH_2CH_2OH$, —$CH_2CH_2CH_2OH$, —$CH_2CH_2CH_2CH_2OH$, or —$CH_2CH_2CH_2CH_2CH_2OH$; $R_3$ is H, —$CH_3$, $CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$, $R_4$ is —$CH_2$—, —$CH_2CH_2$—, —$CH_2CH_2CH_2$—, —$CH_2CH_2CH_2CH_2$—, or —$CH_2CH_2CH_2CH_2CH_2$—; and ~ is the polymer backbone.

7. The zwitterionic composition of claim 1 wherein said one or more zwitterionic moieties have the formula:

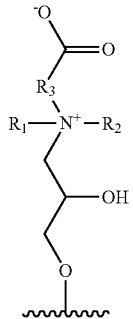

wherein $R_1$ is —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_2$ are H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_3$ is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—; and ∼∼∼ is the polymer backbone.

8. The zwitterionic composition of claim 1 wherein said one or more zwitterionic moieties are selected from the group consisting of 2-(bis(2-hydroxyethyl)(methylene)ammonio)acetate, 2-((2-hydroxyethyl)(methylene)(methyl)ammonio)acetate, 2-((2-hydroxyethyl)(methylene)ammonio) acetate, 3-(bis(2-hydroxyethyl)(methylene) (methyl) ammonio)propanoate, 3-((2-hydroxyethyl)(methylene) (methyl)ammonio)propanoate, 3-((2-hydroxyethyl)(methylene)ammonio) propanoate and combinations thereof.

9. A chemical composition comprising the zwitterionic composition of claim 1 wherein said each of the one or more zwitterionic moieties has a corresponding cationic ring form.

10. The chemical composition of claim 9 wherein the cationic ring form has the formula:

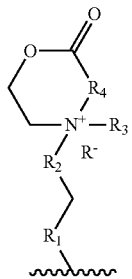

wherein $R_1$ is O or NH; $R_2$ is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—; $R_3$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH; $R_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—; R is any organic or inorganic anion; and ∼∼∼ is the polymer backbone.

11. The chemical composition of claim 9 wherein the cationic ring form of said one or more zwitterionic moieties has the formula:

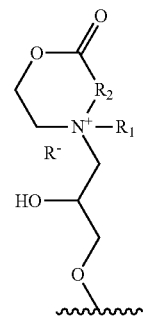

wherein $R_1$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_2$ is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—; R is any organic or inorganic anion; and ∼∼∼ is the polymer backbone.

12. The chemical composition of claim 9 wherein the cationic ring form of the one or more zwitterionic moieties has a formula selected from the group consisting of:

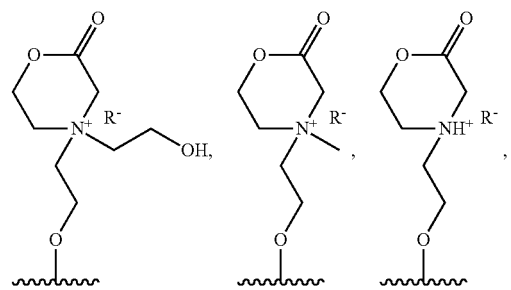

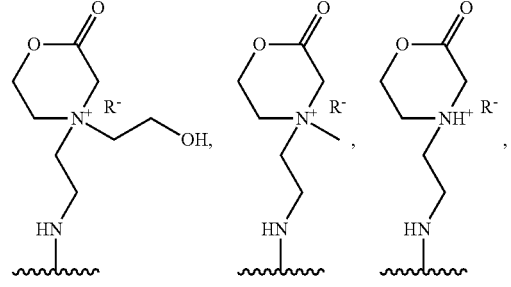

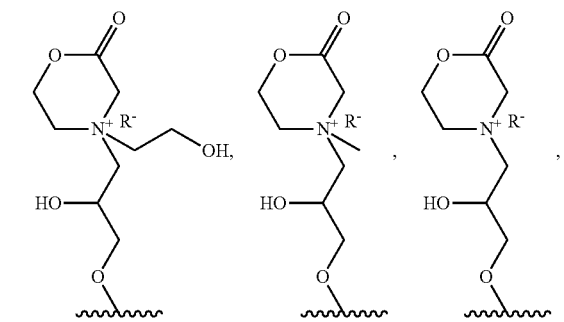

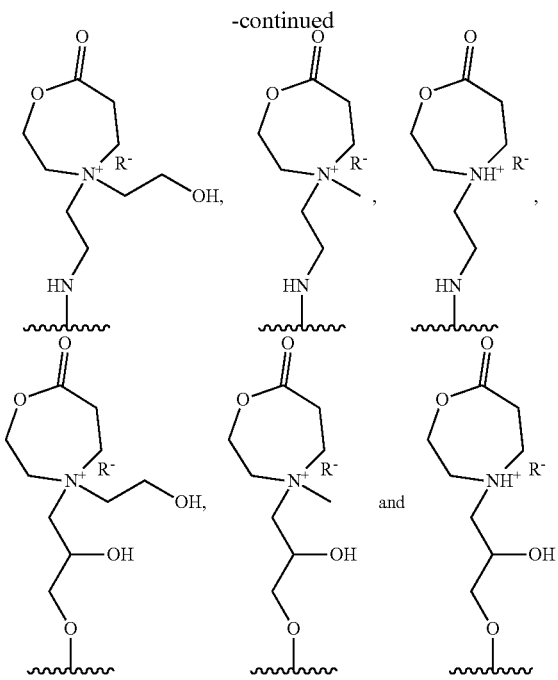

wherein R⁻ is any organic or inorganic anion and ⁓ is the polymer backbone.

13. The zwitterionic composition of claim 1 wherein said crosslinking compound comprises a compound selected from the group consisting of di(methyl)acrylate, multi-(methyl)acrylate, di(methyl)acrylamide, multi-(methyl)acrylamide, diepoxide, multi-epoxide, dithiol and multi-thiol, and combinations thereof.

14. The zwitterionic composition of claim 1 wherein said crosslinking compound has the formula:

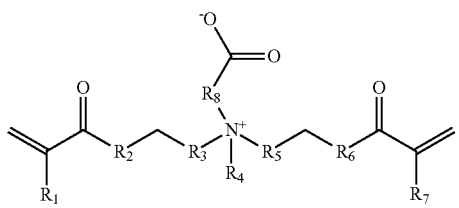

wherein $R_1$ and $R_7$ are —H, —$CH_3$, or —$CH_2CH_3$; $R_2$ and $R_6$ are O or NH; $R_3$ and $R_5$ are —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$—H, $CH_3$, $CH_2CH_3$, —$CH_2CH_2CH_3$, —$CH_2CH_2CH_2CH_3$, $CH_2CH_2OH$, —$CH_2CH_2CH_2OH$, —$CH_2CH_2CH_2CH_2OH$, or —$CH_2CH_2CH_2CH_2CH_2OH$; and $R_8$ is —$CH_2^-$, —$CH_2CH_2^-$, —$CH_2CH_2CH_2^-$, —$CH_2CH_2CH_2CH_2$—, or —$CH_2CH_2CH_2CH_2CH_2$—.

15. The zwitterionic composition of claim 1 wherein said one or more crosslinking compound is selected from the group consisting of carboxybetaine di(methyl)acrylate, carboxybetaine di(methyl)acrylamide, poly(ethylene glycol) di(methyl)acrylate, 1,3-propanedithiol, 1,4-butanedithiol, 1,3-butadiene diepoxide, and combinations thereof.

16. The zwitterionic composition of claim 1 wherein said one or more crosslinking compound has the formula:

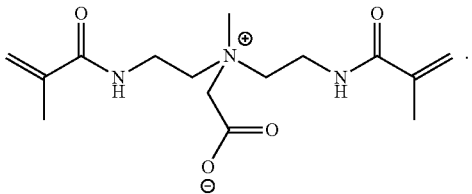 [SMILES: C=C(C)C(=O)NCC[N+](C)(CCNC(=O)C(=C)C)CC(=O)[O-]]

17. A carboxybetaine-based composition having antifouling and antimicrobial properties comprising:
a zwitterionic polymer selected from the group consisting of poly(2-((2-hydroxyethyl)(2-methacrylamidoethyl)(methyl)ammonio)acetate), poly(3-((2-hydroxyethyl)(2-methacrylamidoethyl)(methyl)ammonio)propanoate), poly(2-((2-hydroxyethyl)(2-(methacryloyloxy)ethyl)(methyl)ammonio)acetate) and poly(2-(bis(2-hydroxyethyl)(2-(methacryloyloxy)ethyl)ammonio)acetate) and combinations thereof; and
a crosslinker.

18. The carboxybetaine composition of claim 17 wherein the crosslinker selected from the group consisting of carboxybetaine di(methyl)acrylate, carboxybetaine di(methyl)acrylamide, poly(ethylene glycol) di(methyl)acrylate, 1,3-propanedithiol, 1,4-butanedithiol, 1,3-butadiene diepoxide, and combinations thereof.

19. The zwitterionic composition of claim 17 wherein said one or more crosslinker has the formula:

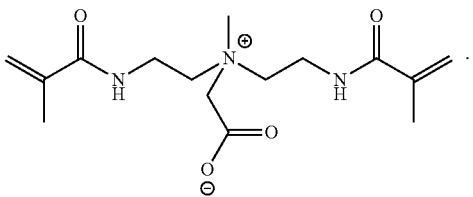 [SMILES: C=C(C)C(=O)NCC[N+](C)(CCNC(=O)C(=C)C)CC(=O)[O-]]

20. The carboxybetaine composition of claim 17 wherein the crosslinker has the formula:

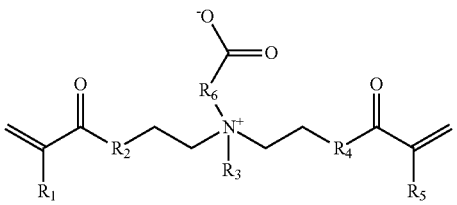

wherein $R_1$ and $R_5$ are H, —$CH_3$, or —$CH_2CH_3$; $R_2$ and $R_4$ are O or NH; $R_3$ is H, —$CH_3$, —$CH_2CH_2OH$, —$CH_2CH_2O$—$COCH$=$CH_2$, —$CH_2CH_2O$—$COC(CH_3)$=$CH_2$, —$CH_2CH_2NH$—$COCH$=$CH_2$, or —$CH_2CH_2NH$—$COC(CH_3)$=$CH_2$ and $R_6$ is —$CH_2$—, —$CH_2CH_2$—, —$CH_2CH_2CH_2$—, —$CH_2CH_2CH_2CH_2$—, —$CH_2CH_2CH_2CH_2CH_2$—.

21. The carboxybetaine composition of claim 17 wherein the crosslinker has the formula:

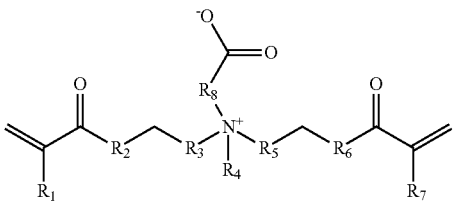

where $R_1$ and $R_7$ are —H, —$CH_3$, or —$CH_2CH_3$; $R_2$ and $R_6$ are O or NH; $R_3$ and $R_5$ are —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —H, $CH_3$, $CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_8$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

22. The zwitterionic composition of claim 1 wherein one or more of the monomers that form the polymer backbone has the formula:

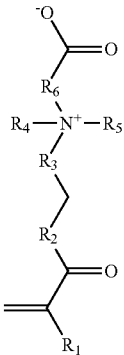

where $R_1$ is —H, —$CH_3$, or —$CH_2CH_3$; $R_2$ is O or NH; $R_3$ is —$CH_2$—, —$CH_2CH_2$—, —$CH_2CH_2CH_2$—, —$CH_2CH_2CH_2CH_2$—, or —$CH_2CH_2CH_2CH_2CH_2$—; $R_4$ is —$CH_2CH_2OH$, —$CH_2CH_2CH_2OH$, —$CH_2CH_2CH_2CH_2OH$, or —$CH_2CH_2CH_2CH_2CH_2OH$; $R_5$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or $CH_2CH_2CH_2CH_2CH_2OH$; and $R_6$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

23. The zwitterionic composition of claim 1 wherein one or more of the monomers that form the polymer backbone has the formula:

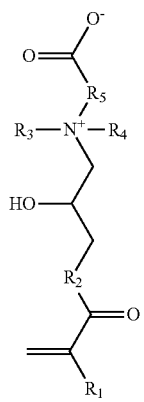

where $R_1$ is —H, —$CH_3$, —$CH_2CH_3$; $R_2$ is O or NH; $R_3$ is —$CH_2CH_2OH$, —$CH_2CH_2CH_2OH$, —$CH_2CH_2CH_2CH_2OH$, or —$CH_2CH_2CH_2CH_2CH_2OH$; $R_4$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or $CH_2CH_2CH_2CH_2CH_2OH$; and $R_5$ is —$CH_2$—, —$CH_2CH_2$—, —$CH_2CH_2CH_2$—, —$CH_2CH_2CH_2CH_2$—, or —$CH_2CH_2CH_2CH_2CH_2$—.

\* \* \* \* \*